United States Patent
Wortz et al.

(10) Patent No.: US 10,842,615 B2
(45) Date of Patent: Nov. 24, 2020

(54) PROSTHETIC CAPSULAR DEVICES, SYSTEMS, AND METHODS

(71) Applicant: Omega Ophthalmics LLC, Versailles, KY (US)

(72) Inventors: Gary N. Wortz, Nicholasville, KY (US); Rick William Ifland, Versailles, KY (US)

(73) Assignee: Omega Ophthalmics LLC, Versailles, KY (US)

( * ) Notice: Subject to any disclaimer, the term of this patent is extended or adjusted under 35 U.S.C. 154(b) by 0 days.

(21) Appl. No.: 15/980,613

(22) Filed: May 15, 2018

(65) Prior Publication Data
US 2019/0015197 A1    Jan. 17, 2019

Related U.S. Application Data

(63) Continuation of application No. 14/742,282, filed on Jun. 17, 2015, now Pat. No. 10,004,594.
(Continued)

(51) Int. Cl.
*A61F 2/14* (2006.01)
*A61F 2/16* (2006.01)
(Continued)

(52) U.S. Cl.
CPC ............ *A61F 2/1618* (2013.01); *A61B 34/25* (2016.02); *A61B 90/04* (2016.02); *A61F 2/14* (2013.01);
(Continued)

(58) Field of Classification Search
CPC .... A61F 2/1613; A61F 2/1618; A61F 2/1629; A61F 2/15; A61F 2/1624; A61F 2/1648;
(Continued)

(56) References Cited

U.S. PATENT DOCUMENTS

| | | |
|---|---|---|
| 4,073,014 A | 2/1978 | Poler |
| 4,373,218 A | 2/1983 | Schachar |

(Continued)

FOREIGN PATENT DOCUMENTS

| | | |
|---|---|---|
| AU | 2014/275390 | 12/2014 |
| AU | 2013/212271 | 8/2015 |

(Continued)

OTHER PUBLICATIONS

Becker, K.A., et al.; accuracy of lens power calculation and centration of an aspheric intraocular lens, Ophthalmologe, Oct. 2006, pp. 873-876, vol. 103, Issue 10, Springer. France.
(Continued)

*Primary Examiner* — Paul B Prebilic
(74) *Attorney, Agent, or Firm* — Knobbe Martens Olson & Bear LLP

(57) ABSTRACT

Prosthetic capsular devices (e.g., bag, bowl, housing, structure, cage, frame) include technology devices such as a computer, virtual reality device, display device, WiFi/internet access device, image receiving device, biometric sensor device, game device, image viewers or senders, GPSs, e-mail devices, combinations thereof, and/or the like. The technology devices can be used in combination with an intraocular lens. The output from the technology device(s) can be fed to the retina of the user to provide a visual image, can be otherwise connected to the user, and/or can be used to control the properties of the intraocular lens or of the prosthetic capsular device. Wearable technology that provides biometric data, such as blood glucose levels, body temperature, electrolyte balance, heart rate, EKG, EEG, intraocular pressure, sensing ciliary muscle contraction for accommodation stimulus, dynamic pupil change and retinal prostheses, combinations thereof, and the like can assist in technology-assisted health care functions.

10 Claims, 68 Drawing Sheets

Related U.S. Application Data

(60) Provisional application No. 62/014,432, filed on Jun. 19, 2014, provisional application No. 62/114,227, filed on Feb. 10, 2015, provisional application No. 62/168,557, filed on May 29, 2015.

(51) Int. Cl.
*A61B 34/00* (2016.01)
*A61B 90/00* (2016.01)
*A61F 9/007* (2006.01)

(52) U.S. Cl.
CPC .............. *A61F 2/15* (2015.04); *A61F 2/1624* (2013.01); *A61F 2/1648* (2013.01); *A61F 2/1659* (2013.01); *A61F 2/1662* (2013.01); *A61F 9/00736* (2013.01); *A61F 2002/1681* (2013.01); *A61F 2002/16901* (2015.04); *A61F 2250/0002* (2013.01)

(58) Field of Classification Search
CPC .. A61F 2002/16901; A61F 2002/16902; A61F 2230/0008; A61F 2230/0065; A61F 2250/001; A61F 2250/0039; A61F 2250/006; A61F 2250/0063; A61F 2250/0065; A61F 2250/0091; A61F 2250/0001; A61B 34/25; A61B 90/04; A61B 2560/0406; A61B 2560/0443–2560/0481
See application file for complete search history.

(56) References Cited

U.S. PATENT DOCUMENTS

| | | |
|---|---|---|
| 4,402,579 A | 10/1983 | Poler |
| 4,423,856 A | 1/1984 | Takahashi et al. |
| 4,435,856 A | 3/1984 | L'Esperance |
| 4,575,373 A | 3/1986 | Johnson |
| 4,585,456 A | 4/1986 | Blackmore |
| 4,629,461 A | 12/1986 | Clayman et al. |
| 4,685,921 A | 8/1987 | Peyman |
| 4,704,124 A | 11/1987 | Shearing |
| 4,731,078 A | 3/1988 | Stoy et al. |
| 4,816,031 A | 3/1989 | Pfoff |
| 4,833,890 A | 5/1989 | Kelman |
| 4,842,601 A | 6/1989 | Smith |
| 4,888,012 A | 12/1989 | Horn et al. |
| 4,888,016 A | 12/1989 | Langerman |
| 4,892,543 A | 1/1990 | Turley |
| 4,932,966 A | 6/1990 | Christie et al. |
| 5,147,395 A | 9/1992 | Willis |
| 5,171,266 A | 12/1992 | Wiley et al. |
| 5,180,390 A | 1/1993 | Drews |
| 5,203,788 A | 4/1993 | Wiley |
| 5,222,981 A | 6/1993 | Werblin |
| 5,275,623 A | 1/1994 | Sarfarazi |
| 5,326,347 A | 7/1994 | Cumming |
| 5,358,520 A | 10/1994 | Patel |
| 5,522,891 A | 6/1996 | Klaas |
| 5,562,731 A | 10/1996 | Cumming |
| 5,628,795 A | 5/1997 | Langerman |
| 5,628,798 A | 5/1997 | Eggleston et al. |
| 5,653,751 A | 8/1997 | Samiy et al. |
| 5,674,282 A | 10/1997 | Cumming |
| 5,676,669 A | 10/1997 | Colvard |
| 5,697,973 A | 12/1997 | Peyman et al. |
| 5,702,402 A | 12/1997 | Brady |
| 5,800,533 A | 9/1998 | Eggleston et al. |
| 5,964,802 A | 10/1999 | Anello et al. |
| 5,968,094 A | 10/1999 | Werblin et al. |
| 5,984,962 A | 11/1999 | Anello et al. |
| 6,015,435 A | 1/2000 | Valunin |
| 6,027,531 A | 2/2000 | Tassignon |
| 6,113,633 A | 9/2000 | Portney |
| 6,117,171 A | 9/2000 | Skottun |
| 6,136,026 A | 10/2000 | Israel |
| 6,143,244 A | 11/2000 | Xia et al. |
| 6,217,612 B1 | 4/2001 | Woods |
| 6,235,055 B1 | 5/2001 | Chu |
| 6,280,471 B1 | 8/2001 | Peyman et al. |
| 6,299,641 B1 | 10/2001 | Woods |
| 6,322,589 B1 | 11/2001 | Cumming |
| 6,413,276 B1 | 7/2002 | Werblin |
| 6,428,574 B1 | 8/2002 | Valunin |
| 6,443,985 B1 | 9/2002 | Woods |
| 6,450,642 B1 | 9/2002 | Jethmalani et al. |
| 6,454,801 B1 | 9/2002 | Portney |
| 6,464,725 B2 | 10/2002 | Skotton |
| 6,488,708 B2 | 12/2002 | Sarfarazi |
| 6,503,276 B2 | 1/2003 | Lang et al. |
| 6,506,212 B2 | 1/2003 | Zhou et al. |
| 6,524,340 B2 | 2/2003 | Israel |
| 6,533,813 B1 | 3/2003 | Lin et al. |
| 6,537,281 B1 | 3/2003 | Portney |
| 6,537,317 B1 | 3/2003 | Steinert |
| 6,576,012 B2 | 6/2003 | Lang |
| 6,596,026 B1 | 7/2003 | Gross |
| 6,645,246 B1 | 11/2003 | Weinschenk |
| 6,695,881 B2 | 2/2004 | Peng et al. |
| 6,721,043 B2 | 4/2004 | Platt et al. |
| 6,749,634 B2 | 6/2004 | Hanna |
| 6,761,737 B2 | 7/2004 | Zadno-Azizi |
| 6,764,511 B2 | 7/2004 | Zadno-Azizi et al. |
| 6,786,934 B2 | 9/2004 | Zadno-Azizi et al. |
| 6,797,004 B1 | 9/2004 | Brady et al. |
| 6,813,097 B2 | 11/2004 | Jethmalani et al. |
| 6,818,158 B2 | 11/2004 | Pham et al. |
| 6,824,266 B2 | 11/2004 | Jethmalani et al. |
| 6,827,738 B2 | 12/2004 | Willis et al. |
| 6,846,326 B2 | 1/2005 | Zadno-Azizi et al. |
| 6,851,804 B2 | 2/2005 | Jethmalani et al. |
| 6,858,040 B2 | 2/2005 | Nguyen et al. |
| 6,881,225 B2 | 4/2005 | Okada |
| 6,884,261 B2 | 4/2005 | Zadno-Azizi et al. |
| 6,884,263 B2 | 4/2005 | Valyunin et al. |
| 6,899,732 B2 | 5/2005 | Zadno-Azizi et al. |
| 6,905,641 B2 | 6/2005 | Platt et al. |
| 6,917,416 B2 | 7/2005 | Platt et al. |
| 6,921,416 B2 | 7/2005 | Khoury |
| 6,926,736 B2 | 8/2005 | Peng et al. |
| 6,960,230 B2 | 11/2005 | Haefliger |
| 6,960,231 B2 | 11/2005 | Tran |
| 6,972,033 B2 | 12/2005 | McNicholas |
| 6,986,900 B2 | 1/2006 | Yaacobi |
| 7,001,374 B2 | 2/2006 | Peyman |
| 7,001,427 B2 | 2/2006 | Aharoni et al. |
| 7,025,783 B2 | 4/2006 | Bradu et al. |
| 7,029,497 B2 | 4/2006 | Zhang et al. |
| 7,041,134 B2 | 5/2006 | Nguyen et al. |
| 7,074,840 B2 | 7/2006 | Chang et al. |
| 7,087,080 B2 | 8/2006 | Zadno-Azizi et al. |
| 7,105,110 B2 | 9/2006 | Platt et al. |
| 7,118,596 B2 | 10/2006 | Zadno-Azizi et al. |
| 7,119,894 B2 | 10/2006 | Platt et al. |
| 7,122,053 B2 | 10/2006 | Esch |
| 7,125,422 B2 | 10/2006 | Woods |
| 7,134,755 B2 | 11/2006 | Jethmalani et al. |
| 7,144,423 B2 | 12/2006 | McDonald |
| 7,150,760 B2 | 12/2006 | Zhang |
| 7,198,640 B2 | 4/2007 | Nguyen |
| 7,210,783 B2 | 5/2007 | Jethmalani et al. |
| 7,223,288 B2 | 5/2007 | Zhang et al. |
| 7,226,478 B2 | 6/2007 | Ting et al. |
| 7,237,893 B2 | 7/2007 | Chang et al. |
| 7,241,009 B2 | 7/2007 | Kornfield et al. |
| 7,281,795 B2 | 10/2007 | Sandstedt et al. |
| 7,300,464 B2 | 11/2007 | Tran |
| 7,414,714 B2 | 8/2008 | Platt et al. |
| 7,452,362 B2 | 11/2008 | Zadno-Azizi et al. |
| 7,452,378 B2 | 11/2008 | Zadno-Azizi et al. |
| 7,462,193 B2 | 12/2008 | Nagamoto |
| 7,560,499 B2 | 7/2009 | Jethmalani et al. |
| 7,658,364 B2 | 2/2010 | Robinson et al. |

(56) References Cited

U.S. PATENT DOCUMENTS

| | | |
|---|---|---|
| 7,662,179 B2 | 2/2010 | Sarfarazi |
| 7,713,299 B2 | 5/2010 | Brady et al. |
| 7,744,603 B2 | 6/2010 | Zadno-Azizi et al. |
| 7,744,646 B2 | 6/2010 | Zadno-Azizi et al. |
| 7,771,471 B2 | 8/2010 | Dell |
| 7,780,729 B2 | 8/2010 | Nguyen et al. |
| 7,798,644 B2 | 9/2010 | Jethmalani et al. |
| 7,806,929 B2 | 10/2010 | Brown |
| 7,811,320 B2 | 10/2010 | Werblin et al. |
| 7,837,326 B2 | 11/2010 | Jethmalani et al. |
| 7,871,437 B2 | 1/2011 | Hermans et al. |
| 7,988,285 B2 | 8/2011 | Sandstedt et al. |
| 7,988,291 B2 | 8/2011 | Ianchulev |
| 8,025,823 B2 | 9/2011 | Pham et al. |
| 8,034,107 B2 | 10/2011 | Stenger |
| 8,048,155 B2 | 11/2011 | Shadduck |
| 8,052,752 B2 | 11/2011 | Woods et al. |
| 8,062,361 B2 | 11/2011 | Nguyen et al. |
| 8,088,161 B2 | 1/2012 | Aharoni et al. |
| 8,100,965 B2 | 1/2012 | Cumming |
| 8,128,693 B2 | 3/2012 | Tran et al. |
| 8,162,927 B2 | 4/2012 | Peyman et al. |
| 8,187,325 B2 | 5/2012 | Zadno-Azizi et al. |
| 8,197,539 B2 | 6/2012 | Nasiatka et al. |
| 8,246,679 B2 | 8/2012 | Nguyen et al. |
| 8,273,123 B2 | 9/2012 | Nun |
| 8,343,216 B2 | 1/2013 | Brady et al. |
| 8,361,353 B2 | 1/2013 | Brait et al. |
| 8,398,709 B2 | 3/2013 | Nun et al. |
| 8,486,142 B2 | 7/2013 | Bumbalough et al. |
| 8,505,822 B2 | 8/2013 | Wang et al. |
| 8,506,074 B2 | 8/2013 | Gerbaud |
| 8,545,556 B2 | 10/2013 | Woods et al. |
| 8,556,967 B2 | 10/2013 | Sarfarazi et al. |
| 8,574,295 B2 | 11/2013 | Roholt |
| 8,579,971 B2 | 11/2013 | Webb |
| 8,585,556 B2 | 11/2013 | Woods et al. |
| 8,585,758 B2 | 11/2013 | Woods |
| 8,608,799 B2 | 12/2013 | Blake et al. |
| 8,663,235 B2 | 3/2014 | Tassignon |
| 8,728,158 B2 | 5/2014 | Whitsett |
| 8,778,022 B2 | 7/2014 | Blum et al. |
| 8,821,166 B2 | 9/2014 | Akura et al. |
| 8,834,565 B2 | 9/2014 | Nun |
| 8,900,300 B1 | 12/2014 | Wortz |
| 8,915,588 B2 | 12/2014 | Blum et al. |
| 8,931,896 B2 | 1/2015 | Blum et al. |
| 9,005,282 B2 | 4/2015 | Chang et al. |
| 9,005,283 B2 | 4/2015 | Nguyen et al. |
| 9,039,760 B2 | 5/2015 | Brady et al. |
| 9,072,600 B2 | 7/2015 | Tran |
| 9,078,744 B2 | 7/2015 | Van Noy |
| 9,095,424 B2 | 8/2015 | Kahook et al. |
| 9,119,710 B2 | 9/2015 | Grubbs et al. |
| 9,124,796 B2 | 9/2015 | Blum et al. |
| 9,125,736 B2 | 9/2015 | Kahook et al. |
| 9,149,356 B2 | 10/2015 | Sarfarazi |
| 9,173,527 B2 | 11/2015 | Ulrich et al. |
| 9,186,243 B2 | 11/2015 | Van Noy |
| 9,198,752 B2 | 12/2015 | Woods |
| 9,289,287 B2 | 3/2016 | Kahook et al. |
| 9,339,375 B2 | 5/2016 | Lee et al. |
| 9,358,103 B1 | 6/2016 | Wortz et al. |
| 9,364,316 B1 | 6/2016 | Kahook et al. |
| 9,387,069 B2 | 7/2016 | Kahook et al. |
| 9,414,907 B2 | 8/2016 | Wortz et al. |
| 9,421,088 B1 | 8/2016 | Kahook et al. |
| 9,439,754 B2 | 9/2016 | Wortz |
| 9,504,558 B2 | 11/2016 | Wortz et al. |
| 9,517,127 B2 | 12/2016 | Wortz et al. |
| 9,522,059 B2 | 12/2016 | Wortz et al. |
| 9,522,060 B2 | 12/2016 | Wortz et al. |
| 9,554,890 B2 | 1/2017 | Wortz et al. |
| 9,597,176 B2 | 3/2017 | Wortz et al. |
| 9,629,712 B2 | 4/2017 | Stenger |
| 9,642,699 B2 | 5/2017 | Wortz et al. |
| 9,681,946 B2 | 6/2017 | Kahook et al. |
| 9,763,771 B1 | 9/2017 | Wortz et al. |
| 9,925,037 B2 | 3/2018 | Wortz et al. |
| 9,993,336 B2 | 6/2018 | Wortz et al. |
| 10,004,594 B2 | 6/2018 | Wortz et al. |
| 10,111,746 B2 | 10/2018 | Wortz et al. |
| 10,136,989 B2 | 11/2018 | Wortz et al. |
| 10,271,945 B2 | 4/2019 | Wortz et al. |
| 10,492,903 B1 | 7/2019 | Wortz et al. |
| 2001/0047204 A1 | 11/2001 | Zhou et al. |
| 2001/0051825 A1 | 12/2001 | Peterson |
| 2002/0128710 A1 | 9/2002 | Eggleston |
| 2002/0143395 A1 | 10/2002 | Skottun |
| 2002/0173846 A1 | 11/2002 | Blake et al. |
| 2003/0004569 A1 | 1/2003 | Haefliger |
| 2003/0050695 A1 | 3/2003 | Lin et al. |
| 2003/0090624 A1 | 5/2003 | Jethmalani et al. |
| 2003/0149479 A1 | 8/2003 | Snyder et al. |
| 2003/0149480 A1 | 8/2003 | Shadduck |
| 2003/0151831 A1 | 8/2003 | Sandstedt et al. |
| 2003/0176521 A1 | 9/2003 | Jethmalani et al. |
| 2003/0187505 A1 | 10/2003 | Liao |
| 2004/0064182 A1 | 4/2004 | Kelman |
| 2004/0082993 A1 | 4/2004 | Woods |
| 2004/0082995 A1 | 4/2004 | Woods |
| 2004/0106993 A1 | 6/2004 | Portney |
| 2004/0117011 A1 | 6/2004 | Aharoni et al. |
| 2004/0148022 A1 | 7/2004 | Eggleston |
| 2004/0158322 A1 | 8/2004 | Shen et al. |
| 2004/0167622 A1 | 8/2004 | Sunlap et al. |
| 2004/0208910 A1 | 10/2004 | Ashton et al. |
| 2004/0254438 A1 | 12/2004 | Chuck et al. |
| 2005/0021138 A1 | 1/2005 | Woods |
| 2005/0085907 A1 | 4/2005 | Hanna |
| 2005/0099597 A1 | 5/2005 | Sandstedt et al. |
| 2005/0107875 A1 | 5/2005 | Cumming |
| 2005/0113911 A1 | 5/2005 | Peyman |
| 2005/0113913 A1 | 5/2005 | Duvert et al. |
| 2005/0137703 A1 | 6/2005 | Chen |
| 2005/0154457 A1 | 7/2005 | Aharoni et al. |
| 2005/0187623 A1 | 8/2005 | Tassignon |
| 2005/0222577 A1 | 10/2005 | Vaquero |
| 2005/0234285 A1 | 10/2005 | Khoury |
| 2005/0246018 A1 | 11/2005 | Grubbs et al. |
| 2006/0027939 A1 | 2/2006 | Brait et al. |
| 2006/0047339 A1 | 3/2006 | Brown |
| 2006/0064161 A1 | 3/2006 | Blake |
| 2006/0095128 A1 | 5/2006 | Blum et al. |
| 2006/0212116 A1 | 9/2006 | Woods |
| 2006/0253196 A1* | 11/2006 | Woods ............... A61F 2/1613 623/6.13 |
| 2006/0259139 A1 | 11/2006 | Zadno-Azizi et al. |
| 2006/0261502 A1 | 11/2006 | Platt et al. |
| 2007/0027538 A1 | 2/2007 | Aharoni et al. |
| 2007/0027541 A1 | 2/2007 | Aharoni et al. |
| 2007/0032868 A1 | 2/2007 | Woods |
| 2007/0083261 A1 | 4/2007 | Colvard |
| 2007/0093892 A1 | 4/2007 | MacKool |
| 2007/0100444 A1 | 5/2007 | Brady et al. |
| 2007/0118216 A1 | 5/2007 | Pynson |
| 2007/0123767 A1 | 5/2007 | Montegrande et al. |
| 2007/0123981 A1 | 5/2007 | Tassignon |
| 2007/0162118 A1 | 7/2007 | Rozakis et al. |
| 2007/0213816 A1 | 9/2007 | Sarfarazi |
| 2007/0244560 A1 | 10/2007 | Ossipov et al. |
| 2007/0260308 A1 | 11/2007 | Tran |
| 2008/0086206 A1 | 4/2008 | Nasiatka et al. |
| 2008/0097599 A1 | 4/2008 | Rozakis et al. |
| 2008/0221676 A1 | 9/2008 | Coleman et al. |
| 2008/0300680 A1 | 12/2008 | Joshua |
| 2009/0005864 A1 | 1/2009 | Eggleston |
| 2009/0182423 A1 | 7/2009 | Zheng |
| 2010/0022945 A1 | 1/2010 | Rodstrom |
| 2010/0030225 A1 | 2/2010 | Ianchulev |
| 2010/0204788 A1 | 8/2010 | Van Noy |
| 2010/0211171 A1 | 8/2010 | Sarfarazi |
| 2010/0228344 A1 | 9/2010 | Shadduck |
| 2010/0280609 A1 | 11/2010 | Simonov et al. |

(56) References Cited

U.S. PATENT DOCUMENTS

| | | |
|---|---|---|
| 2011/0015541 A1 | 1/2011 | Padrick et al. |
| 2011/0153014 A1 | 6/2011 | Zhang et al. |
| 2011/0181834 A1 | 7/2011 | Gerbaud |
| 2011/0224788 A1 | 9/2011 | Webb |
| 2011/0288638 A1 | 11/2011 | Smiley et al. |
| 2011/0040378 A1 | 12/2011 | Werblin |
| 2011/0295367 A1 | 12/2011 | Cuevas |
| 2011/0313521 A1 | 12/2011 | Angelopoulos |
| 2012/0078363 A1 | 3/2012 | Lu et al. |
| 2012/0078364 A1* | 3/2012 | Stenger ............... A61F 2/1629 623/6.39 |
| 2012/0179249 A1 | 7/2012 | Coleman |
| 2012/0226351 A1 | 9/2012 | Peyman |
| 2012/0238857 A1 | 9/2012 | Wong et al. |
| 2012/0253458 A1 | 10/2012 | Geraghty et al. |
| 2013/0072591 A1 | 3/2013 | Sandstedt et al. |
| 2013/0116781 A1 | 5/2013 | Nun |
| 2013/0184815 A1 | 7/2013 | Roholt |
| 2013/0190868 A1 | 7/2013 | Kahook et al. |
| 2013/0197637 A1 | 8/2013 | Brait et al. |
| 2013/0245754 A1 | 9/2013 | Blum et al. |
| 2013/0289153 A1 | 10/2013 | Sandstedt et al. |
| 2013/0304206 A1 | 11/2013 | Pallikaris et al. |
| 2013/0310931 A1 | 11/2013 | Kahook et al. |
| 2013/0317458 A1 | 11/2013 | Kopczynski et al. |
| 2014/0052246 A1 | 2/2014 | Kahook et al. |
| 2014/0067059 A1 | 3/2014 | Webb |
| 2014/0172089 A1 | 6/2014 | Lee et al. |
| 2014/0228949 A1 | 8/2014 | Argento et al. |
| 2014/0343379 A1 | 11/2014 | Pugh |
| 2014/0371852 A1 | 12/2014 | Aharoni et al. |
| 2014/0379079 A1* | 12/2014 | Ben Nun ............... A61F 2/1613 623/6.37 |
| 2015/0061990 A1 | 3/2015 | Toner et al. |
| 2015/0088253 A1 | 3/2015 | Doll et al. |
| 2015/0100046 A1 | 4/2015 | Ambati et al. |
| 2015/0127102 A1 | 5/2015 | Wortz |
| 2015/0142106 A1 | 5/2015 | Wortz |
| 2015/0157452 A1 | 6/2015 | Maliarov et al. |
| 2015/0182330 A1 | 7/2015 | Grant |
| 2015/0230981 A1 | 8/2015 | Kahook et al. |
| 2015/0238309 A1 | 8/2015 | Jansen et al. |
| 2015/0272727 A1 | 10/2015 | Humayun et al. |
| 2015/0289970 A1 | 10/2015 | Akura |
| 2015/0335420 A1 | 11/2015 | Blum et al. |
| 2015/0366656 A1 | 12/2015 | Wortz et al. |
| 2015/0366659 A1 | 12/2015 | Wortz et al. |
| 2015/0366660 A1 | 12/2015 | Martinez et al. |
| 2016/0000558 A1 | 1/2016 | Honigsbaum |
| 2016/0008126 A1 | 1/2016 | Salahieh et al. |
| 2016/0030161 A1 | 2/2016 | Brady et al. |
| 2016/0030163 A1 | 2/2016 | Akahoshi |
| 2016/0058552 A1 | 3/2016 | Argal et al. |
| 2016/0058553 A1 | 3/2016 | Salahieh et al. |
| 2016/0074154 A1 | 3/2016 | Woods |
| 2016/0113760 A1 | 4/2016 | Conrad |
| 2016/0113761 A1 | 4/2016 | Nishi et al. |
| 2016/0235524 A1 | 8/2016 | Wortz et al. |
| 2016/0278912 A1 | 9/2016 | Kahook et al. |
| 2016/0310263 A1 | 10/2016 | Akura |
| 2016/0317287 A1 | 11/2016 | Silverstrini et al. |
| 2016/0324629 A1 | 11/2016 | Sandstedt et al. |
| 2016/0331519 A1 | 11/2016 | Kahook et al. |
| 2016/0338825 A1 | 11/2016 | Wortz et al. |
| 2016/0339657 A1 | 11/2016 | Grubbs et al. |
| 2017/0000602 A1 | 1/2017 | Sohn et al. |
| 2017/0020658 A1 | 1/2017 | Grubbs et al. |
| 2017/0042667 A1 | 2/2017 | Collins et al. |
| 2017/0049560 A1 | 2/2017 | Cherne |
| 2017/0119521 A1 | 5/2017 | Kahook et al. |
| 2017/0172732 A1 | 6/2017 | Lu et al. |
| 2017/0319332 A1 | 11/2017 | Kahook et al. |
| 2017/0348094 A1 | 12/2017 | Sohn |
| 2017/0348095 A1 | 12/2017 | Wortz et al. |
| 2018/0055625 A1 | 3/2018 | Wortz et al. |
| 2018/0271642 A1 | 9/2018 | Wortz et al. |
| 2019/0076239 A1 | 3/2019 | Wortz et al. |
| 2019/0083235 A1 | 3/2019 | Wortz |
| 2019/0307552 A1 | 10/2019 | Wortz |
| 2019/0343621 A1 | 11/2019 | Wortz |

FOREIGN PATENT DOCUMENTS

| | | |
|---|---|---|
| CA | 2 861 865 | 8/2013 |
| CA | 2 913 897 | 12/2014 |
| CA | 2 864 882 | 6/2015 |
| CA | 2 974 639 | 8/2016 |
| EP | 0 337 390 | 10/1989 |
| EP | 0 294 039 | 7/1993 |
| EP | 0 528 325 | 12/1996 |
| EP | 916320 | 5/1999 |
| EP | 0 916 320 | 12/1999 |
| EP | 0 732 090 | 6/2002 |
| EP | 1 653 886 | 5/2006 |
| EP | 1 499 264 | 8/2006 |
| EP | 1 100 411 | 11/2006 |
| EP | 1 694 253 | 8/2007 |
| EP | 1 852 090 | 11/2007 |
| EP | 1 562 521 | 12/2009 |
| EP | 1 475 055 | 4/2010 |
| EP | 1 933 768 | 10/2010 |
| EP | 2 315 559 | 5/2011 |
| EP | 1 438 930 | 9/2011 |
| EP | 2 412 337 | 2/2012 |
| EP | 1 296 616 | 5/2012 |
| EP | 1 906 881 | 8/2012 |
| EP | 2 512 374 | 10/2012 |
| EP | 2 851 038 | 3/2015 |
| EP | 2 620 130 | 7/2016 |
| EP | 2 816 972 | 3/2017 |
| EP | 3 181 095 | 6/2017 |
| EP | 3 157 466 | 12/2017 |
| FR | 2 799 637 | 4/2001 |
| FR | 2 804 860 | 8/2001 |
| FR | 2 966 340 | 4/2012 |
| JP | S63-89154 | 4/1988 |
| JP | 02-011134 | 1/1990 |
| JP | H08-317943 | 12/1996 |
| JP | H09-173363 | 7/1997 |
| JP | 2004-523316 | 6/2005 |
| JP | 2005-143886 | 6/2005 |
| JP | 2007029727 | 2/2007 |
| JP | 2013-544116 | 12/2013 |
| JP | 2015-507946 | 3/2015 |
| JP | 57 85678 | 9/2015 |
| JP | 2016-524503 | 8/2016 |
| JP | 2017-505702 | 2/2017 |
| JP | 2017-519221 | 7/2017 |
| WO | WO 1998/017205 | 4/1998 |
| WO | WO 1999/024541 | 5/1999 |
| WO | WO 1999/062433 | 12/1999 |
| WO | WO 01/64136 | 9/2001 |
| WO | WO 2002/026121 | 4/2002 |
| WO | WO 2002/071983 | 9/2002 |
| WO | WO 2003/058296 | 7/2003 |
| WO | WO 2005/016191 | 2/2005 |
| WO | WO 2005/094727 | 10/2005 |
| WO | WO 2005/107649 | 11/2005 |
| WO | WO 2006/002201 | 1/2006 |
| WO | WO 2006/050171 | 5/2006 |
| WO | WO 2006/124016 | 11/2006 |
| WO | WO 2006/135572 | 12/2006 |
| WO | WO 2007/030799 | 3/2007 |
| WO | WO 2006/015315 | 4/2007 |
| WO | WO 07/121296 | 10/2007 |
| WO | WO 2010/002215 | 4/2010 |
| WO | WO 2011/163080 | 12/2011 |
| WO | WO 12/067994 | 5/2012 |
| WO | WO 12/161749 | 11/2012 |
| WO | WO 2013/039707 | 3/2013 |
| WO | WO 2013/112589 | 8/2013 |
| WO | WO 2013/126380 | 8/2013 |
| WO | WO 2014/167425 | 10/2014 |
| WO | WO 2014/197170 | 12/2014 |

(56) References Cited

FOREIGN PATENT DOCUMENTS

| WO | WO 2014/201956 | 12/2014 |
|---|---|---|
| WO | WO 2015/044235 | 4/2015 |
| WO | WO 2015/066532 | 5/2015 |
| WO | WO 2015/126604 | 8/2015 |
| WO | WO 2015/195825 | 12/2015 |
| WO | WO 2015/198236 | 12/2015 |
| WO | WO 2015/200056 | 12/2015 |
| WO | WO 2016/122805 | 8/2016 |
| WO | WO 2016/187497 | 11/2016 |
| WO | WO 2017/030582 | 2/2017 |
| WO | WO 2017/079449 | 5/2017 |
| WO | WO 2017/192855 | 11/2017 |

OTHER PUBLICATIONS

International Preliminary Report on Patentability, dated Aug. 26, 2014, in PCT App. No. PCT/US2013/026820.
International Preliminary Report on Patentability, dated Dec. 20, 2016, in PCT App. No. PCT/US2015/036263.
International Search Report and Written Opinion issued in PCT Application No. PCT/US2015/036263, dated Oct. 7, 2015.
International Search Report and Written Opinion issued in PCT Application No. PCT/US2015/065887, dated Apr. 6, 2016.
International Search report and Written Opinoin dated May 31, 2013 for Application No. PCT/US2013/026820.
Kleiman, L.Z., et al.; Post-operative Results with Implantation of the Acrysof SA-60 Intraocular lens into the Ciliary Sulcus, Arvo Annual meeting Abstract Search and Program Planner, May 2002; pp. Abstract No. 380; vol. 2002., Annual Meeting of the Association for Research in Vision and Ophthalmology, Ft. Lauderdale, Florida, USA.
Kleinmann, "Open-Capsule Device for PCO Prevention", Oct. 17, 2013.
Koeppl, C. et al.; Change in IOL position and capsular bag size with an angulated intraocular lens early after cataract surgery, Journal of Cataract and Refractive Surgery, Feb. 2005, pp. 348-353, vol. 31, issue 2., Elsevier Science, Inc. New York City, NY, USA.
Krader, "Small-aperture optic IOL broadens range of vision", Dec. 1, 2014.
Lim, Mcc, et al.; Surgical management of late dislocated lens capsular bag with intraocular lens and endocapsular tension ring, Journal of Cataract and Refractive Surgery, Mar. 2006, pp. 533-535, vol. 32, Issue 3, Elsevier Science, Inc., New York City, NY, USA.
Notice of Allowance issued in Japanese Patent Application No. 2014-558790, dated Jun. 25, 2015, in 3 pages.
Notice of Allowance issued in U.S. Appl. No. 14/968,427, dated Apr. 26, 2016.
Office Action issued in European Application No. 13710641.5, dated Oct. 1, 2015, in 5 pages.
Office Action issued in Japanese Patent Application No. 2014-558790, dated Feb. 3, 2015, in 9 pages.
Office Action issued in Japanese Patent Application No. 2015-146248, dated Nov. 28, 2016, in 13 pages.
Postive Phase I/II Interim Data of Bimatoprost Sustained-Release Implant for IOP Therapy in Glaucoma, Nov. 16, 2015, http://www.allergan.com/NEWS/News/Thomson-Reuters/Positive-Phase-I-II-Interim-Data-of-Bimatoprost-Su.
Restriction Requirement issued in U.S. Appl. No. 14/968,427, dated Mar. 24, 2016.
"Tracking IOP With an IOL," Sep. 15, 2014.
Wirtitsch, M.g., et al.; Effect of haptic design on change in axial lens posiiton after cataract surgery, Journal of Cataract and Refractive Surgery, Jan. 2004, pp. 45-51, vol. 30, issue 1. 19th Congress of the European-Society-of-Cataract-and-Refractive-Surgeons, Elsevier Science, inc., New York City, NY, USA.

\* cited by examiner

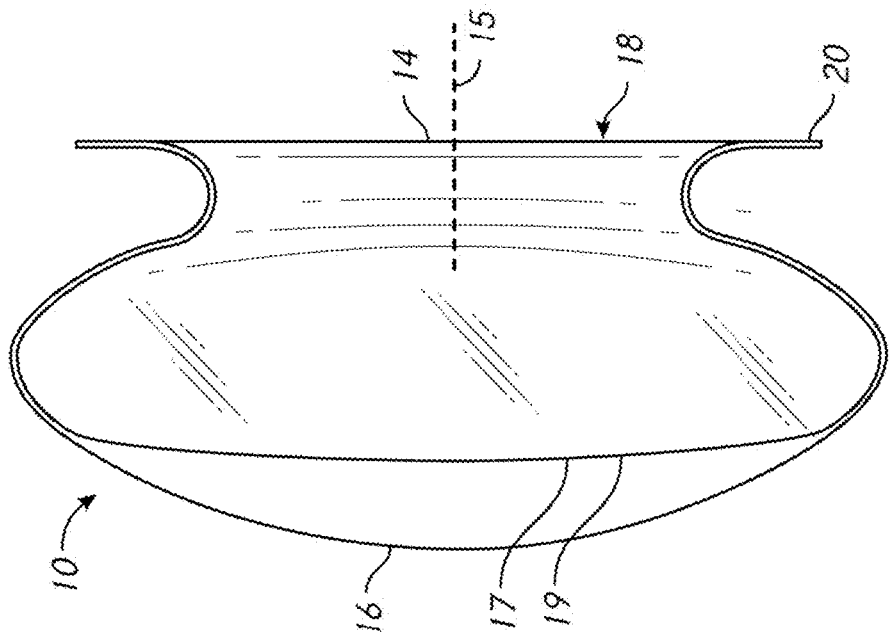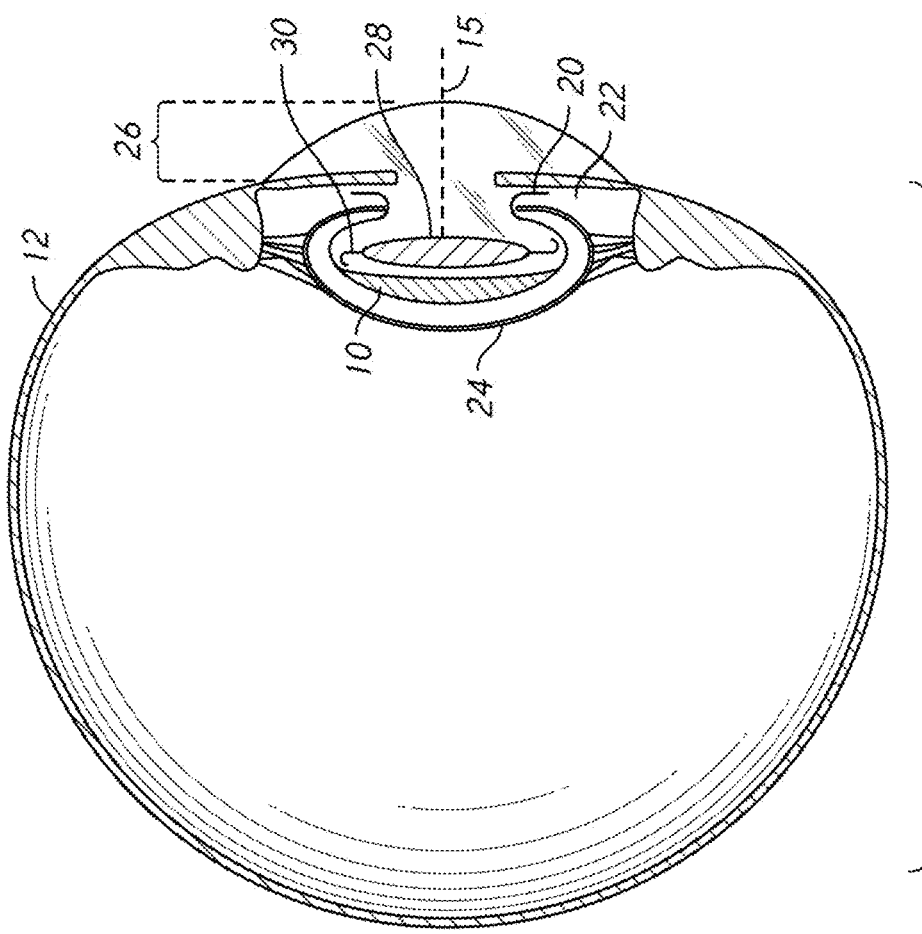

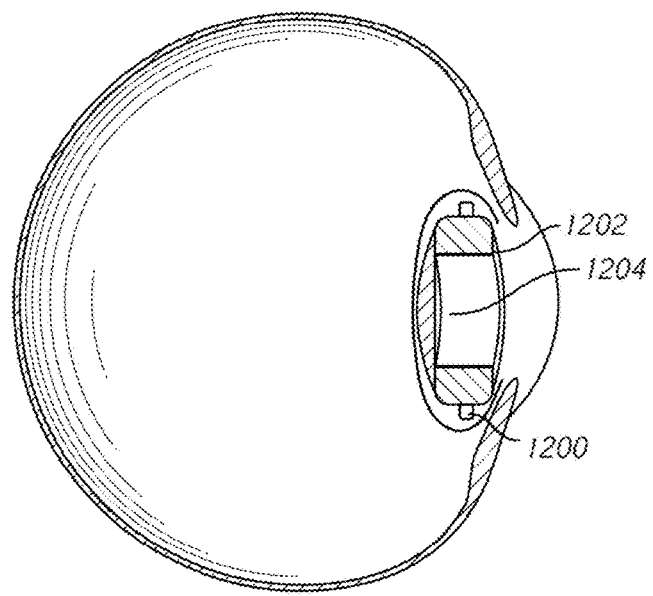
FIG. 12A
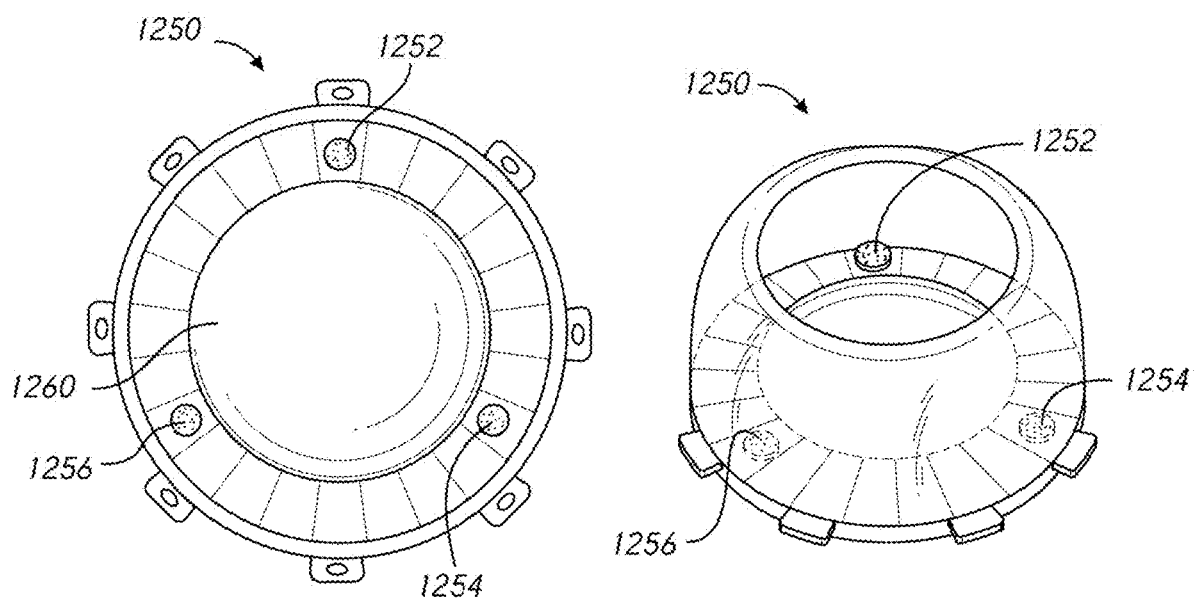
FIG. 12B
FIG. 12C

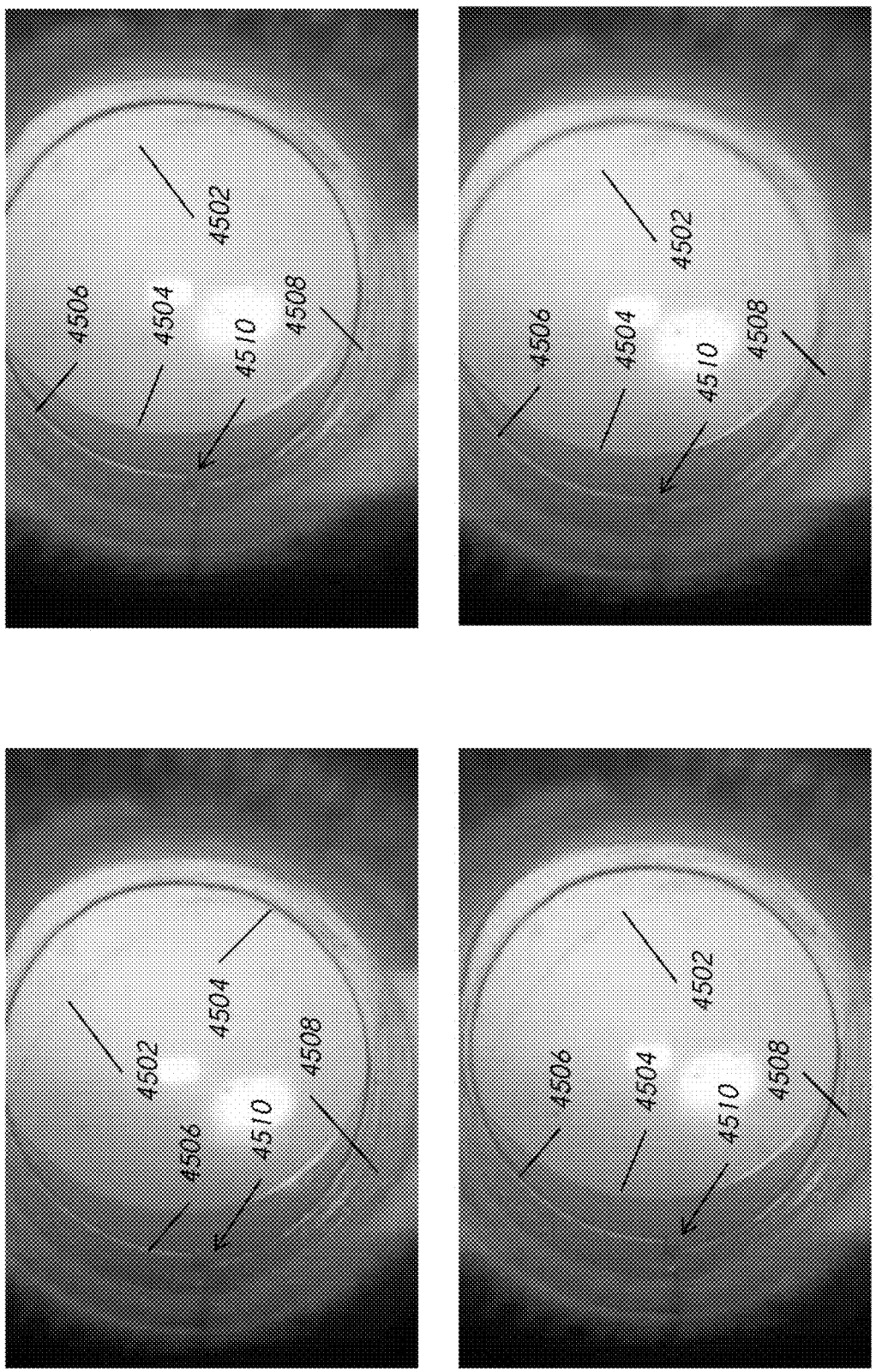

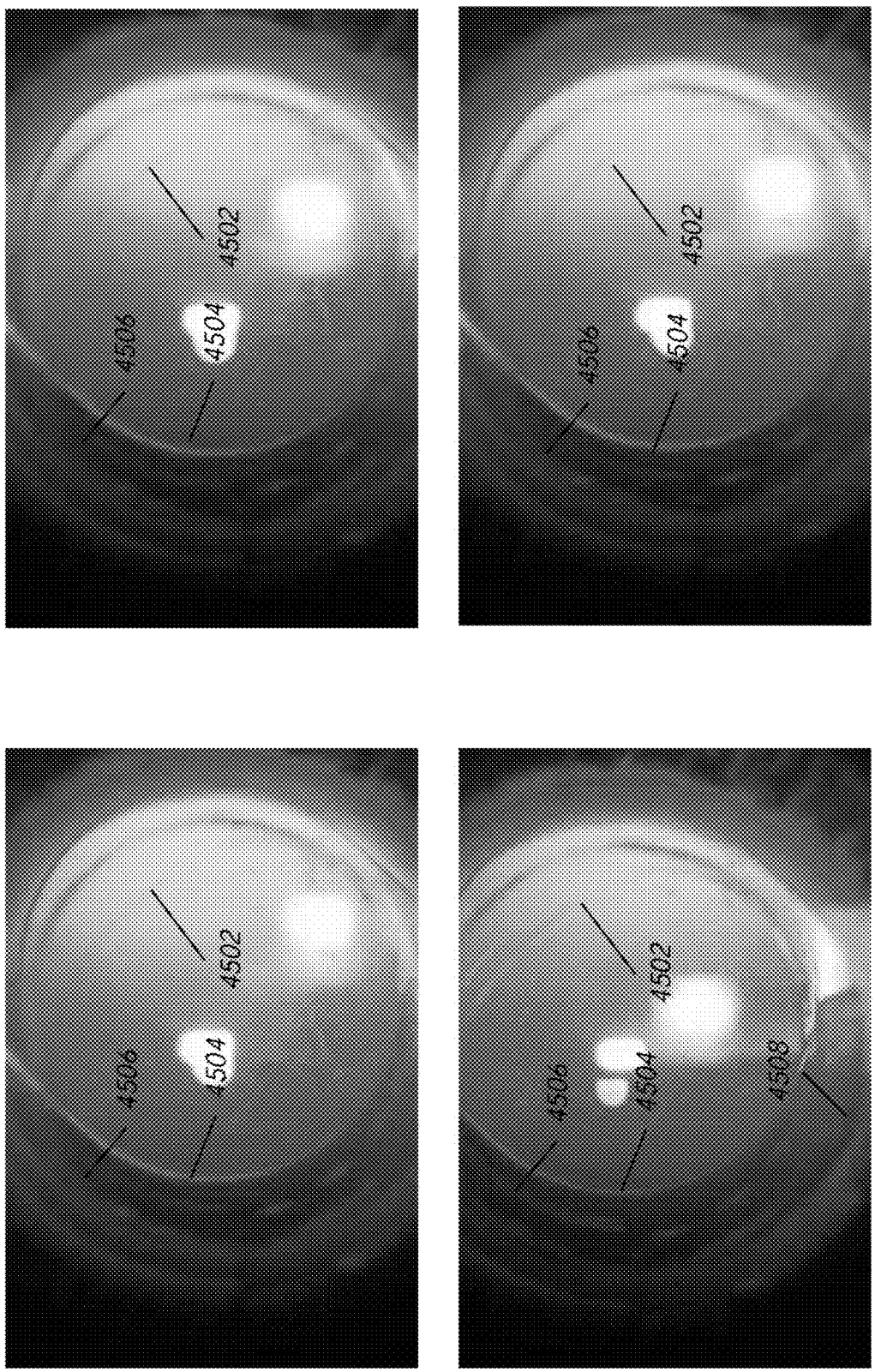

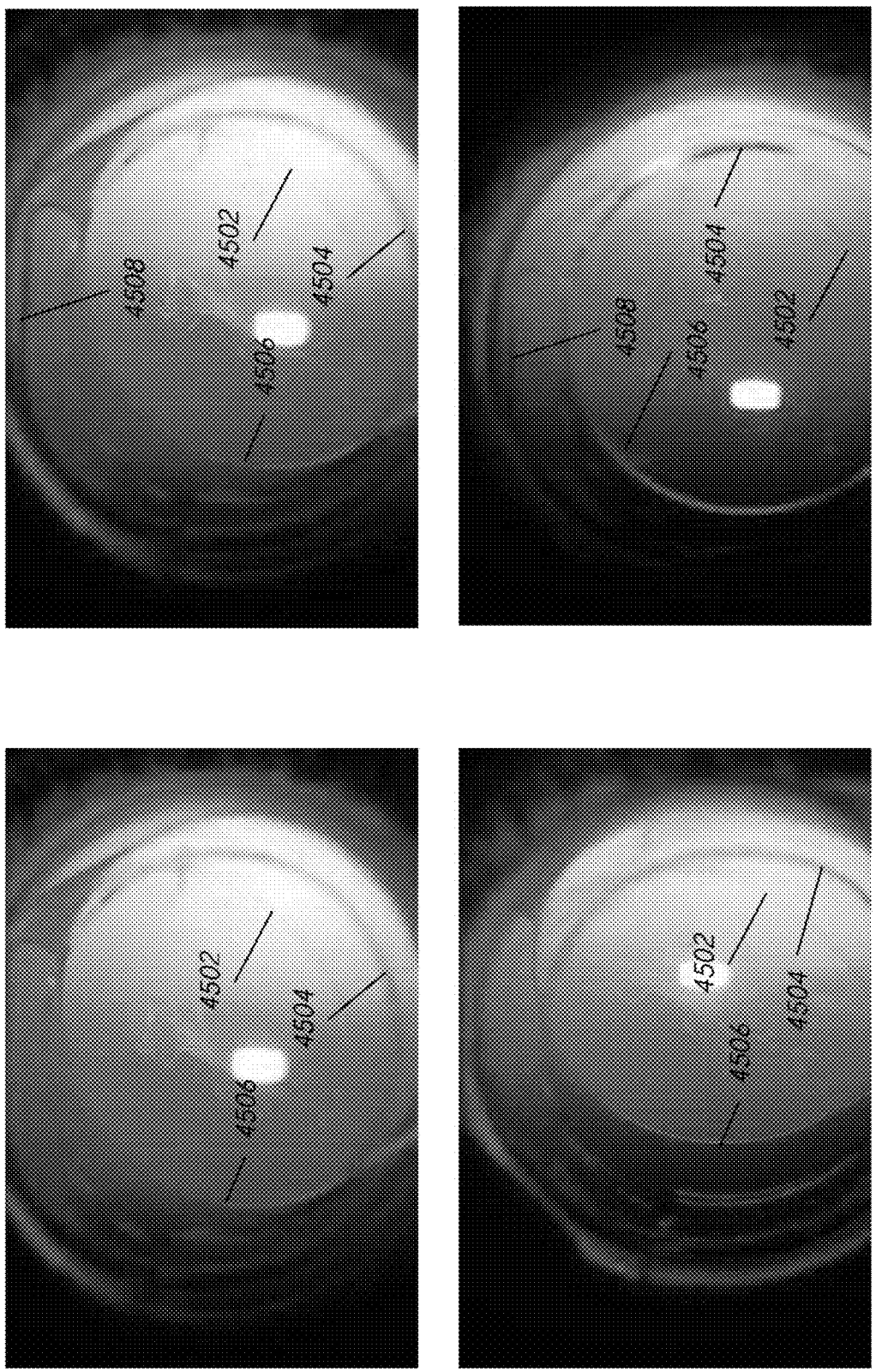

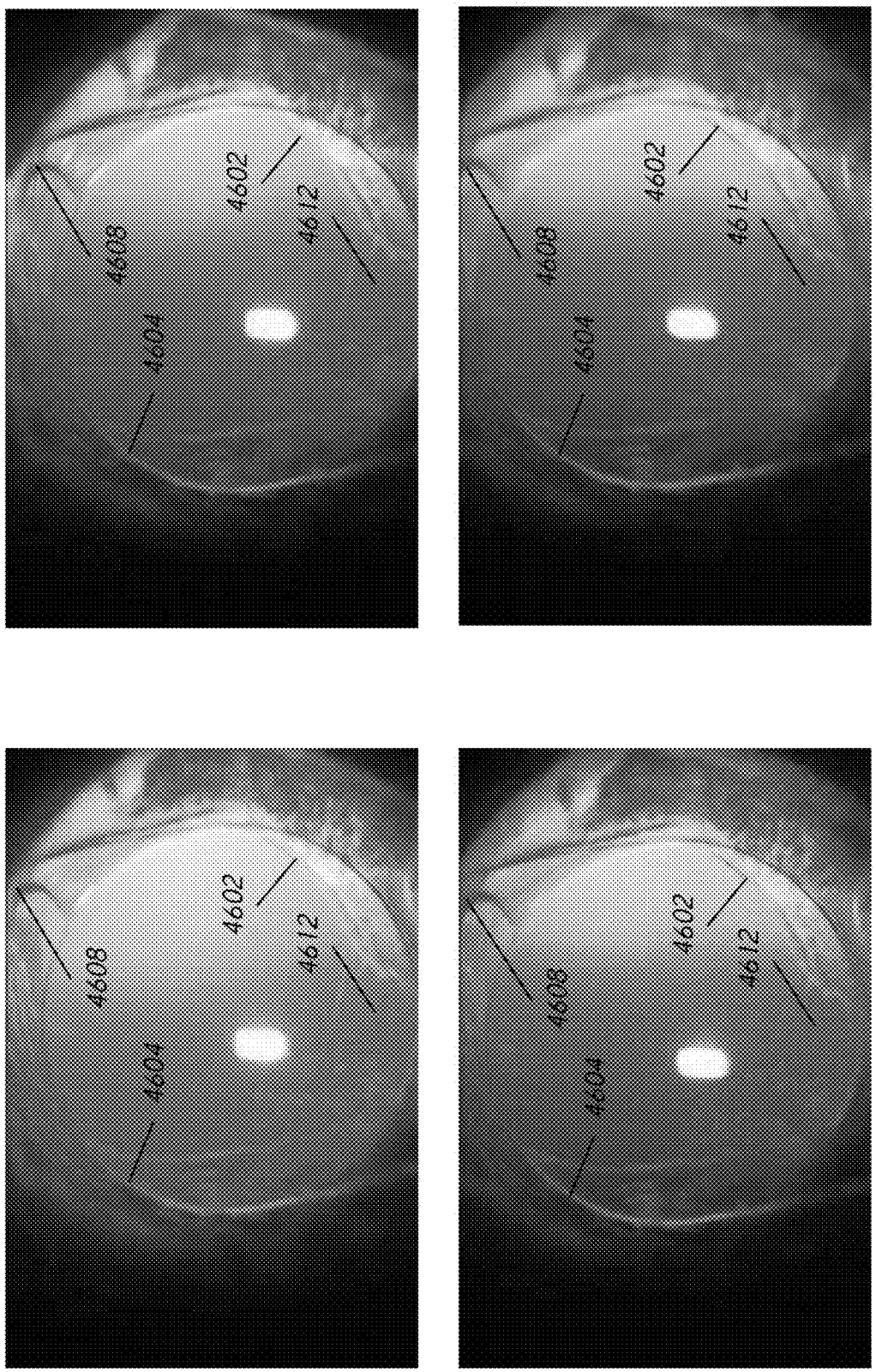

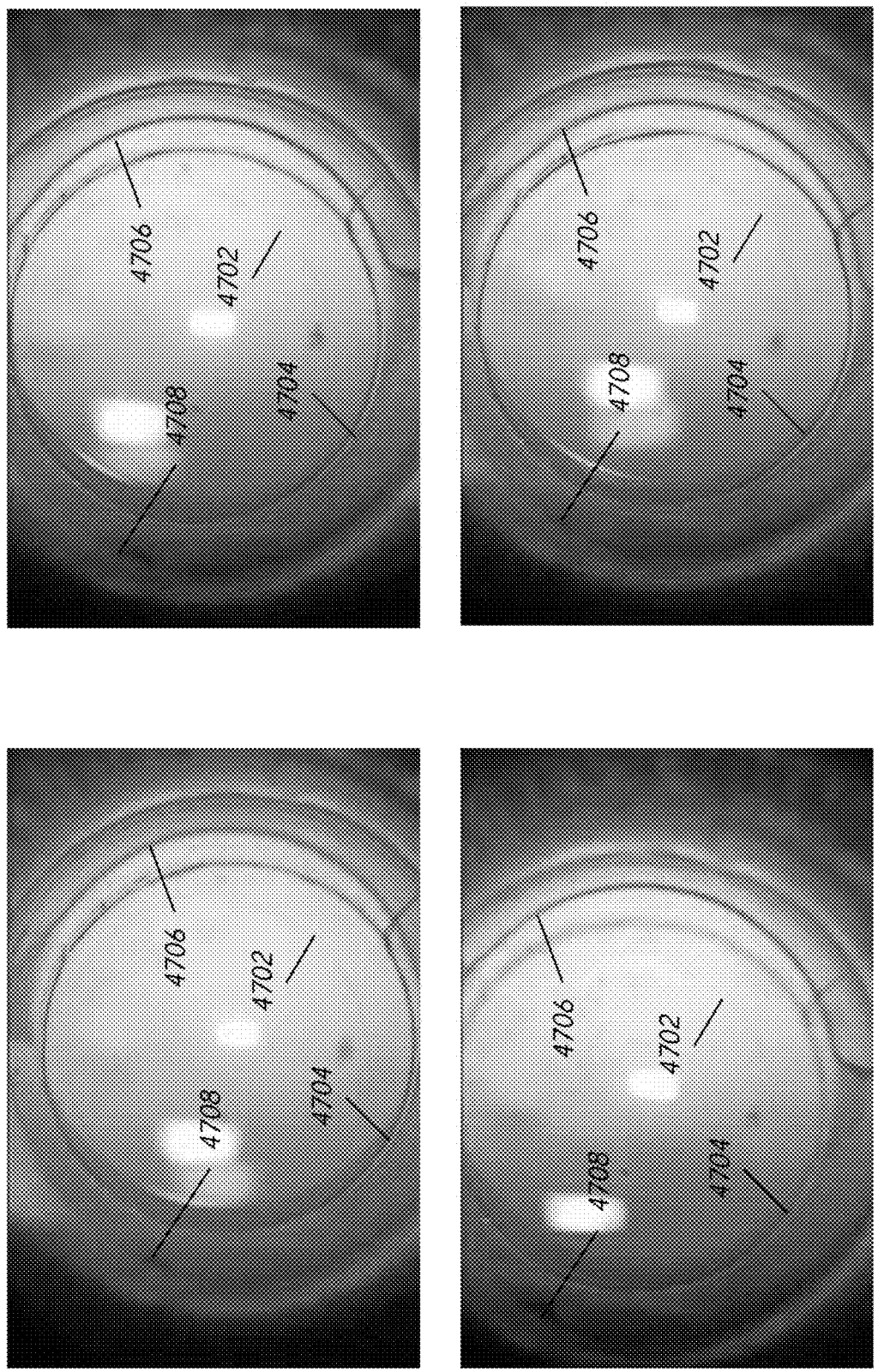

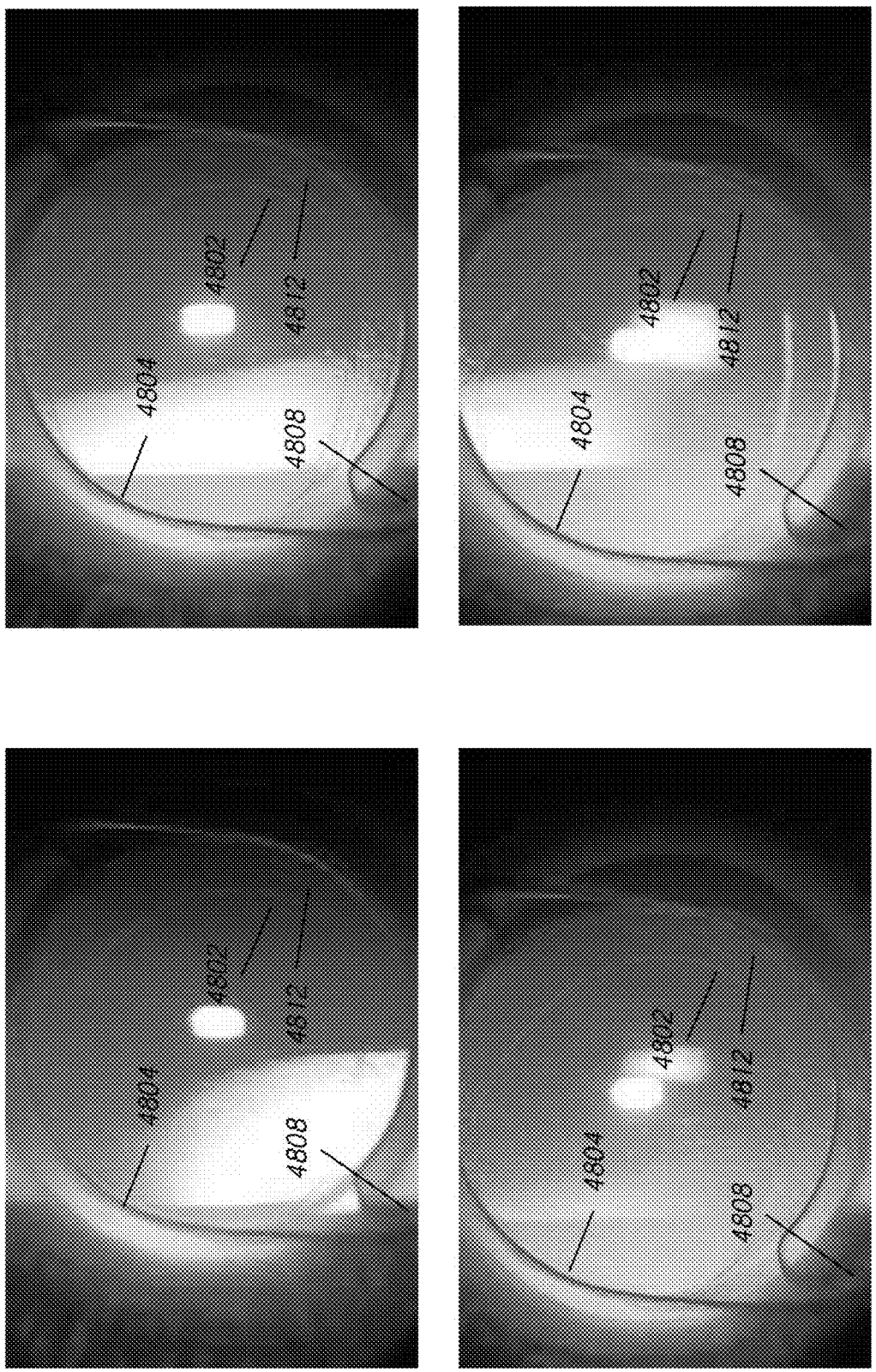

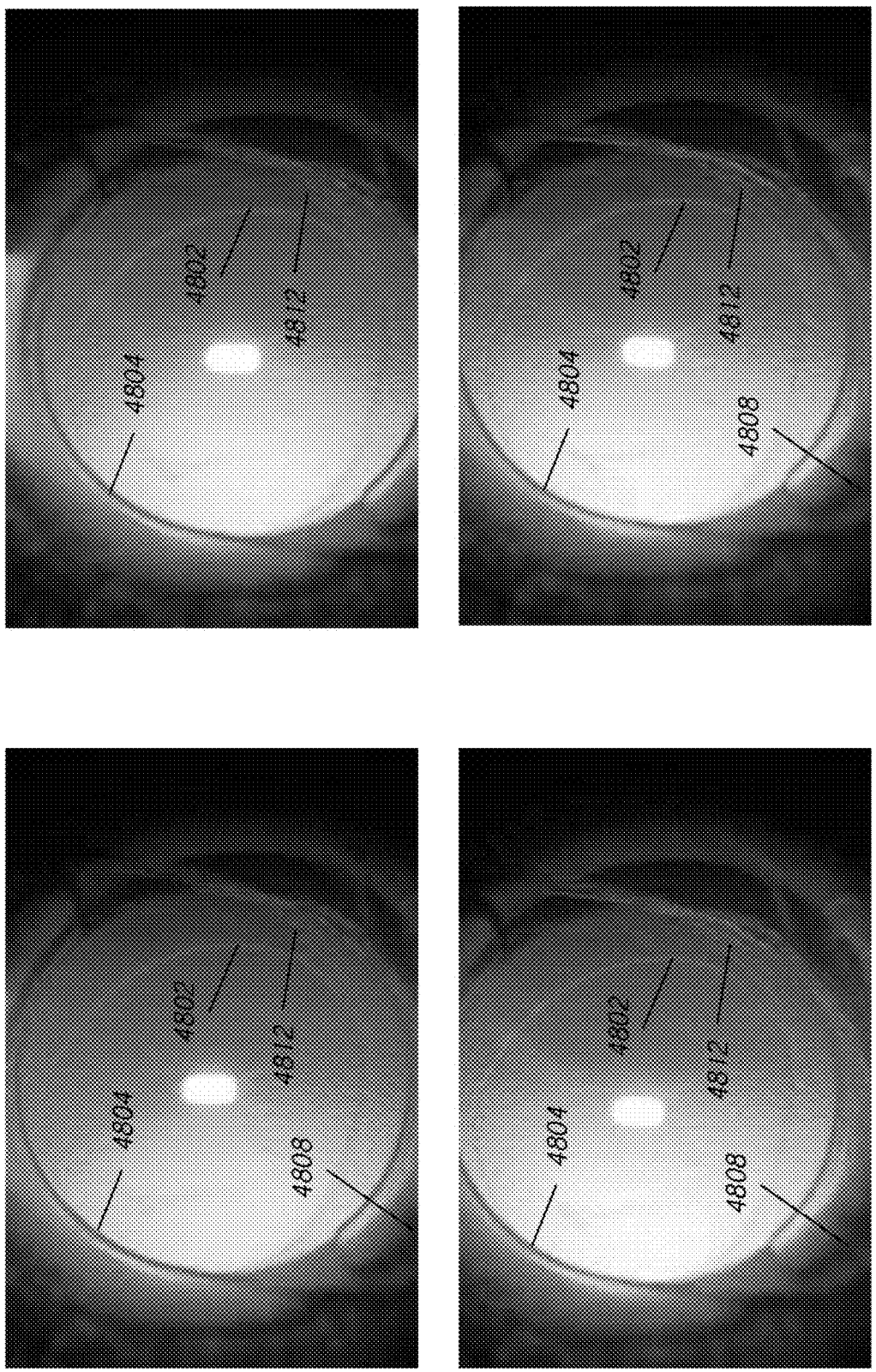

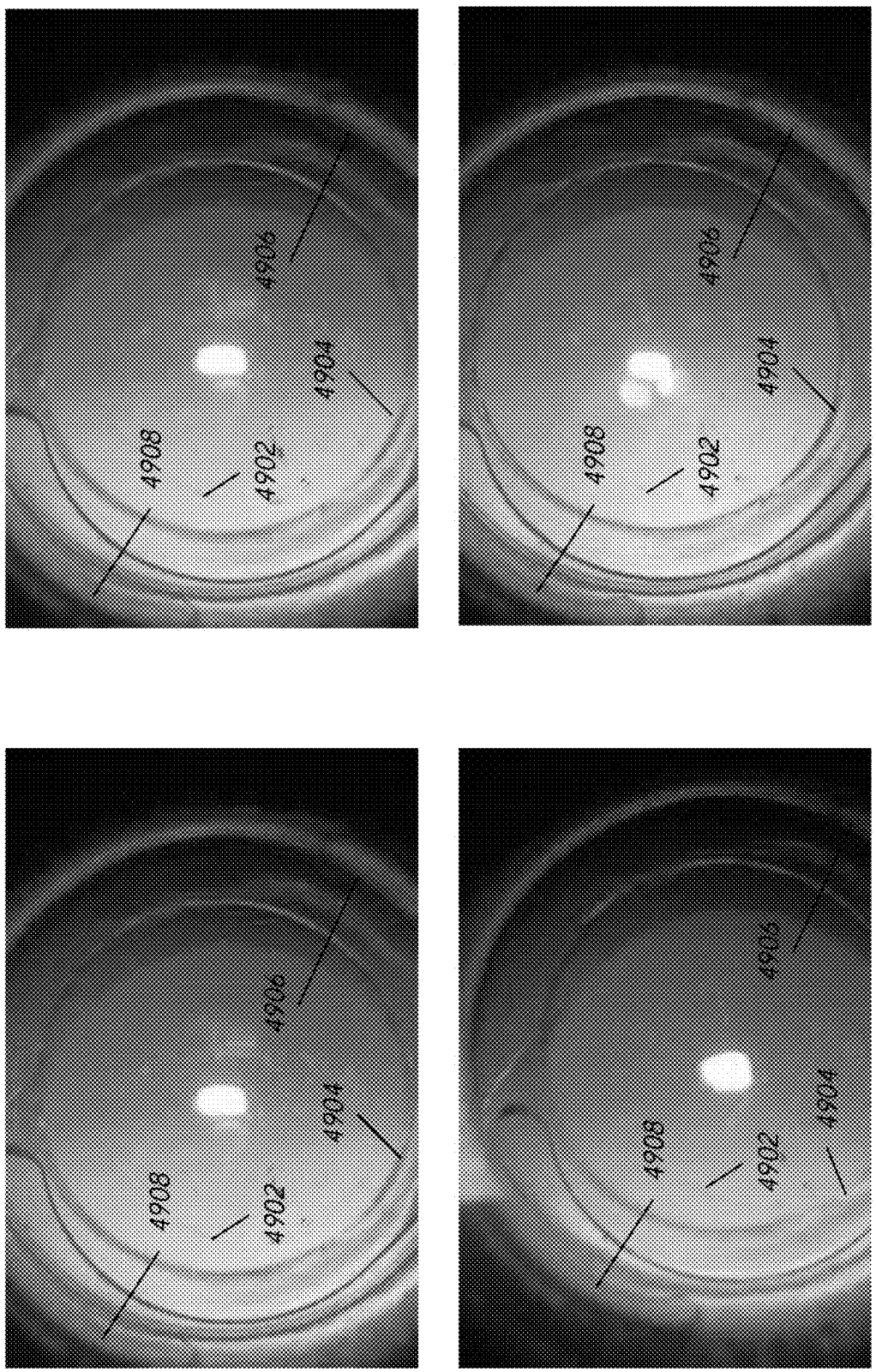

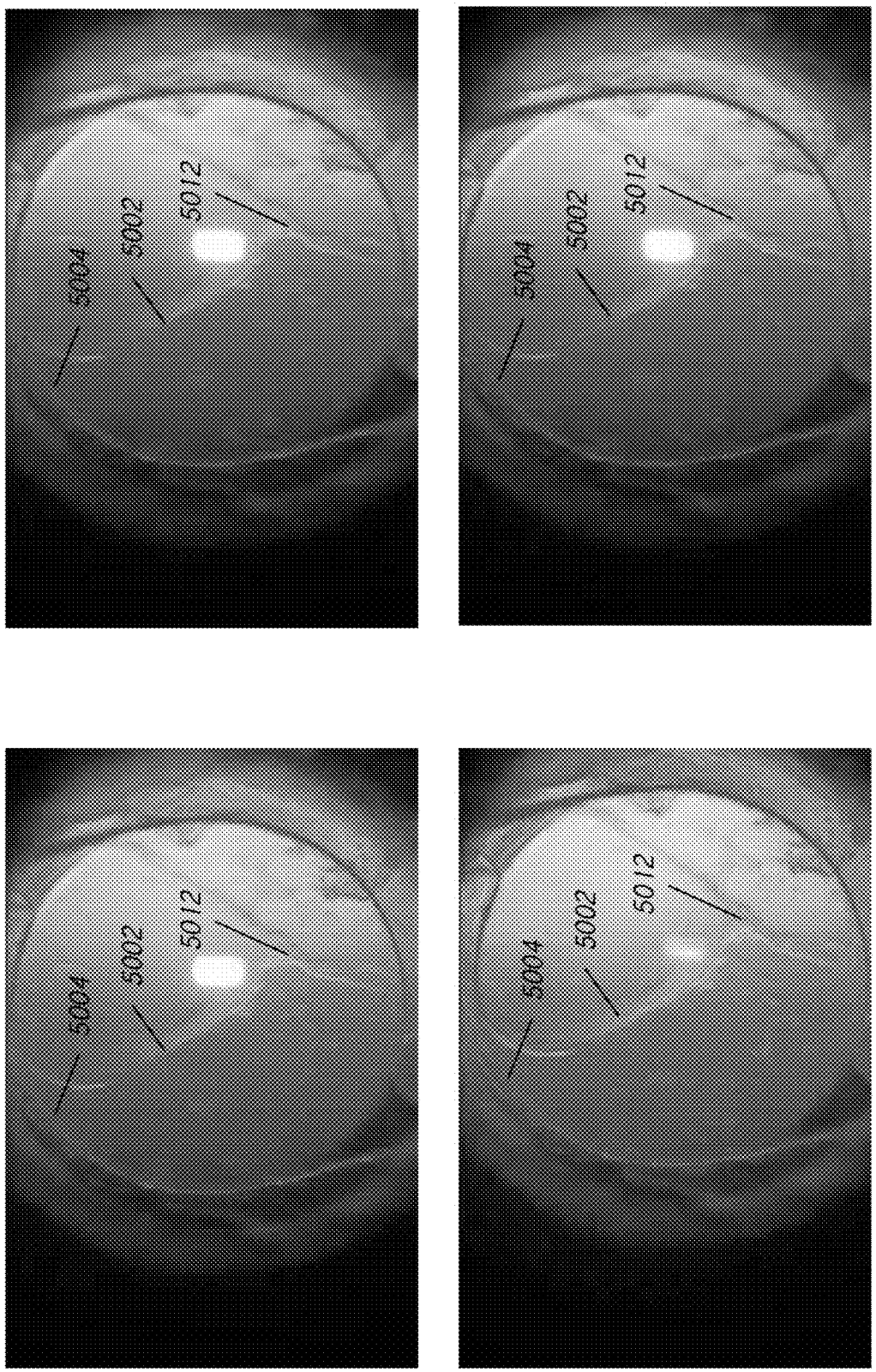

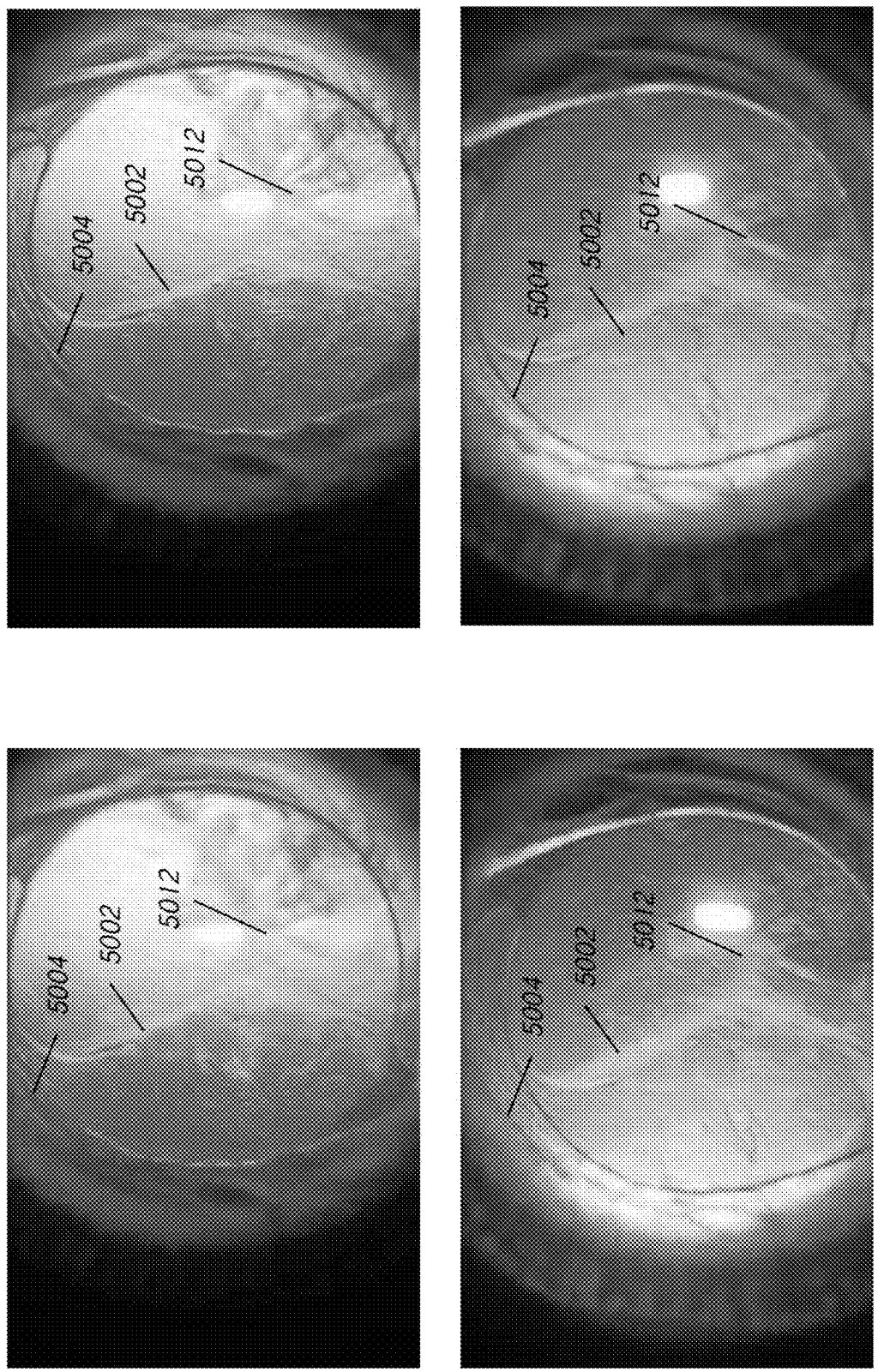

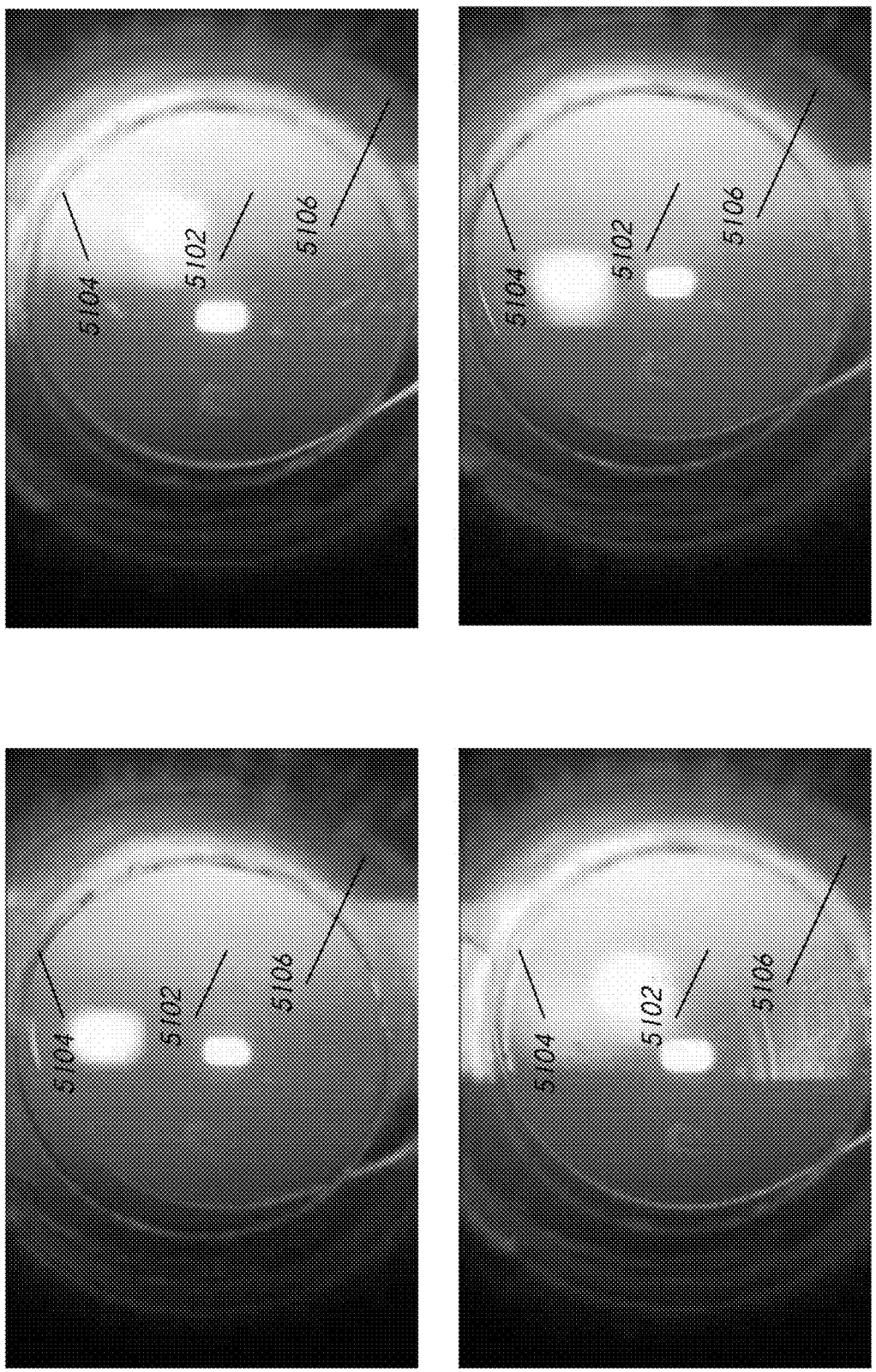

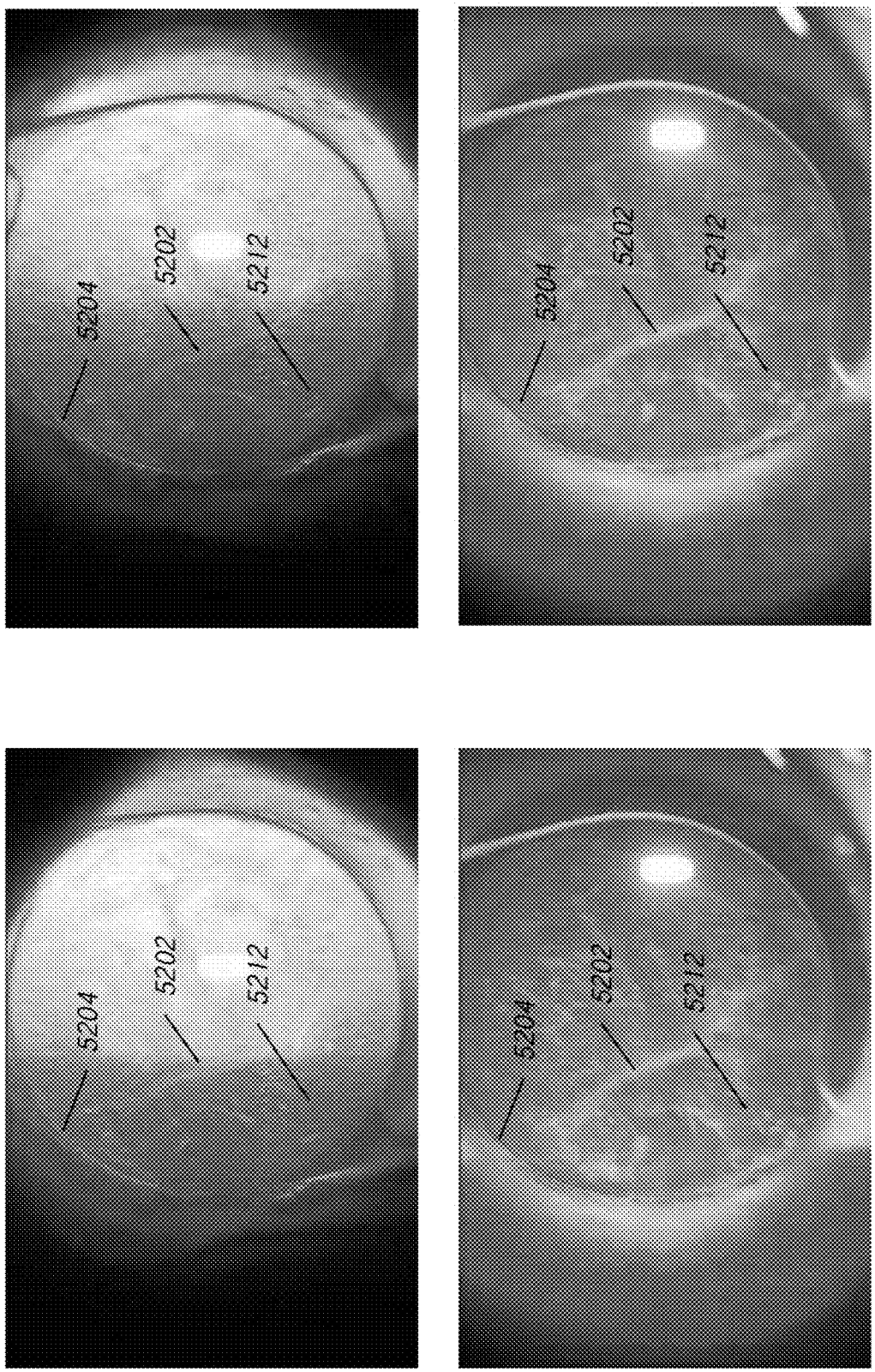

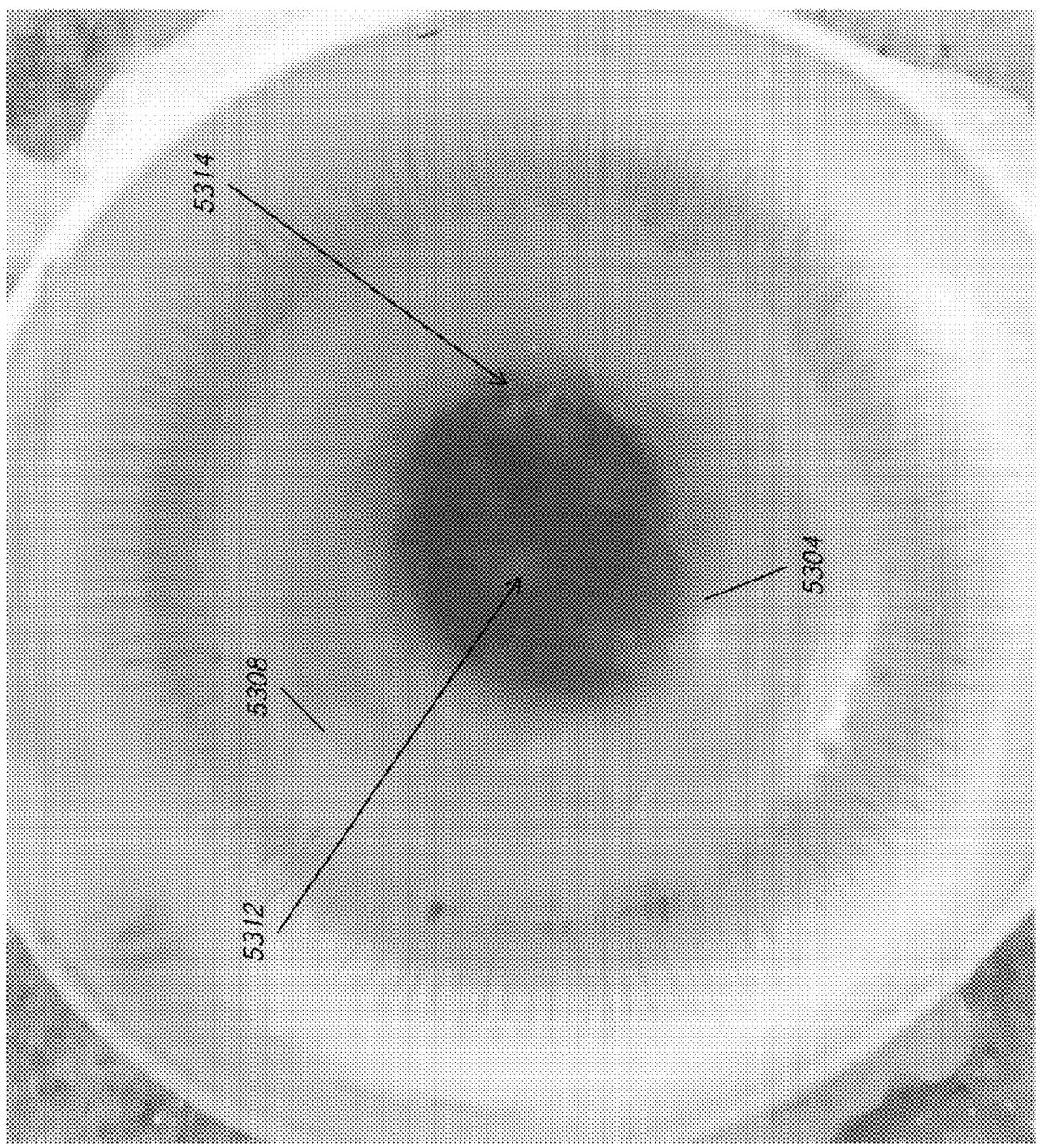

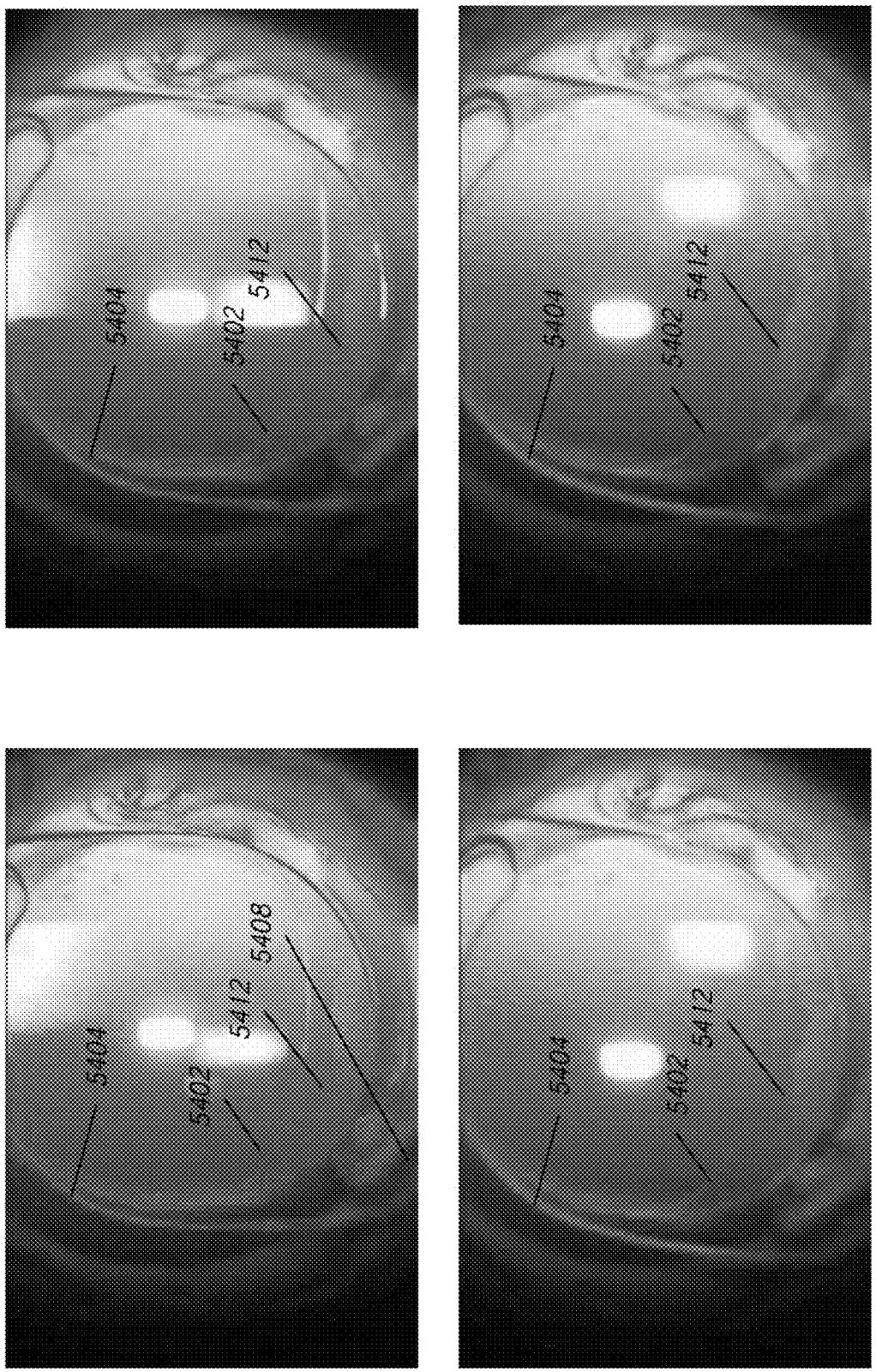

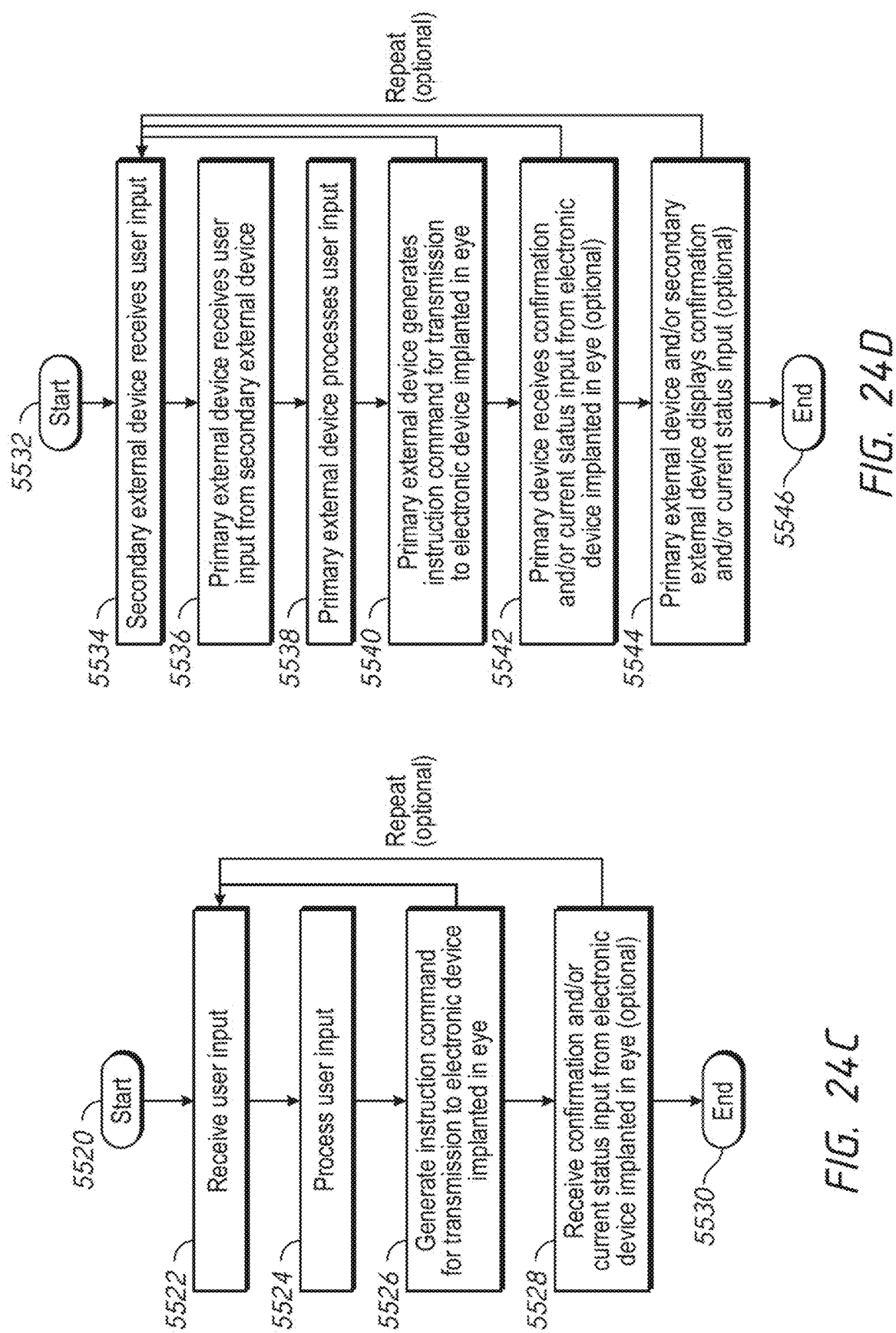

PROSTHETIC CAPSULAR DEVICES, SYSTEMS, AND METHODS

INCORPORATION BY REFERENCE TO ANY PRIORITY APPLICATIONS

This application is a continuation of U.S. patent application Ser. No. 14/742,282, filed Jun. 17, 2015, now U.S. Pat. No. 10,004,594, issued Jun. 26, 2018, which claims priority to U.S. Provisional Patent Application No. 62/014,432, filed Jun. 19, 2014, U.S. Provisional Patent Application No. 62/114,227, filed Feb. 10, 2015, and U.S. Provisional Patent Application No. 62/168,557, filed May 29, 2015, each of which is incorporated herein by reference in its entirety. Any and all applications for which a foreign or domestic priority claim is identified in the Application Data Sheet as filed with the present application are hereby incorporated by reference under 37 C.F.R. § 1.57.

BACKGROUND

Technical Field

The present application relates to prosthetic capsular devices including wearable electronic technology device(s), and methods for insertion into the eye.

Description of the Art

Cataract surgery is one of the most successfully and most frequently performed surgical procedures in the United States. Each year, millions of people achieve a dramatic improvement in their visual function thanks to this procedure. With the increasing proportion of the U.S. population reaching their retirement years, there is expected to be an almost doubling of the demand for cataract surgery over the next twenty years from 3.3 million to over 6 million annually. In response to the increased demand, more ophthalmologists may be trained and certified to perform cataract surgery, and each trained and certified ophthalmologist may perform more cataract surgeries each year.

In addition to the increase in demand for cataract surgery, technological advances have increased patient expectations for the surgery. The procedure takes a short amount of time to perform, and patients expect quick recovery of visual function. Patients are also asking their ophthalmologist to give them the restoration of more youthful vision without glasses through the use multifocal intraocular lenses, presbyopia correcting lenses, tonic lenses, and monovision, to name a few. Despite accurate preoperative measurements and excellent surgical technique, the desired refractive outcome requires a dose of good fortune as there are numerous uncontrolled variables involved. As many as 20-50% of post-operative cataract patients may benefit from glasses or follow-up refractive surgical enhancements to achieve their desired refractive endpoint. The reason for this high amount of refractive unpredictability is believed to be the final resting position of the lens implant in the eye, mathematically expressed as the effective lens position (ELP), which can be quite variable and unpredictable in the current state of cataract surgery. Recently, hundreds of millions of dollars have been invested into developing highly sophisticated femtosecond laser systems that are able to more precisely control the size and shape of the capsulotomy and corneal incisions with the stated goal of lessening the variability of the ELP and thus aiding in better refractive outcomes. Unfortunately, the increased precision of the femtosecond laser systems have not been able to account for the major problem plaguing the variability of the ELP, which is the volumetric difference between the cataract, natural capsular bag, and intraocular lens implant (IOL).

A device and method that helps provide the desired refractive endpoint in cataract surgery is described in PCT Published Patent Application No. WO 2013/126380, Wortz, published on Aug. 29, 2013, which is incorporated herein by reference in its entirety.

All patents and other documents referred to in this application are incorporated by reference herein in their entirety.

SUMMARY

Over the past few years, there has been a major increase in the presence of and reliance on small electronic devices, such as smartphones and related wearable technology, which can provide the user with functions such as internet access, computational ability, computer functionality, e-mail, games, and global positioning system (GPS) function. Some of these devices are being miniaturized and are sometimes worn on the body, such as Google Glass, Microsoft HoloLens, and other head-mounted displays. Additionally, wearable technology that provides biometric data such as blood glucose levels, electrolyte balance, heart rate, electrocardiogram (EKG), intraocular pressure, sensing ciliary muscle contraction for accommodation stimulus, dynamic pupil change, and retinal prostheses have been developed to assist in technology-assisted health care. Such body-mounted devices can be awkward to wear and some users might prefer the positioning of the device in the body. Certain implementations described herein can provide methods and devices for placing a electronic device in the eye.

Certain implementations described herein relate to prosthetic capsular devices (e.g., bags as defined in WO 2013/126380) that can be inserted into an eye. A prosthetic capsular device may comprise an anterior surface including an opening, and a posterior surface. At least a portion of the posterior surface includes or is a refractive surface. The device includes a wearable electronic technology device (e.g., a technology device). The prosthetic capsular device or a system comprising the prosthetic capsular device may include an intraocular lens or features similar to an IOL, such as may be used in cataract surgery to replace the natural lens. The technology device and the intraocular lens may be positioned (e.g., in, around, etc. the prosthetic capsular device) such that the technology device does not interfere with (e.g., block, distort) the sight lines through the intraocular lens.

A retinal prosthesis may be positioned in a prosthetic capsular device, and data collected by the prosthesis may be remotely transmitted to the optic nerve, for example wirelessly. In some implementations in which the retinal prosthesis can function as the end receptor of light, the retinal prosthesis may interfere with (e.g., block, distort) the sight lines through the IOL.

A method for inserting a wearable technology device (e.g., a technology device) into an eye of a patient may comprise surgically removing a lens or cataract from a natural capsule, leaving the natural capsule in an empty state; inserting a prosthetic capsular device into the eye of the patient (e.g., the prosthetic capsular device including an anterior surface having an opening, and a posterior surface, wherein at least a portion of the posterior surface includes or is a refractive surface); and inserting an electronic technology device into the prosthetic capsular device.

An intraocular lens may also be inserted into the prosthetic capsular device, and may be placed in the prosthetic capsular device such that the technology device does not interfere with (e.g., block, distort) sight lines through the intraocular lens, except optionally in the case of a retinal prosthesis.

The methods summarized above and set forth in further detail below may describe certain actions taken by a practitioner; however, it should be understood that these steps can also include the instruction of those actions by another party. Thus, actions such as "inserting an intraocular lens into a prosthetic capsular device" include "instructing the insertion of an intraocular lens into a prosthetic capsular device."

BRIEF DESCRIPTION OF THE DRAWINGS

A better understanding of the devices and methods described herein will be appreciated upon reference to the following description in conjunction with the accompanying drawings, wherein:

FIG. 1 depicts a cross-sectional side view of an eye including an example of a prosthetic capsular device including an IOL;

FIG. 2 depicts a side view of the example prosthetic capsular device shown in FIG. 1;

FIG. 12A depicts a cross-sectional view of an eye including an example prosthetic capsular device containing including both a technology device and an IOL;

FIG. 12B depicts a front view of an example intraocular lens usable in the example prosthetic capsular device shown in FIG. 12A in which the technology device surrounds the outer edge of the IOL (e.g., surrounds the outer edge of the optical surface of the IOL);

FIG. 12C depicts a top front perspective of the example intraocular lens of FIG. 12B;

FIGS. 14A-14E are photographs of animal study results for a right eye of a first rabbit;

FIGS. 15A-15E are photographs of animal study results for a left eye of the first rabbit;

FIGS. 16A-16E are photographs of animal study results for a right eye of a second rabbit;

FIGS. 17A-17E are photographs of animal study results for a left eye of the second rabbit;

FIGS. 18A-18E are photographs of animal study results for a right eye of a third rabbit;

FIGS. 19A-19E are photographs of animal study results for a left eye of the third rabbit;

FIGS. 20A-20E are photographs of animal study results for a right eye of a fourth rabbit;

FIGS. 21A-21E are photographs of animal study results for a left eye of the fourth rabbit;

FIGS. 22A-22E are photographs of animal study results for a right eye of a fifth rabbit;

FIGS. 23A-23E are photographs of animal study results for a left eye of the fifth rabbit;

FIG. 24C is a flowchart of an example of controlling an electronic device using an external device;

FIG. 24D is a flowchart of another example of controlling an electronic device using an external device;

The patent or application file contains at least one drawing executed in color. Copies of this patent or patent application publication with color drawing(s) will be provided by the Office upon request and payment of the necessary fee.

DETAILED DESCRIPTION

Some prosthetic capsular enclosure devices (e.g., prosthetic capsular bags) that can be used in the eye can hold at least one of a technology device (e.g., an electronic technology device (e.g., a wearable electronic technology device (e.g., a miniaturized wearable electronic technology device))) and an intraocular lens.

Examples of preferred prosthetic capsular devices that may be compatible with certain implementations described herein are disclosed in PCT Published Patent Application No. WO 2013/126380, which is incorporated herein by reference in its entirety. Some preferred prosthetic capsular devices are described herein.

Figure 3:
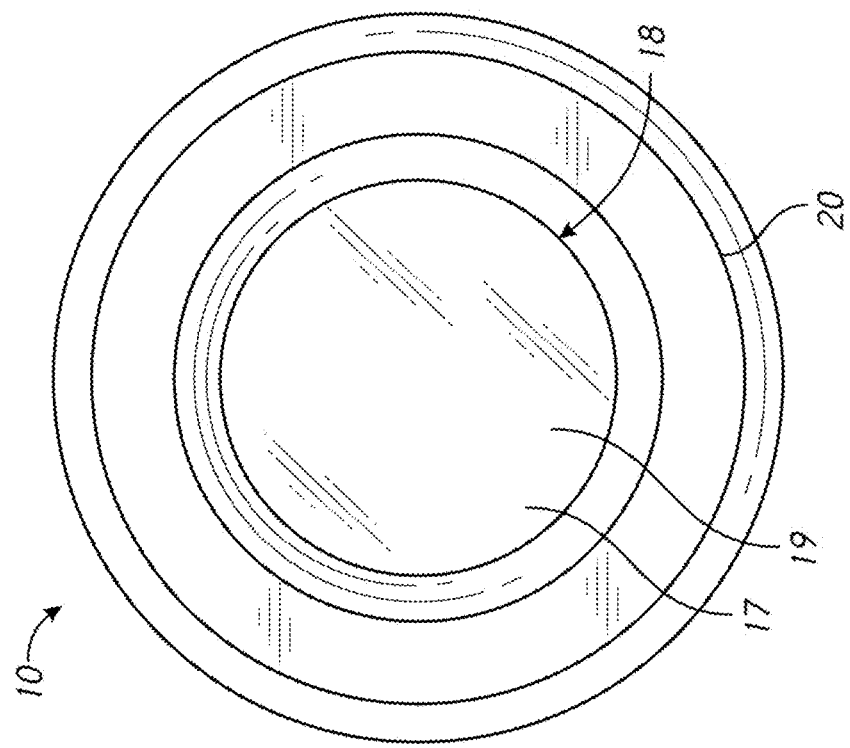
FIG. 3 depicts an anterior plan view of the example prosthetic capsular device shown in FIG. 1.

With reference to FIGS. 1-3, a prosthetic capsular device or PPL-C 10 is shown approximating the size, shape, and volume of a natural human lens. The dimensions of the prosthetic capsular device 10 may be variable, so that physicians may order an implant that most closely matches the lens of the eye 12 being operated on. The human lens varies in thickness from about 3.5 millimeters (mm) to about 5.5 mm. A natural lens tends to be thicker in more hyperopic eyes and thinner in more myopic eyes. A natural lens thickens over time, and increased age is associated with a thicker lens on average. The diameter of the human lens is about 9 mm. In some implementations, the prosthetic capsular device 10 comprises a substantially discoid (e.g., a substantially flat, substantially circular disc) and/or spheroid (e.g., prolate spheroid, oblate spheroid) shape having a thickness between about 1.5 mm and about 5.5 mm (e.g., about 2.5 mm) and a diameter between about 8.5 mm and about 10 mm (e.g., about 9 mm). For purposes of clarity, the thickness of the prosthetic capsular device 10 is the distance between the anterior surface 14 and posterior surface 16 of the prosthetic capsular device 10 along the visual axis 15 (FIG. 2), for example in contrast with the thickness of walls of the device 10. The anterior surface 14 includes an arcuate (e.g., circular, oval) opening 18 having a diameter between about 5 mm and about 7 mm (e.g., about 6 mm), and has an exterior contour, such as, for example, a flange 20 (e.g., having a thickness between about 0.5 mm and about 1.5 mm (e.g., about 1 mm), substantially surrounding (e.g., surrounding) and extending radially outwardly from the opening 18. The flange 20 can assist in stabilization and/or centration of the prosthetic capsular device 10 by extending into and fitting in the ciliary sulcus 22 (FIG. 1). The flange 20 may lack or be substantially free of perforations, which may increase stability and apposition surface area of the flange 20. The prosthetic capsular device 10 may be dimensioned to fit precisely in a capsulorhexis created by a femtosecond laser.

At least a portion of the inner face or side 17 of the posterior surface or portion 16 of the prosthetic capsular device 10 may comprise a refractive surface, which may, for example, allow a pseudophakic refraction to be performed intraoperatively with a known lens already inside the eye 12, e.g., the posterior refractive surface 19. In the implementation shown in FIGS. 1-3, substantially the entire inner face 17 comprises a low power refractive surface (e.g., about +1 diopter (D)). While the posterior refractive surface 19 is generally discussed herein in terms of a +1 D surface, the posterior refractive surface 19 may comprise any and all lens powers and designs that are currently known in the art of intraocular lenses, including, but not limited to: spherical, aspheric, wavefront, convex, concave, multifocal (diffractive, refractive, zonal), toric, accommodative, ultraviolet (UV) filtering, and diffractive chromatic aberration reducing lenses, and optical powers ranging from any positive diopter value (e.g., including +35 D and above) to any negative diopter value (e.g., including −35 D and below).

The posterior refractive surface 19 may advantageously reduce the refractive power of the IOL to be placed in the device 10. For example, if the device did not include a posterior surface (e.g., comprised a simple or modified ring), then one or more IOL devices would provide all of the refractive power, which could increase the volume of the IOL, leading to a larger incision and associated complications. A posterior refractive surface implanted in the eye can advantageously allow for a second refractive device to be coupled with (e.g., placed within, next to, and/or on top of) the posterior refractive surface. The posterior refractive surface 19 can allow the ELP of the eye to be determined along with any residual refractive error. If any further refractive error is discovered, a second refractive device can be added to the posterior refractive surface 19 (e.g., immediately), which can neutralize the deficit and help ensure that the desired outcome is achieved. The posterior refractive surface 19 being integrally formed with the remainder of the device 10, which can be accurately placed and anchored, can inhibit or prevent shifting of lateral and/or posterior-anterior position, rotation, tilt, etc. of the posterior refractive surface 19 that could lead to degradation of vision. The continuous nature of the device 10 on all sides except for the anterior opening 18 can inhibit, reduce, or prevent ingrowth of lens epithelial cells, and thereby can inhibit or prevent formation of intra-lenticular opacifications.

The device 10 comprising a refractive surface 19, rather than being a through hole of an annulus, for example, can reduce the volume of an IOL inserted therein, which may advantageously reduce incision size. The posterior refractive surface 19 may provide protection for the natural capsular bag 24 during placement of an IOL. For example, the IOL is inhibited or prevented from directly contacting the natural capsular bag 24 because the IOL instead contacts the device 10. For another example, vitreous is inhibited or prevented from contacting the IOL. Sidewalls of the device 10 that do not include apertures large enough for a portion (e.g., a haptic) of an IOL to prolapse through may provide protection for the natural capsular bag 24 during placement of an IOL, for example because the IOL is inhibited or prevented from directly contacting the natural capsular bag 24.

The prosthetic capsular device 10 is adapted to be implanted in the eye 12. The prosthetic capsular device 10 preferably comprises a biologically-compatible material that would be inserted inside the eye 12. The prosthetic capsular device 10 is preferably deformable so as to be folded and inserted via an injection system through a corneal incision ranging between about 0.1 mm and about 10 mm, preferably between about 1.5 mm and about 3 mm. The size of the corneal incision varies based on several factors, including, for example, the volume of the prosthetic capsular device 10, the plasticity of the prosthetic capsular device 10, the volume of the injection cartridge through which the prosthetic capsular device 10 will be delivered, frictional forces, combinations thereof, and the like. The capsulorhexis is preferably between about 4 mm and about 7 mm (e.g., about 6 mm), although, if a femtosecond laser is used, the capsulorhexis should be less than the dilated diameter of the patient's pupil, as a femtosecond laser generally cannot create a capsulotomy through the iris. A capsulorhexis created manually may be about the same size as a capsulorhexis created by a femtosecond laser, as direct visualization of the rhexis boundary is advisable throughout the creation process. The capsulorhexis ranges between about 3 mm and about 8 mm, preferably between about 4 mm and about 7 mm. During implantation, the folded prosthetic capsular device 10 passes through the corneal incision, through the capsulorhexis, and into the patient's natural capsular bag 24 (FIG. 1). The natural capsular bag 24 may be fully, partially, or not intact, or is missing or a remnant, although it is preferred to place the device 10 in an intact natural capsular bag 24 other than the continuous curvilinear capsulorhexis, devoid of natural lens material, with intact zonules. If the natural capsular bag 24 is not sufficiently intact, alternative techniques may be employed, for example to secure the device 10 to the posterior chamber (e.g., suturing the device 10 to the scleral wall). The prosthetic capsular device 10 preferably possesses sufficient elasticity to resume its pre-folded shape, for example by self-expanding, once positioned inside the eye 12. Intraocular lenses comprising materials including silicone, polyimide, collamer, and acrylic can have one or more of these capabilities. In some implementations, the prosthetic capsular device 10 comprises a biologically-compatible, optically clear material similar or identical to those used in foldable intraocular lenses.

The prosthetic capsular device 10 is preferably inserted in the natural capsular bag 24 of the eye 12 of a patient through the use of an injection system. The injection system can allow the prosthetic capsular device 10 to be folded or automatically folded into a smaller shape as the prosthetic capsular device 10 is advanced through the injection system so as to allow the prosthetic capsular device 10 to fit through an incision much smaller than the diameter of the unfolded prosthetic capsular device 10. Injection systems through which IOLs are injected into the eye, for example comprising a cylindrical cartridge and an advancement rod on a screw type advancement system or plunger advancement system, would be suitable for use with the prosthetic capsular device 10. Other injection systems are also possible.

The prosthetic capsular device 10 is preferably inserted in a natural capsular bag 24 of the eye 12 of a patient who has had cataract surgery with the use of a laser (e.g., a femtosecond laser) to create a capsulorhexis, although insertion into natural capsular bag 24 after manual creation of the capsulorhexis is also possible. A femtosecond laser may be used to create the capsulorhexis, for example after the same femtosecond laser or a different femtosecond laser or a different device was used to make the other incisions including the main wound, the paracentesis, and any corneal or limbal relaxing incisions. The patient's natural lens, for example clouded by a cataract such that it may be itself termed a "cataract," may be removed using techniques known in the art. For example, the natural lens material may be broken up and vacuumed out, leaving the natural capsular bag 24 partially, fully, or not intact, or being missing or a remnant. The residual cortex may be removed using techniques known in the art such as via irrigation/aspiration. An aphakic refraction may be completed using an intraocular refracting device such as, for example, the ORA System, available from WaveTec of Aliso Viejo, Calif. An IOL calculation may be performed using an algorithm such as, for example, the Mackool algorithm. The patient's natural capsular bag 24 and anterior segment 26 may be inflated with a viscoelastic material, such as sodium hyaluronate (e.g., Provisc, Healon, Viscoat). The prosthetic capsular device 10 may be loaded into an injection device, for example by being folded into a small tubular shape, and injected into the natural capsular bag 24. The viscoelastic material may be removed from behind the prosthetic capsular device 10 and from the anterior segment 26. A pseudophakic refraction may be performed with a system similar to a standard auto-refractor or the intraoperative WaveTec ORA System. This calculation is preferably performed using approved protocols. An intraoperative Optical Coherence Tomography system, such as the Zeiss OPMI Lumera 700 with ReScan 700, could be used to measure the exact position of the prosthetic capsular device 10 in the eye 12, relative to the cornea and the retina. Along with preoperative measurements of the cornea and axial length, the position of prosthetic capsular device 10 as determined by the OCT measurement could allow the surgeon to determine the power of a lens that would provide the desired refraction using a vergence formula.

An example refraction using an approved protocol, and accompanying background information, is discussed herein. Current state of the art requires multiple independent variables to be measured so that the dependent variable of effective lens position can be estimated. The seven independent variables in the Holladay 2 formula (one of the most popular modern formulas) are, in decreasing order of importance: (1) axial length, (2) average keratometric power, (3) horizontal white to white, (4) refraction, (5) anterior segment depth, (6) lens thickness, and (7) age. These variables are then used to estimate the Effective Lens Position. However, this position is simply an estimation or prediction. If the estimation or prediction of the positon is incorrect, the post-operative refractive outcome will be compromised. Therefore, emphasis should be placed on the ability to determine the ELP rather than estimating the ELP. The prosthetic capsular device 10 can help determine the ELP in one, two, or more different ways, as described herein.

Figure 4A:
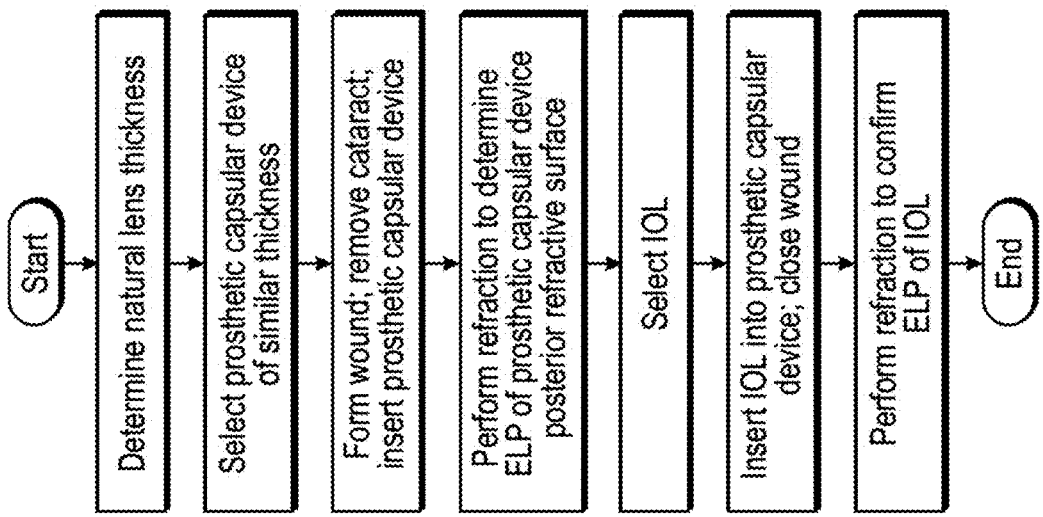
FIG. 4A is a flow chart of an example method for inserting and positioning a prosthetic capsular device into an eye.

FIG. 4A is a flow chart of an example method for inserting and positioning a prosthetic capsular device 10 into a patient's eye 12, with continued reference to FIGS. 1-3. First, the lens thickness of a patient's natural lens is determined preoperatively using known techniques. Next, a prosthetic capsular device 10 having a thickness similar to the thickness of the patient's natural lens is selected. Selection of a prosthetic capsular device 10 sized such that the inner face 17 of the prosthetic capsular device 10 is at the same location as the posterior surface of the patient's natural lens is preferred such that, when an IOL 28 is inserted in the prosthetic capsular device 10, that IOL 28 will be positioned in substantially the identical location previously occupied by the patient's natural lens. Although the natural capsular bag 24 remains open, a combination of very thin lenses may be used such that lenses may be positioned slightly differently than the natural lens as measured from cornea to lens surface or back surface to retina. The prosthetic lens of ideal power can be appropriately identified and inserted in the eye 12 to provide the desired refractive endpoint.

A femtosecond laser and/or manual keratome may be used to form the main wound, the paracentesis, any corneal or limbal relaxing incisions. The femtosecond laser and/or manual technique may be used to create the capsulorhexis. The patient's natural lens or cataract is then removed using techniques known in the art. The residual cortex is removed using techniques known in the art, such as via irrigation/aspiration. Then, the patient's natural capsular bag 24 and anterior segment 26 are filled with viscoelastic material, and the prosthetic capsular device 10 is inserted into the natural capsular bag 24. The viscoelastic material is then removed from behind the prosthetic capsular device 10 and from the anterior segment 26 in preparation for performing a pseudophakic refraction.

By being able to identify and control the position of the IOL 28, choosing an IOL 28 may be independent of the seven variables used for ELP in the Holladay 2 formula. Rather, via theoretical vergence formulas, the exact IOL 28 that can provide a desired refractive outcome can be specifically calculated using keratometric power, effective lens position, and axial length. The weakness of the formulas currently used is the inability to accurately estimate or predict ELP. To confirm that the pre-operative theoretical calculation is correct, a refraction may be performed in the operating room once the prosthetic capsular device 10 is implanted in the patient's eye via a WaveTec ORA System, retinoscopy, or by other known methods. The refraction will technically be a pseudophakic refraction, as the posterior refractive surface 19 of the prosthetic capsular device 10 has a refractive power, such as, for example, +1 diopter.

A method to determine the correct intraocular power for a piggyback lens may be calculated by first determining the power of the IOL 28 to be implanted using Equation 1:

$$IOLe = \frac{1336}{\frac{1336}{\frac{1000}{\frac{1000}{PreRx} - V} + Ko} - ELPo} - \frac{1336}{\frac{1336}{\frac{1000}{\frac{1000}{DPostRx} - V} + Ko} - ELPo} \quad (Eq.\ 1)$$

wherein: IOLe=IOL power; ELPo=effective lens position; Ko=net corneal power; V=vertex distance; PreRx=pre-op refraction (also can represent the intra-operative refraction after the prosthetic capsular device has been placed); and DPostRx=desired post-operative refraction.

The Effective Lens Position (ELP or ELPo) is the distance from the secondary principal plane of the cornea to the principal plane of the thin-IOL equivalent. The keratometric power of the cornea (Kk) can be converted to the net optical power of the cornea (Ko) using Equation 2:

$$Ko = Kk * 0.98765431 \quad (Eq.\ 2)$$

For example, if the Kk is 44.50 D, Ko=44.50 D*0.98765431=43.95 D. The net optical power of the cornea would then be 43.95 D.

By comparing the pre-operative theoretical IOL calculations with the aphakic refraction, the prosthetic capsular device refraction, and the post-IOL implantation refraction, surgeons can greatly improve the accuracy of their post-operative refractive outcomes.

Still referring to FIG. 4A, once the appropriate IOL 28 is selected, the prosthetic capsular device 10 and anterior segment 26 are refilled with viscoelastic material and, based on the residual refractive error, the appropriate IOL 28 is selected and inserted into the prosthetic capsular device 10. The viscoelastic material is then removed from the eye 12, and the wounds are closed through standard methods such as hydration, suturing, etc. A final confirmatory refraction may be completed while ensuring normal intraocular pressure, which can affect the position of the prosthetic capsular device 10 and IOL 28 inside the eye 12. If significant error was found at this point, the surgeon may remove the implanted IOL and replace the implanted IOL with a more desirable IOL (e.g., having a more desirable refractive power), substantially without risking damage to the fragile natural capsular bag 24, due to the protective nature of having the IOL 28 contained in the prosthetic capsular device 10. The ability provided by the natural capsular device 10 to remove and insert IOLs is described further herein.

The device 10 may be used as a stand-alone intraocular lens for the primary correction of aphakia. A device 10 including a particular lens may be chosen based on pre-operative measurements and/or theoretical formulae. Intra-operative aberrometry could also be used in the aphakic mode to help aid in the selection of the device 10 including its lens or posterior refractive surface 19. While this technique and implementation does not necessarily take advantage of the improvement of ELP prediction and identification, use the device 10 as a stand alone intraocular lens, with the ability to contain other technology of various types for implantation in the future, is a reasonable solution.

The following method or surgical procedure for implanting a prosthetic capsular device as described herein has been successfully used in animal studies using three New Zealand white rabbits of same sex and weighing between 2.4 kg and 3.2 kg and in animal studies using five New Zealand white rabbits of same sex and weighing between 3.2 kg and 3.6 kg. The animals were quarantined for at least seven days and grossly checked for the presence of any anomalies prior to the beginning of the procedure. Each animal was prepared for surgery by pupil dilation with 1% cyclopentolate hydrochloride and 2.5% phenylephrine drops, applied topically three times each spaced by a duration of five minutes. Anesthesia was obtained with an intramuscular injection of ketamine hydrochloride (50 mg/kg) and xylazine (7 mg/Kg) in a mixture of 7:1, respectively. One drop of topical proparacaine hydrochloride anesthetic was also placed in each eye prior to beginning surgery. Eye movement and animal respiration were monitored intraoperatively to ensure that adequate levels of anesthesia were maintained. Supplemental anesthetics were given intramuscularly as needed during the operation. The area around the eye was draped in an aseptic manner. A lid speculum was placed to retract the lids. One drop of povidone-iodine (PVP-I) 5% and a drop of antibiotic was placed on the surface of the eye just before beginning surgery. Using aseptic technique and a Zeiss surgical microscope, a fornix-based conjunctival flap was fashioned. A corneal-scleral incision was made using a crescent blade, and an initial 3.0 mm limbal incision was made using a 3.0 mm keratome to enter the anterior chamber. Capsulorhexis forceps were used to create a well centered continuous curvilinear capsulotomy (CCC), with a diameter between about 5.0 mm and about 5.5 mm.

After hydrodissection, a phacoemulsification handpiece (Alcon Infiniti system) was inserted into the posterior chamber for removal of lens nucleus and cortical material. One milliliter (mL) of epinephrine 1:1000 and 0.5 mL of heparin (10,000 USP units/mL) were added to each 500 mL of irrigation solution to facilitate pupil dilation and control inflammation. The endocapsular technique was used with the phacoemulsification to take place entirely within the natural capsular bag. The residual cortex was then removed with the irrigation/aspiration (I/A) handpiece. After removal of the natural lens, an ophthalmic viscosurgical device (OVD) (Amvisc Plus, Bausch & Lomb) was used to inflate the natural capsular bag.

Figure 4D:
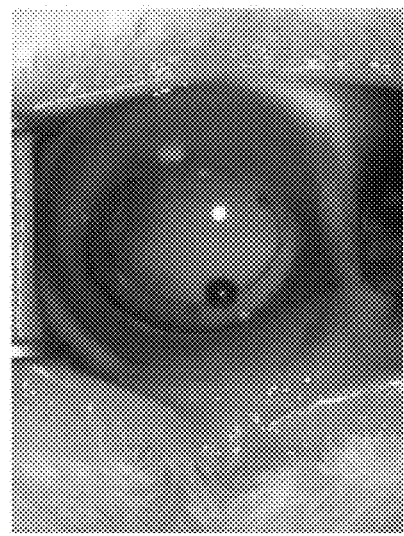
FIGS. 4B-4G are photos of an example method for inserting and positioning a prosthetic capsular device into an eye.
Figure 4C:
Figure 4B:
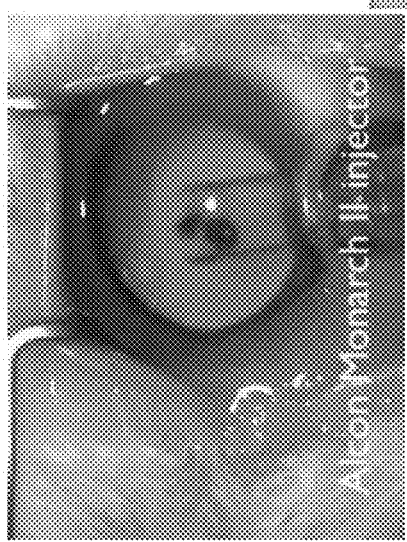

As shown in FIGS. 4B-4D, the prosthetic capsular bag was then injected by using an appropriate injector system ("A" cartridge and Monarch II injector from Alcon Laboratories; Accuject 2.2-1P injector set from Medicel), after the surgeon slightly increased the incision size. Loading of the prosthetic capsular device into the injectors was found to be uneventful. If the prosthetic capsular device was injected partially out of the natural capsular bag (e.g., due to fibrin formation, papillary restriction, injector limitation, etc.), the prosthetic capsular device was able to be manipulated with a collar button hook to complete in-the-bag fixation. Careful control of the injector may inhibit or prevent rapid or uncontrolled release of the prosthetic capsular device from the injector. Even when the plunger of an injector overrode the prosthetic capsular device inside the plunger, injection in the natural capsular bag was possible.

Figure 4G:
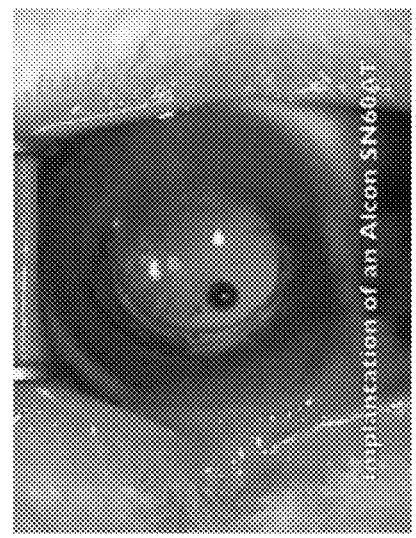
Figure 4F:
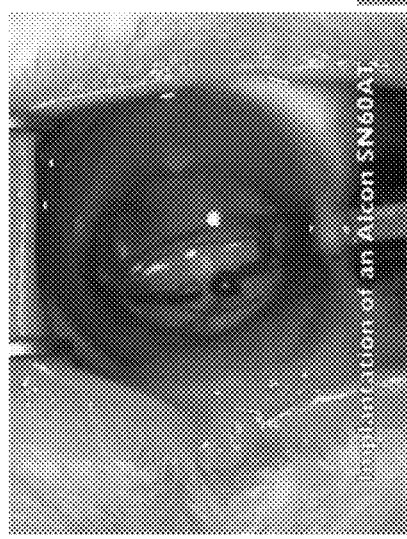
Figure 4E:
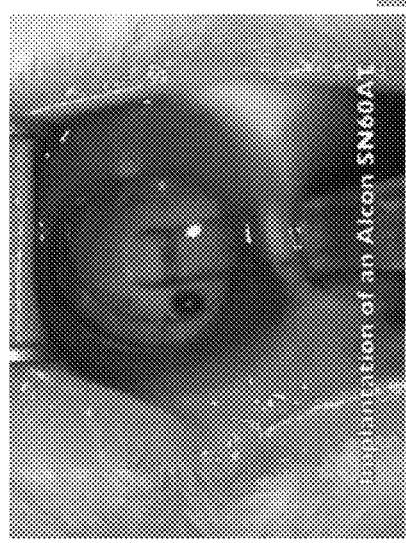

As shown in FIGS. 4E-4G, this was followed by insertion of IOLs (AcrySof SN60AT, a single-piece hydrophobic acrylic IOL manufactured by Alcon) using the Monarch II injector and "C" cartridges. The AcrySof lens was fully fixated within the prosthetic capsular device in all instances, uneventfully. The device and IOL were carefully inspected under high magnification for any possible damage that might have occurred during the loading/implantation process. Centration of the prosthetic capsular device and of the IOL inside of the prosthetic capsular device was found to be excellent in all cases. In three eyes, the natural capsular bag containing the prosthetic capsular device and the AcrySof lens was slightly oval.

Combination antibiotics/steroid ointment (neomycin and polymyxin B sulfates, and dexamethasone) was applied to the eyes following surgery. The same ointment was placed in the eyes four times per day for the first postoperative week. Ointment was discontinued after one week. In the second postoperative week, each animal received topical prednisolone acetate drops four times per day. In the third postoperative week, each animal received topical prednisolone acetate drops two times per day, with discontinuation of the drops following the third postoperative week.

The eyes were evaluated grossly at day one, and by slit lamp examination with scoring for ocular inflammatory response at one, two, three, and four weeks postoperatively (±2 days) and photographs were taken (see below). At each of these examinations, the rabbit eyes were dilated using a combination of cyclopentolate hydrochloride solution and phenylephrine. A standard scoring method in eleven specific categories was used at each examination, including assessment of corneal edema, as well as the presence of cell and flare within the anterior chamber. Retro-illumination images with the pupil fully dilated were obtained for the purpose of photographic documentation regarding CCC size, anterior capsule opacification (ACO), posterior capsule opacification (PCO), and any observed capsular fibrosis at the discretion of the study directors. The images are provided and discussed in further detail herein.

After the clinical examination at four weeks, the animals were anesthetized using a 1 to 2 cm$^3$ (cc) intramuscular injection of a 7:1 mixture of ketamine hydrochloride and xylazine, and then humanely euthanized with a 1 mL intravenous injection of pentobarbital sodium/phenytoin sodium. The globes were enucleated and placed in 10% neutral buffered formalin. The globes were then bisected coronally just anterior to the equator. Gross examination and photographs from the posterior aspect (Miyake-Apple view) were performed to assess the ACO and PCO development, as well as IOL fixation. The extent and severity of ACO and PCO were scored according to established methods.

After gross examination and photographs, all globes were sectioned and the anterior segments including the capsular bags were processed for standard light microscopy and stained with hematoxylin and eosin (H & E). Features such as cell type, extent and route of growth, etc. were documented by serial photomicrographs.

Figure 4H:
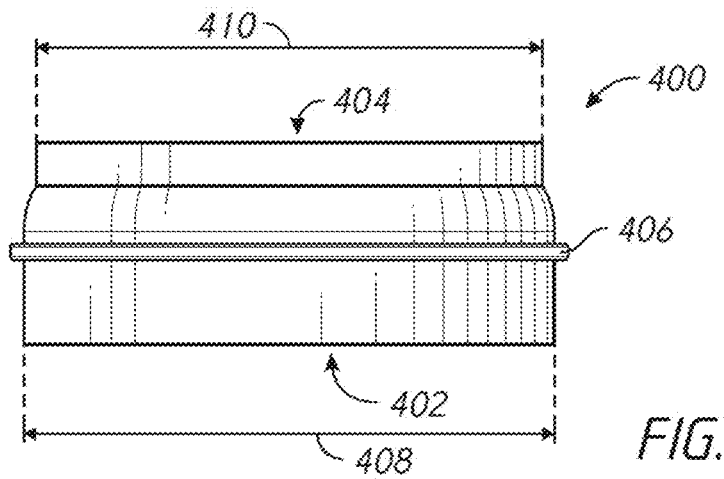
FIG. 4H is a side view of an example prosthetic capsular device.
Figure 4I:
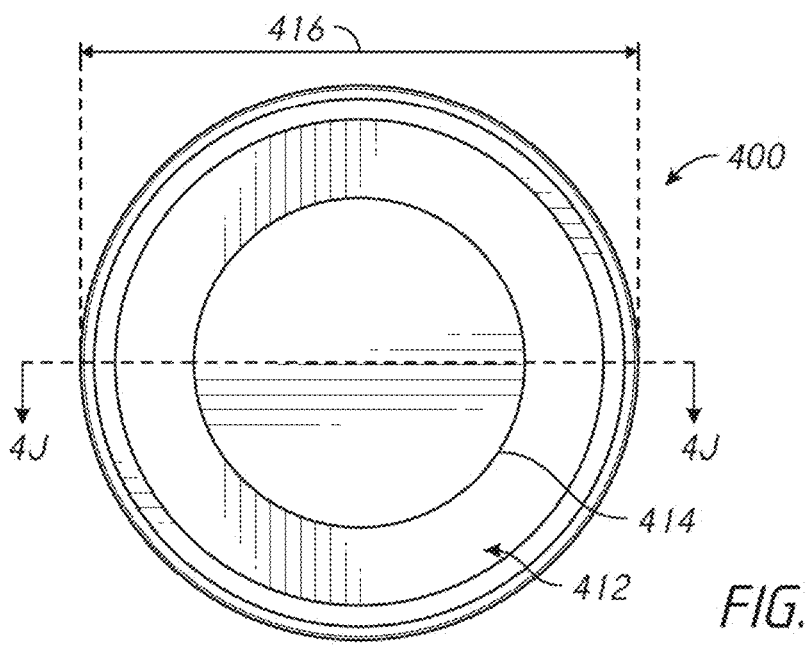
FIG. 4I is an anterior view of the prosthetic capsular device of FIG. 4H.
Figure 4J:
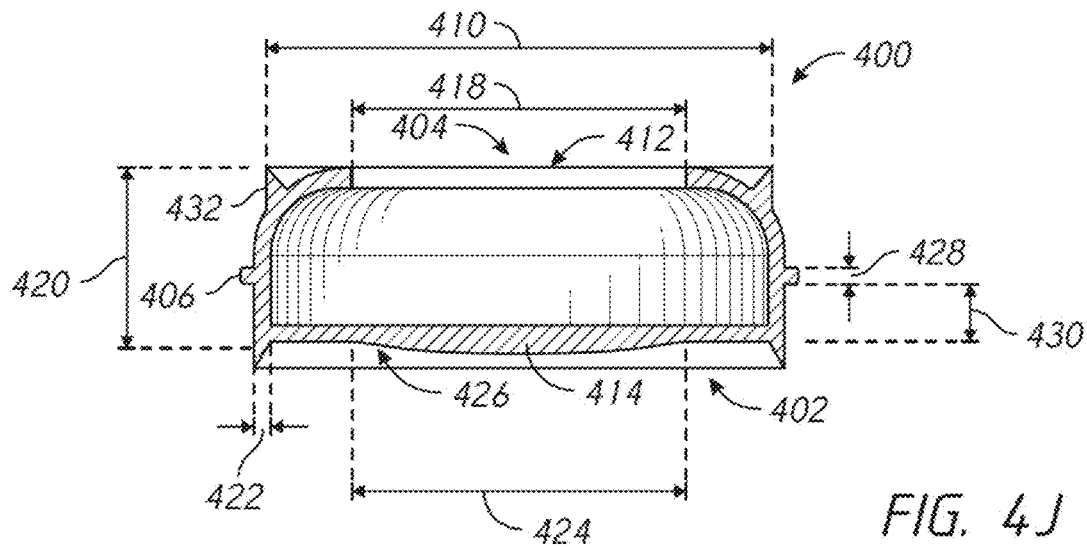
FIG. 4J is a cross-sectional view of the prosthetic capsular device of FIG. 4H along the line 4J-4J of FIG. 4I.

FIGS. 4H-4J illustrate another example prosthetic capsular device 400, in which FIG. 4H is a side view, FIG. 4I is an anterior plan view, and FIG. 4J is a cross-sectional view of along the line 4J-4J of FIG. 4I. The device 400 is illustrative of the prosthetic capsular devices used in the animal studies described herein, with certain modifications where indicated.

The device 400 comprises a posterior side 402 and an anterior side 404. The posterior side 402 has a diameter 408 between about 5 mm and about 10 mm (e.g., about 9.5 mm). The anterior side 404 has a diameter 410 between about 5 mm and about 10 mm (e.g., about 9 mm). The diameter 410 of the anterior side 404 may be between about 0.25 mm and about 1 mm (e.g., about 0.5 mm) less than the diameter 408 of the posterior side. The device 400 comprises a generally cylindrical portion having the diameter 408 from the posterior side 402 to the flange 406, a tapered portion tapering from the diameter 408 to the diameter 410 anterior to the flange 406, and another generally cylindrical portion having the diameter 410 from the tapered portion to the anterior side 404. The tapered portion may be straight, arcuate, and/or combinations thereof.

The posterior side 402 has a generally flat end shape and a rounded refractive portion 414 inwardly set back from the end of the posterior side 402, as best seen in FIG. 4J. The refractive portion 414 provides a refractive property to the device 400. The refractive portion 414 has a diameter 424 between about 4 mm and about 9 mm (e.g., about 5.9 mm). The illustrated refractive portion 414 has a refractive power of 5 D with a radius of curvature 426 of about 19.32 mm) although other refractive powers (e.g., 0 D, <0 D, >0 D, ±35 D, etc.) and radii of curvature (e.g., at least partially depending on one or more of refractive power, the diameter 424, material, etc.) are also possible.

The anterior side 404 comprises an opening 410, which allows the insertion of an IOL as discussed herein. The opening 410 may have a diameter 418 between about 5 mm and about 10 mm (e.g., about 9 mm). The sidewalls of the device 400 optionally do not extend radially inwardly such that the opening 410 may have a large or maximum diameter (e.g., based on the diameter of the inner surface of the sidewalls of the device 400). A larger opening 410 may aid insertion of the IOL and/or reduce volume and/or mass, which can aid insertion into small incisions (e.g., by being easier to compress into and/or advance through an injection device). A smaller opening 410 may aid in containment of an IOL (e.g., better defining the interior volume of the device 400 and/or inhibiting anterior drift on an inserted IOL). The anterior side 404 and/or the posterior side 402 may comprise a lip or ridge 432 on a radial exterior.

The distance 430 between the flange 406 and the refractive portion 414 may be between about 0.5 mm and about 2 mm (e.g., about 1 mm). The distance 420 between the anterior end 404 and the refractive portion 414 may be between about 1 mm and about 5 mm (e.g., about 2.5 mm). As described herein, in devices comprising a flange, the flange may be anywhere along the longitudinal axis of the device.

The device 400 comprises sidewalls between the posterior end 402 and the anterior end 404. The sidewalls may have a radial thickness 422 between about 0.1 mm and about 0.5 mm (e.g., about 0.26 mm). The sidewalls optionally extend posterior to the refractive portion 414 and/or anterior to or substantially longitudinally even with the opening 412. The sidewalls may extend towards the anterior side 404 and/or the posterior side 402 to form a lip or ridge 432.

The device 400 illustrated in FIGS. 4H-4J includes a flange or ring 406 having an anterior-posterior thickness 428 of about 0.3 mm and a radial thickness ((diameter 416–diameter 408)/2) of about 0.25 mm, but the flange 406 was removed from the devices used in the animal studies such that the outer diameter of the devices was the diameter 408. If the flange 406 is not removed, other thicknesses are also possible. For example, a flange 406 having thicker dimensions may be less prone to tearing upon loading in a delivery syringe and/or insertion in an eye.

The prosthetic capsular device 10 can enhance the ability to achieve desired refractive targets, with a side benefit of increased safety. The prosthetic capsular devices (e.g., the prosthetic capsular device 10 and/or variants thereof) described herein can provide one or more of these advantages in one or more of several ways. Although various numbered potential advantages are listed, each advantage may include sub-advantages or alternative advantages, and not all devices 10 need to accomplish every enumerator or otherwise described potential advantage.

First, with reference again the FIGS. 1-3, the prosthetic capsular device 10 can provide centration of the IOL 28 along the visual axis 15. A femtosecond cataract laser system has the ability to center the capsulorhexis around the visual axis 15 of the patient rather than the optical center of the cataract. The capsulorhexis is ultimately what will center the prosthetic capsular device 10 as the capsulorhexis is the opening through which the prosthetic capsular device 10 will be inserted. The capsulorhexis is juxtaposed at the center of the prosthetic capsular device 10, centering the prosthetic capsular device 10. The prosthetic capsular device 10 may optionally be stabilized via the flange 20 extending into and fitting in the ciliary sulcus 22. The flange 20 can mechanically retain the prosthetic capsular device 10 centered on the patient's visual axis 15 and inhibit or prevent future movement or migration of the prosthetic capsular device 10, although centering and inhibited movement are also possible without a flange 20.

Centration of the IOL 28 on the visual axis 15 can be important to the visual function of the IOL 28 and the benefit the patient receives. Aspheric lenses have made decentration more tolerable, however improved centration can be advantageous to the increase or optimize visual performance of multifocal intraocular lenses. Decentration by less than 1 mm can cause significant morbidity, so much so that surgical intervention including laser pupilloplasty, IOL repositioning, and IOL exchange are often performed. The prosthetic capsular device 10 is centered along the visual axis 15 via the capsulorhexis. An IOL 28 commonly includes haptics 30 which can engage opposed interior surfaces in the prosthetic capsular device 10 to maintain the centered position of the IOL 28. The outer diameter of the IOL 28, when unfolded and including the haptics 30, may be substantially equal to or less than the inner diameter of the prosthetic capsular device 10. The IOL 28 can be centered by being in physical contact with the peripheral internal surface of the prosthetic capsular device 10 that is centered in the visual axis 15, which maintains the centered position of the IOL 28 in the prosthetic capsular device 10 and also in the visual axis 15.

Second, the prosthetic capsular device 10 can provide a prosthetic barrier between the anterior segment 26 and posterior segment 32 of the eye 12 in the case of inadvertent rupture of the posterior surface of the natural capsular bag 24, or after planned neodymium-doped yttrium aluminum garnet (Nd:YAG) laser posterior capsulotomy. Despite the overall success of cataract surgery, there is still about 2% surgical complication rate utilizing modern techniques, although this varies among individual surgeons. Residents in ophthalmology training programs have historically had complication rates around 4-7%. Most complications from cataract surgery are caused by inadvertent rupture of the natural capsular bag 24, which houses the cataract. The natural capsular bag 24 also provides an important anatomical barrier within the eye 12 by dividing the anterior segment 26 from the posterior segment 32. The posterior segment 32 contains the vitreous body, retina, optic nerve, and the central retinal artery and vein. A violation of the integrity of the barrier provided by the natural capsular bag 24 allows fluid communication between the anterior segment 26 and the posterior segments 32, and potentially the ocular surface. Vitreous may flow out of the posterior segment 32 according to pressure gradients, flowing from high pressure (e.g., in the posterior segment 32) toward low pressure (e.g., the anterior segment 26). A pressure gradient can cause vitreous to flow directly to the surgical incision site in the lower pressure anterior segment 26. Vitreous can inhibit or prevent wound healing if present at the surgical incision site, and more significantly can provide a conduit for microbial infections to proceed directly to the posterior segment 32. In addition to the problems caused by vitreous, a break or tear in the natural capsular bag 24 can inhibit or prevent the stable implantation of an IOL 28 in the posterior segment 32. Surgeons can place an IOL 28 in the ciliary sulcus 22 or the anterior chamber, although each of these alternatives has their own potential complications associated with them. The natural capsular bag 24 is desirably maintained intact, as there are currently no methods to consistently reestablish the integrity of the natural capsular bag 24 once it has been compromised. Should the natural capsular bag 24 be compromised, the prosthetic capsular device 10 may serve as a prosthetic barrier between the anterior segment 26 and posterior segment 32.

About 30% of all implanted intraocular lenses develop visually significant posterior capsular opacification. If this develops, a Nd:YAG laser may be used to create an opening in the posterior surface of the natural capsular bag 24 to remove this opaque membrane. If the IOL 28 is to be removed after a Nd:YAG laser posterior capsulotomy has been performed, the chances for serious complications rise dramatically because the barrier between the vitreous and the anterior segment 26 has been lost due to the Nd:YAG-created opening in the posterior surface of the natural capsular bag 24. If a prosthetic capsular device 10 is placed in the natural capsular bag 24 and Nd:YAG laser posterior capsulotomy has been performed, the prosthetic capsular device 10 can provide an adequate barrier for the vitreous, inhibiting or preventing vitreous from flowing out of the posterior segment 32. The haptics 30, which hold the IOL 28 in place inside the prosthetic capsular device 10, are not prone to scar formation or fibrosis because they contact the prosthetic capsular device 10 rather than the natural capsular bag 24, which can make future lens removal easier and decrease the risk for complications during IOL 28 exchange. The prosthetic capsular device 10 can provide a platform for routine IOL 28 exchange, as described further herein.

Third, the prosthetic capsular device 10 can limit chronic capsular opacification that takes place in the natural capsular bag 24 and that can cause refractive shifts due to ELP change, anterior capsular phimosis, and visually significant posterior capsular opacification. After cataract surgery has been performed, the natural capsular bag 24 undergoes chronic changes. These changes are largely due to the presence of lens epithelial cells that remain on the natural capsular bag 24 after surgery. These epithelial cells continue to grow and can cause problems. For example, the anterior surface of the natural capsular bag 24 can fibrose and contract over time, causing a progressively smaller aperture overtop of the lens. If the entire natural capsular bag 24 becomes fibrotic, and phimosis persists, there can be zonular dehiscence and changes to the effective lens position over time. About 30% of the time, the posterior surface of the natural capsular bag 24 becomes significantly opacified, which may be remedied by a Nd:YAG laser posterior capsulotomy. The effect of limiting epithelial cell migration and propagation can be mediated by the type of material that the prosthetic capsular device 10 comprises (e.g., hydrophobic acrylic materials, which tend to be most efficacious of all currently known and used IOL materials).

Fourth, the prosthetic capsular device 10 can help maintain the effective lens position of an IOL 28 implanted into the eye 12. Precisely matching the preoperative dimensions of the cataract with the prosthetic capsular device 10 can enhance the ability to predict the ELP of the lens implant 28. Currently, the ELP of an IOL 28 is estimated or predicted based on a number of factors, including the depth of the anterior segment 26, lens thickness, and white to white diameter, among others. The accuracy of the prediction is actually quite low, resulting in only 50% of patients being within a tolerable level of their refractive goal post-cataract surgery. While other dimensions of the eye required for standard IOL calculation can be measured quite precisely and accurately, the ELP has remained the elusive last great variable to conquer in the quest for highly accurate and predictable IOL calculations for cataract surgery.

The reason for the great variability in the ELP is due to the volumetric difference between the cataract and the IOL 28. The average thickness of the human cataract at age 65 is approximately 4.5 mm, but varies from patient to patient. In contrast, an IOL 28 is typically less than 1 mm thick. The thickness of the IOL generally does not match the thickness of the cataract due to deliverability issues, as thicker IOLs generally use a larger incision. The resulting volumetric difference allows for pressure differentials between the posterior segment 32 and the anterior segment 26, as well as contraction of the natural capsular bag 24, which can shift the final resting position of the IOL 28. The lens thickness may be measured preoperatively and a prosthetic capsular device 10 with a corresponding volume and thickness may be implanted. By implanting a prosthetic capsular device 10, the volume of the natural capsular bag 24 may effectively be held constant and/or in accordance with the cataract. The natural capsular bag 24, buttressed by the prosthetic capsular device 10, can resist forces that would otherwise shift the natural capsular bag 24 and its contents anteriorly or posteriorly. This stability of lens capsule volume can increase or significantly increase the accuracy of IOL calculations.

Fifth, the prosthetic capsular device 10 can allow for an intraoperative pseudophakic refraction while still allowing another IOL to be implanted without explanting an originally implanted lens. Recently, there have been advances in IOL calculation methodologies that use intraoperative refraction devices, such as the WaveTec ORA System, the WaveTec Orange System, the HOLOS IntraOp from Clarity Medical Systems, Inc., etc., to provide better refractive outcomes. These devices can perform aphakic refractions, pseudophakic refractions, and assist with the alignment of toric IOLs 28 and assist with Limbal Relaxing Incisions. Aphakic refractions do not have the benefit of a lens inside the eye, so ELP is still a variable for which this data cannot account. Pseudophakic refractions can be helpful, but provide the information only after the IOL 28 has been implanted. If the data shows that a different IOL 28 would be more beneficial, the physician would explant the less beneficial IOL 28 and implant a more beneficial IOL 28. Explanting an IOL 28 takes time, effort, and skill, and can cause damage to the natural capsular bag 24, zonules, cornea, and/or other structures within the eye 12. Using a prosthetic capsular device 10 with a low power lens incorporated into its posterior surface (e.g., the posterior refractive surface 19) can allow a physician to perform a pseudophakic refraction with this refractive surface, and still provides the physician the ability to implant a second lens (e.g., the IOL 28) within the prosthetic capsular device 10 that will make up the refractive difference as measured by an intraoperative refraction device, such as the WaveTec ORA System and Clarity HOLOS.

Stabilization of the natural capsular bag 24 by insertion of the prosthetic capsular device 10 can be leveraged to perform an intraoperative optical coherence tomography (OCT) measurement and/or A or B scan ultrasound, for example using commercially available systems such as the Zeiss RESIGHT OCT and/or any of a multitude of ophthalmic AB scan ultrasound systems. Once the prosthetic capsular device 10 is inserted into the natural capsular bag 24, the anterior and posterior capsule can be stented open into a stable configuration, which should be unlikely to significantly change post operatively. By knowing the corneal power, the distance from the cornea to the refractive surface of the prosthetic capsular device 10, and the distance from the refractive surface of the prosthetic capsular device 10 to the surface of the retina, the ELP can be determined. By knowing the ELP, the power of the cornea, the refractive power built in to the posterior aspect of the prosthetic capsular device 10, and the axial length of the eye 12 (e.g., from the surface of the corneal epithelium to the internal limiting membrane (ILM) (ultrasonic technique), the retinal pigment epithelial (RPE) layer (laser interferometry technique), from cornea to retina), an appropriate second lens (e.g., of an IOL) can be selected and implanted into the open space in the prosthetic capsular device 10 to provide the desired refractive outcome.

Sixth, the prosthetic capsular device 10 may serve as a means for pharmaceutical delivery. Pharmaceuticals, drugs, and medications, such as, for example, slow release fully or partially dissolvable medicine pellets, non-dissolvable prostheses coated with slow release pharmaceutical agents, and/or other substances intended for introduction into the eye 12 may be placed in and/or on prosthetic capsular device 10 outside of the visual axis 15 in a location that is not subject to sequestration by membrane formation. There is a tremendous amount of research and demand for a slow release implant that would essentially eliminate the need for post-cataract surgery eye drops. The prosthetic capsular device 10 would be a suitable receptacle for such an implant, as the periphery of the interior of the prosthetic capsular device 10 provides a location outside of the visual axis 15, in constant contact with the aqueous humor, substantially without risk of becoming encapsulated by scarring. Due to the prosthetic material of the prosthetic capsular device 10, there would be little to no risk of membrane formation or encapsulation. Dissolved or suspended pharmaceuticals would not affect the patient's vision and could be introduced directly into the prosthetic capsular device 10 during the implantation surgery. Larger pharmaceuticals, such as slow release medicine pellets, may be shaped to mechanically maintain their position with respect to the prosthetic capsular device 10. For example, a slow release medicine pellet may be constructed with a generally toroidal shape sized to fit within the prosthetic capsular device 10, while remaining in the peripheral space and not obstructing the visual axis 15.

Seventh, the prosthetic capsular device 10 may provide physicians with the ability to perform a lens exchange in the future that can reduce or minimize the risk of damage to the natural capsular bag 24 and zonular apparatus, which ultimately can substantially reduce or minimize the risk of serious vision threatening sequelae such as macular edema, macular hole, retinal tear, retinal detachment, proliferative vitreoretinopathy, and/or loss of capsular support leading to less favorable lens implantation techniques (e.g., a sutured or glued IOL 28, an anterior chamber IOL 28, a posterior chamber IOL 28, etc.). As stated above, if a prosthetic capsular device 10 is placed in the natural capsular bag 24 and a Nd:YAG laser posterior capsulotomy has been performed, the prosthetic capsular device 10 provides an adequate barrier for the vitreous. The haptics 30 which hold the IOL 28 in place inside the prosthetic capsular device 10 are not prone to scar formation, making future removal and/or exchange of the IOL 28 easier.

Figure 6:
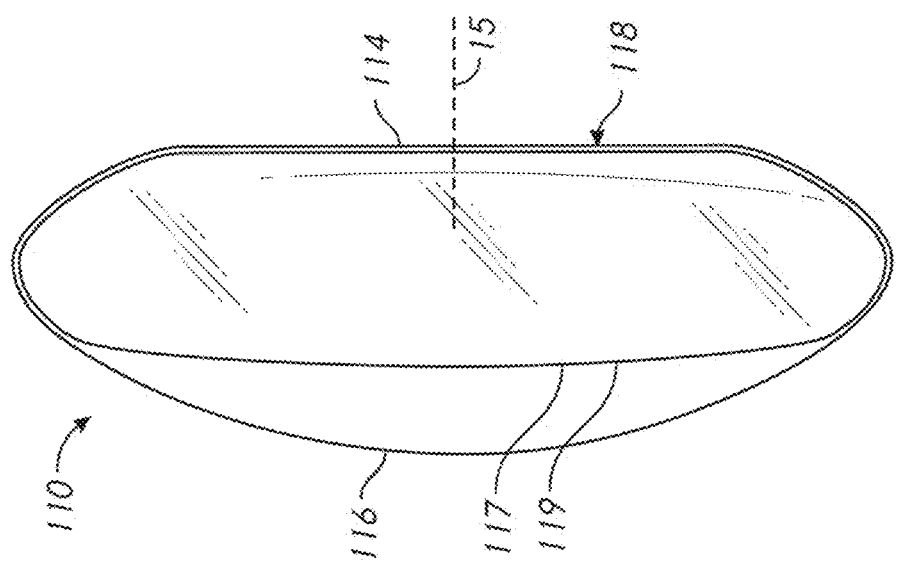
FIG. 6 depicts a side view of the example prosthetic capsular device shown in FIG. 5.
Figure 5:
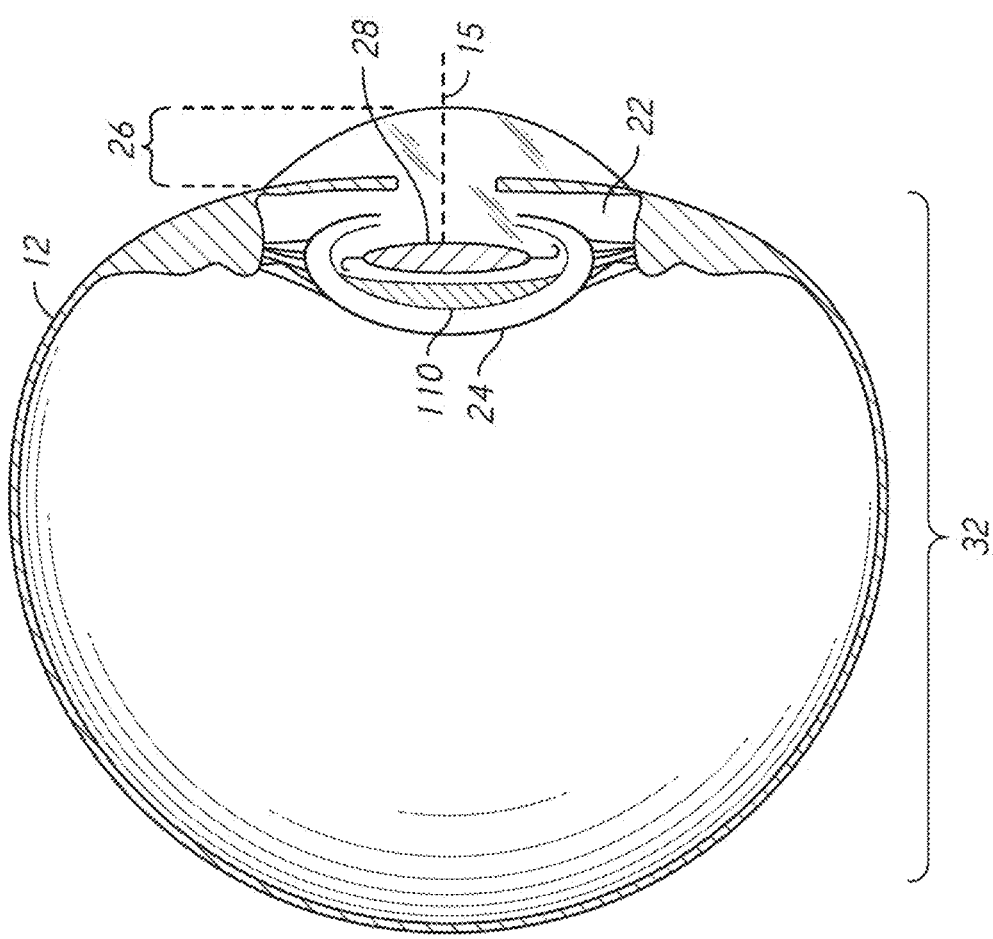
FIG. 5 depicts a cross-sectional side view of an eye including another example of a prosthetic capsular device containing including an IOL.
Figure 7:
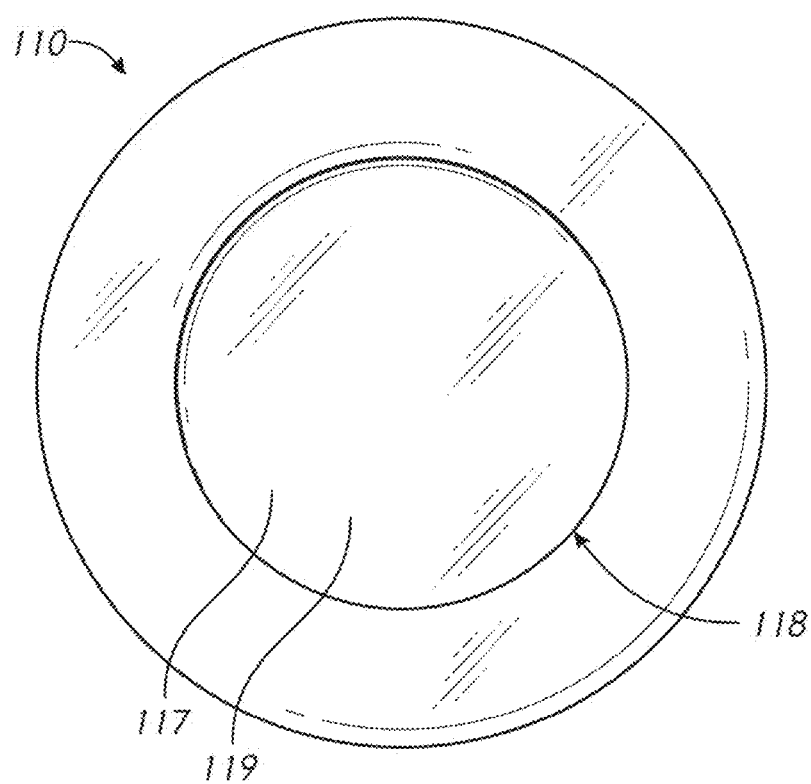
FIG. 7 depicts an anterior plan view of the example prosthetic capsular device shown in FIG. 5.

FIGS. 5-7 depict another example prosthetic capsular device 110. The prosthetic capsular device 110 is a substantially discoid shape having a thickness between about 2.5 mm and about 4.5 mm and a diameter of about 9 mm, although other dimensions, for example as described herein with respect to the prosthetic capsular device 10, 400, are also possible. The thickness of the prosthetic capsular device 110 is the distance between the anterior surface 114 and posterior surface 116 of the prosthetic capsular device 110 along the visual axis 15. The anterior surface 114 contains a circular opening 118 having a diameter of about 6 mm. At least a portion of the inner face 117 of the posterior surface 116 of the prosthetic capsular device 110 comprises a refractive surface, e.g., the posterior refractive surface 119. The prosthetic capsular device 110 lacks or is free of a flange 20 (as in the prosthetic capsular device 10) that could mechanically fixate or center the prosthetic capsular device 110 on the capsulorhexis. The volume of the prosthetic capsular device 110 relative to the opening of the capsulorhexis may keep the device in place similar to the manner in which current single piece IOLs 28 are folded and placed within the natural capsular bag 24.

The prosthetic capsular device 110 may sacrifice a measure of stability as compared to the prosthetic capsular device 10 comprising a flange 20. Without a flange, the prosthetic capsular device 110 may be usable for non-femtosecond laser cataract removal (e.g., traditional manual phacoemulsification), and may be particularly useful for surgeons who lack access to a femtosecond laser.

The lenticular surface on the posterior aspect of a prosthetic capsular device may have a plano powered lens. Some extreme myopes would not benefit from a +1 D refractive surface, as they may benefit from a negative IOL 28 power. For patients with these conditions, a prosthetic capsular device may be used with a plano or zero power posterior lenticular surface.

The prosthetic capsular device may have a posterior refractive lenticular surface (e.g., −1 D), as some extreme axial myopes (about 30 mm and beyond) may benefit from this type of lens.

The posterior refractive surface of a prosthetic capsular device may comprise a multifocal lenticular surface, which could aid in presbyopia correction. This multifocal lenticular surface may include, but is not limited to, refractive, diffractive, and zonal multifocal refractive technology. A multifocal lens may be designed to provide multiple focal points generally ranging from plano (e.g., 0 D) to +3 D or greater at the spectacle plane.

The posterior refractive surface of a prosthetic capsular device may include a spherical, aspheric, and/or cylindrical (astigmatic) lenticular surface so as to aid in the correction of pre-existing and surgically induced corneal astigmatism. As most surgeons induce between −0.25 D and −0.50 D of astigmatism with their corneal incisions required for cataract surgery, it would be beneficial even for most patients with spherical corneas to have this neutralized. The dioptric power of the toric correction could increase up to 6 diopters for patients with even higher amounts of astigmatism.

Figure 8:
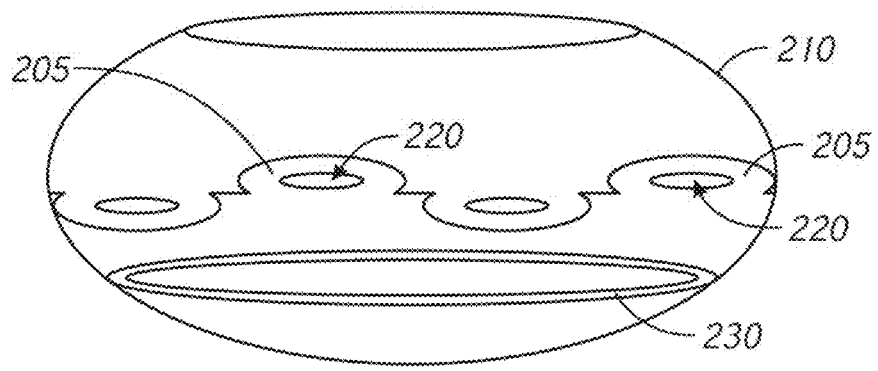
FIG. 8 depicts a side view of an example prosthetic capsular device comprising an outer surface including, around a perimeter of the outer surface, a continuous outer rim of tabs (e.g., comprising silicone) each tab including an opening in a center of the tab, and the capsular device including an internal lip configured to hold haptics of an IOL.

In some implementations described herein (e.g., the prosthetic capsular device 110 shown in FIG. 6, the prosthetic capsular device 400 with the flange 406 removed or never formed), the prosthetic capsular device (e.g., bag, bowl, housing, structure, cage, frame) does not include or is free of a flange. Certain such implementations may include, around a perimeter of the prosthetic capsular device 210, an outer rim comprising tabs or haptics 205. The rim may be continuous, and tabs 205 that are in contact may be considered continuous. Tabs 205 that are continuous may provide better apposition with the natural capsular bag and/or be more form fitting than a device in which the tabs 205 are not continuous. The tabs 205 may position (e.g., center) the device 210 in a desired position. Some or all of the tabs 205 may include an opening or hole 220, for example in the approximate center of the tab 205. An example prosthetic capsular device 210 comprising a continuous outer rim comprising tabs 205 each including an opening or hole 220 is illustrated in FIG. 8. The rim, tabs 205, and/or openings 220 can assist the prosthetic capsular device 210 to fit inside natural capsular bags of many sizes and shapes. The prosthetic capsular device 210 preferably allows for some fibrosis through the openings 220, which can stabilize the capsule 210 in the event of a Nd:YAG laser posterior capsulotomy. The tabs 205 can comprise, for example, silicone, silicone derivatives, acrylic, acrylic derivatives, biocompatible methacrylates (e.g., poly(methyl methacrylate) (PMMA)), collamer, olefins (e.g., polypropylene), polyimide, combinations thereof, and the like. The tabs 205 may comprise the same material as (e.g., be integrally formed with) the remainder of the device 210 or may comprise a different material than the remainder of the device 210 (e.g., being overmolded over the remainder of the device 210). The device 210, like other prosthetic capsular bags described herein, may comprise a plurality of pieces and/or materials, which may advantageously allow selection or use of a material suitable for the function of that component, as opposed to selection or use of a material having compromising suitability for several functions. If the remainder of the device 210 comprises opaque material, the tabs 205 may comprise opaque and/or transparent material, for example because the opaque material of the remainder of the device 210 can reduce or minimize intraocular scattering and/or glare such that light may not reach the tabs 205. The prosthetic capsular device 210 can include an internal lip 230. The internal lip 230 can run partially, intermittently, or completely around the inside of the prosthetic capsular device 210. The lip 230 may be designed to hold the haptics of an IOL stable, inhibiting or preventing the lens from rotating or shimmering during eye movements.

In some implementations, the prosthetic capsular device intentionally moves away from natural form fitting conformation of the posterior aspect of the device. This can allow for the posterior aspect of the prosthetic capsular device to have a larger diameter (e.g., the largest diameter possible for the physiology), potentially allowing for implants with a wider diameter to be implanted, and to have a more stabilizing effect on the lens that the device will be holding.

In some implementations, the prosthetic capsular device 210 comprises at least one of the following: external form-fitting elements (e.g., the tabs 205 shown in FIG. 8); openings in the external form-fitting elements through which fibrosis can take place, thereby allowing stabilization of the positioning of the device (e.g., the openings 220 in the tabs 205 shown in FIG. 8); and an internal lip/sulcus configured to secure the haptics of a standard IOL (e.g., the lip 230 shown in FIG. 8).

Figure 9A:
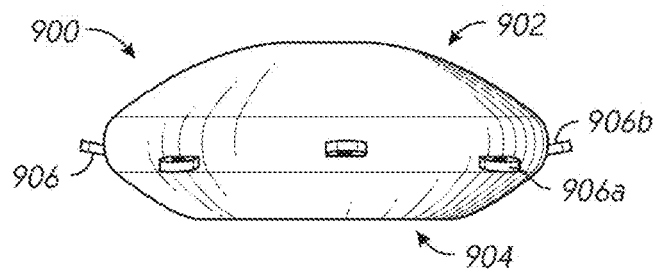
FIG. 9A depicts a side view of another example prosthetic capsular device.
Figure 9B:
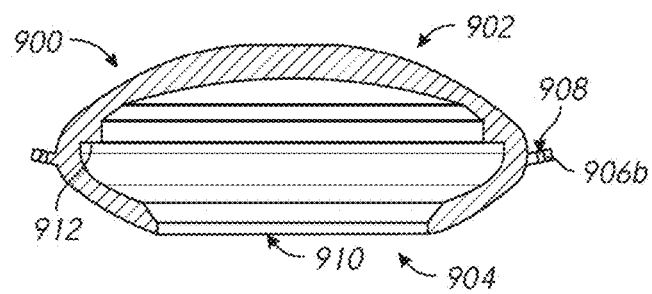
FIG. 9B depicts a side cross-sectional view of the prosthetic capsular device of FIG. 9A.
Figure 9C:
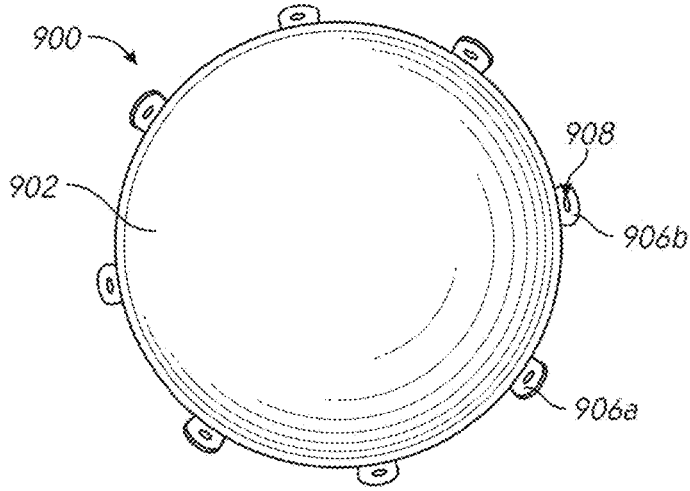
FIG. 9C depicts a posterior plan view of the prosthetic capsular device of FIG. 9A.
Figure 9D:
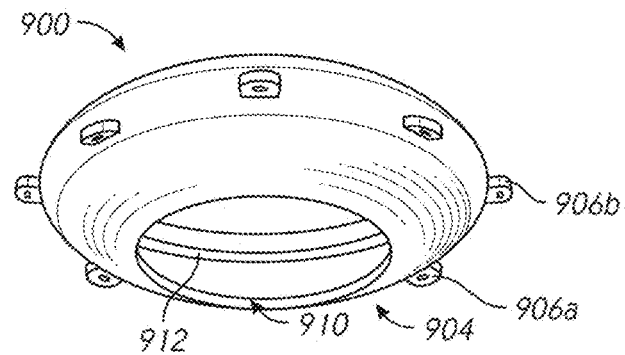
FIG. 9D depicts an anterior side perspective view of the prosthetic capsular device of FIG. 9A.

FIGS. 9A-9D illustrate another example prosthetic capsular device 900, in which FIG. 9A is a side view, FIG. 9B is a side cross-sectional view, FIG. 9C is a posterior plan view, and FIG. 9D is an anterior side perspective view. The prosthetic capsular device (e.g., bag, bowl, housing, structure, cage, frame) 900 does not include or is free of a flange, although combination with a flange (e.g., the flange 20) is also possible. The device 900 comprises a posterior side 902 and an anterior side 904. The posterior side 902 has a generally rounded shape. As shown in FIG. 9B, the posterior side 902 comprises a refractive portion, which provides a refractive property to the device 900.

As shown in FIGS. 9B and 9D, the anterior side 904 comprises an opening 910, which allows the insertion of an IOL as discussed herein. The opening 910 may have sharp edges (e.g., as depicted in FIGS. 9B and 9D), rounded edges (e.g., as shown in other implementations herein), etc. The opening 910 may have a diameter between about 5 mm and about 10 mm (e.g., between about 6 mm and about 9 mm). The sidewalls of the device 900 optionally do not extend radially inwardly such that the opening 910 may have a large or maximum diameter (e.g., based on the diameter of the inner surface of the sidewalls of the device 900). A larger opening 910 may aid insertion of the IOL and/or reduce volume and/or mass, which can aid insertion into small incisions (e.g., by being easier to compress into and/or advance through an injection device). A smaller opening 910 may aid in containment of an IOL (e.g., better defining the interior volume of the device 900 and/or inhibiting anterior drift on an inserted IOL).

As shown in FIGS. 9B and 9D, the device 900 comprises an internal lip 912. The internal lip 912 can run partially, intermittently, or completely around the inside of the prosthetic capsular device 900. The lip 912 may be designed to hold the haptics of an IOL stable, inhibiting or preventing the lens from rotating or shimmering during eye movements. The lip 912 is proximate to a midpoint of the device 900, for example being proximate to a plane about half way between the posterior side 902 and the anterior side 904. The lip 912 may be proximate to the anterior side 902, proximate to the anterior side 904, etc., and can be designed and/or selected based on the IOL to be inserted into the device 900. The device 900 may comprise a plurality of lips 912, for example configured to engage a plurality of IOLs and/or to provide a plurality of alternative positions to engage one IOL. The lip 912 may comprise a tubular structure, for example configured to lockingly engage haptics of an IOL (e.g., by insertion of end portions of one or more haptics into a lumen of the tubular structure, by resilient compression of the tubular structure by a haptic, etc.). Rather than extending radially inwardly (e.g., as shown in FIGS. 9B and 9D), the lip 912 could extend radially outwardly, for example comprising a groove in the inner sidewalls of the device 900. A lip 912 comprising a groove may be integrally formed (e.g., during molding of the device 900) and/or formed after (e.g., by laser milling). Combinations of the lips 912 described herein are also possible. For example, the lip 912 could comprise: one or a plurality of lips 912; position(s) proximate to a surface and/or a midpoint; continuous and/or intermittent; filled and/or tubular; a groove extending into the sidewalls of the device 900; and combinations thereof.

The device 900 comprises, around a perimeter of the device 900, a plurality of tabs or haptics 906. The tabs 906 are not in contact and may be considered not continuous. Tabs 906 that are not continuous may use less material and impart less volume and/or mass to the device 900, allowing the device 900 to be easier to insert into small incisions. Use of less material may reduce costs due to use of less material. As discussed above, tabs that are continuous may provide better apposition with the natural capsular bag and/or be more form fitting, but may use more material and impart more volume and/or mass to a device, which can inhibit insertion into small openings. Depending on the application, the devices described herein that include tabs may include tabs that are continuous, not continuous, and combinations thereof (e.g., comprising continuous tabs over a portion of the perimeter).

The tabs 906 comprise an opening or hole or aperture 908. The openings 908 illustrated in FIGS. 9A-9D extend all of the way through the tabs 906, but could extend only partially through the tabs 906. The openings 908 may assist in suturing the device 908, allow fibrosis therethrough, etc. The tabs 906 include tabs 906a that are anteriorly biased and tabs 906b that are posteriorly biased. Biased tabs 906 (e.g., tabs 906a, 906b having alternating bias) can inhibit preferential torqueing and tilt. In addition and/or alternatively to being differently biased, the tabs 906 may have other differences (e.g., shape, material, absence of an opening 908, anterior-posterior position, orientation, combinations thereof, and the like).

Figure 10A:
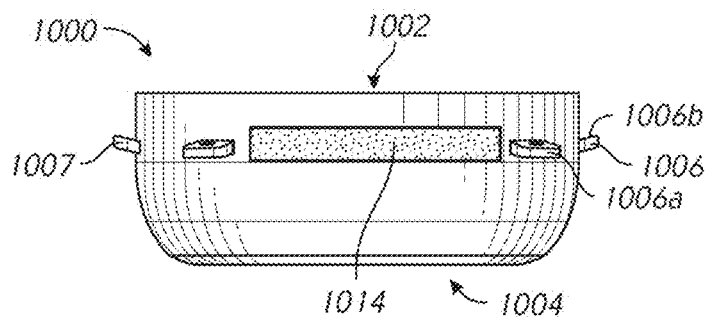
FIG. 10A depicts a side view of yet another example prosthetic capsular device.
Figure 10B:
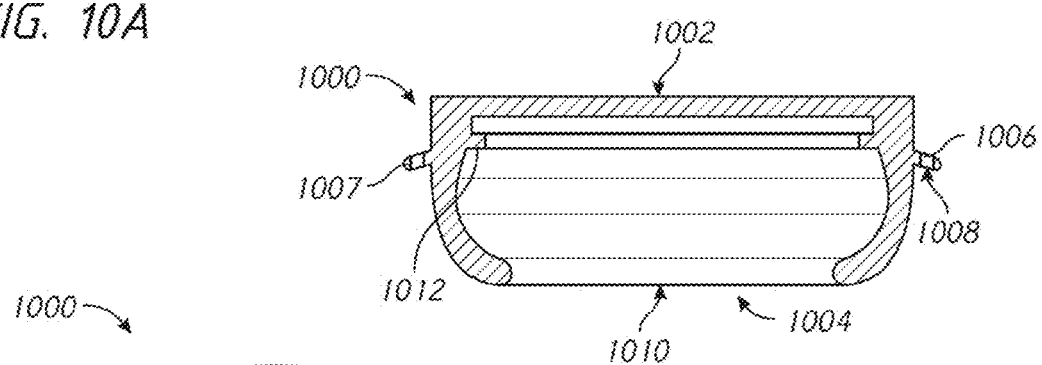
FIG. 10B depicts a side cross-sectional view of the prosthetic capsular device of FIG. 10A.
Figure 10C:
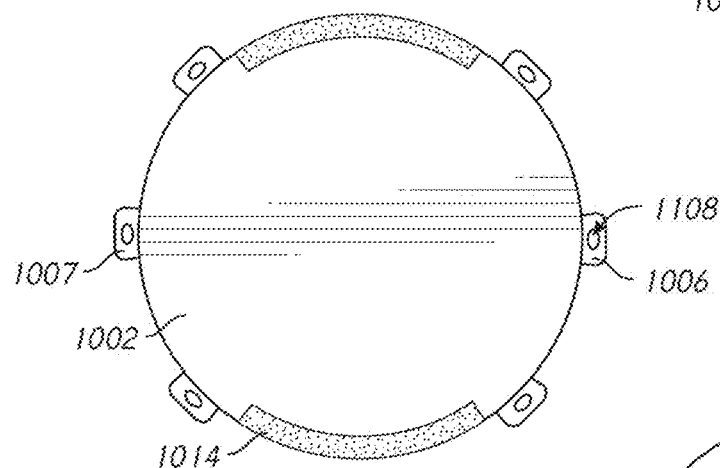
FIG. 10C depicts a posterior plan view of the prosthetic capsular device of FIG. 10A.
Figure 10D:
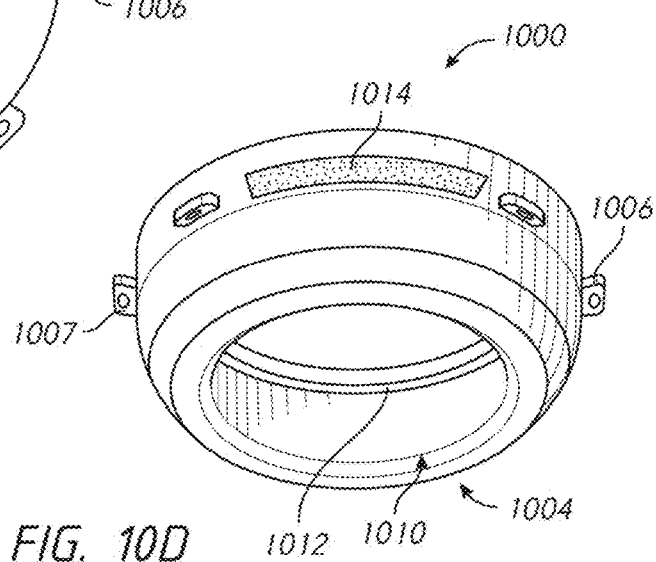
FIG. 10D depicts an anterior side perspective view of the prosthetic capsular device of FIG. 10A.

FIGS. 10A-10D illustrate yet another example prosthetic capsular device 1000, in which FIG. 10A is a side view, FIG. 10B is a side cross-sectional view, FIG. 10C is a posterior plan view, and FIG. 10D is an anterior side perspective view. The prosthetic capsular device (e.g., bag, bowl, housing, structure, cage, frame) 1000 does not include or is free of a flange, although combination with a flange (e.g., the flange 20) is also possible. The device 1000 comprises a posterior side 1002 and an anterior side 1004. The posterior side 1002 has a generally flat shape. As shown in FIG. 10B, the posterior side 1002 comprises a solid surface, but substantially constant thickness and parallel planar surfaces are indicative of a lack of a refractive portion, which may be useful if the IOL provides sufficient refractive power (e.g., if the diopter value is low). Although the posterior side 1002 is flat, the interior surface of the posterior part of the device 1000 could be curved such that the device 1000 can provide refractive power even though the outer surface is flat.

As shown in FIGS. 10B and 10D, the anterior side 1004 comprises an opening 1010, which allows the insertion of an IOL as discussed herein. The opening 1010 may have sharp edges (e.g., as shown in other implementations herein), rounded edges (e.g., as depicted in FIGS. 10B and 10D), etc.

As shown in FIGS. 10B and 10D, the device 1000 comprises an internal lip 1012. The internal lip 1012 can comprise the same options and/or features as discussed herein (e.g., with respect to the lip 912). The lip 1012 is proximate to the posterior side 1002, for example being posterior to a plane half way between the posterior side 1002 and the anterior side 1004 and/or being posterior to the tabs 1006. Consistent with the lip 1012 comprising the options of other lips described herein, the lip 1012 may be proximate to the anterior side 1004, proximate to a midpoint, etc., and can be based on the IOL to be inserted into the device 1000.

The device 1000 comprises, around a perimeter of the device 1000, a first plurality of tabs or haptics 1006 and a second plurality of tabs or haptics 1007. The tabs 1006, 1007 can comprise the same options and/or features as discussed herein (e.g., with respect to the tabs 906). The pluralities of tabs 1006, 1007 are not in contact and may be considered not continuous. The pluralities of tabs 1006, 1007 are spaced from each other about a perimeter of the device 1000, bunched at two opposite sides of the device 1000. Pluralities of tabs may be bunched at one side, two sides (e.g., as shown in FIGS. 10A-10D), three sides, etc. Pluralities of tabs may be evenly circumferentially spaced (e.g., as shown in FIGS. 10A-10D) or unevenly circumferentially spaced. Pluralities of tabs may comprise the same types of tabs (e.g., as shown in FIGS. 10A-10D) or different types of tabs (e.g., comprising different anterior-posterior bias, shape, material, absence of an opening 1008, anterior-posterior position, orientation, continuousness, combinations thereof, and the like). Tabs within a plurality of tabs may be the same or different (e.g., comprising different anterior-posterior bias (e.g., as shown by the tabs 1006a, 1006b in the plurality of tabs 1006), shape, material, absence of an opening 1008, anterior-posterior position, orientation, continuousness, combinations thereof, and the like). In implementations in which the tabs comprise circumferentially spaced pluralities of tabs (e.g., the tabs 1006, 1007), the tabs may be configured to provide more engagement (e.g., by being larger, by being continuous, combinations thereof, and the like) than if the tabs extend all around the perimeter of the device. Use of fewer tabs by circumferentially spacing pluralities of tabs 1006, 1007 may reduce volume and/or mass, which can aid insertion into small incisions (e.g., by being easier to compress into and/or advance through an injection device). Use of fewer tabs by circumferentially spacing pluralities of tabs 1006, 1007 may reduce costs due to use of less material. As discussed above, tabs that are continuous may provide better apposition with the natural capsular bag and/or be more form fitting, but have increased volume and/or mass. Depending on the application, the devices described herein that include tabs may include tabs that are continuous, not continuous, and combinations thereof (e.g., comprising continuous tabs over a portion of the perimeter).

The tabs 1006, 1007 are illustrated as being generally short, rounded-edge rectangular structures. Other shapes are also possible, for example arcuate (e.g., semicircular), elongate (e.g., spiraling out of the device 1000), having end features (e.g., loops, hooks), etc. When pluralities of tabs 1006, 1007 are circumferentially spaced, the perimeter of the device 1000 may have room for more voluminous tabs 1006, 1007.

As shown in FIGS. 10A, 10C, and 10D, the device 1000 comprises textured surfaces 1014. The textured surfaces 1014 may comprise pores (e.g., extending partially through the walls of the device, extending fully through the walls of the device 1000, circular, spherical, elongate, having an undulating pattern, etc.), surface texture patterns, combinations thereof, and the like. The textured surfaces 1014 may be configured to capture, engage, and/or promote fibrosis (e.g., by not being smooth). The textured surfaces 1014 may be formed during forming the device 1000 (e.g., by being integrated into a mold) and/or formed after forming the device 1000 (e.g., by laser drilling). The device 1000 and/or other prosthetic capsular devices may lack or be free of tabs 1006, 1007, and the textured surfaces 1014 may provide engagement with the natural capsular bag, allow fibrosis, etc. The device 1000 may comprise tabs 1006, 1007 comprising openings or holes 1008 that may assist in suturing the device 908, allow fibrosis therethrough, etc. and textured surfaces 1014 that may allow fibrosis. The textured surfaces 1014 of the device 1000 are positioned between the pluralities of tabs 1006, 1007, but any portion of the device 1000 may comprise a textured surface, preferably not in the optical path, which can permit strategic fibrosis. The textured surfaces 1014 may be continuous around the perimeter, circumferentially spaced (e.g., as shown in FIG. 10C), in patches, etc. If the device 1000 comprises tabs, the tabs may comprise textured surfaces.

Figure 11A:
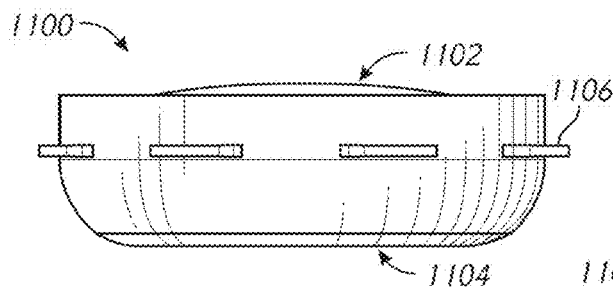
FIG. 11A depicts a side view of still another example prosthetic capsular device.
Figure 11B:
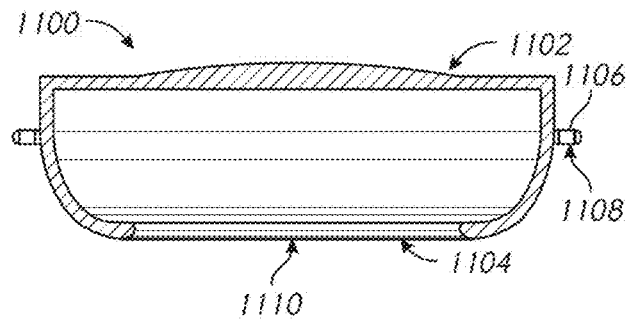
FIG. 11B depicts a side cross-sectional view of the prosthetic capsular device of FIG. 11A.
Figure 11C:
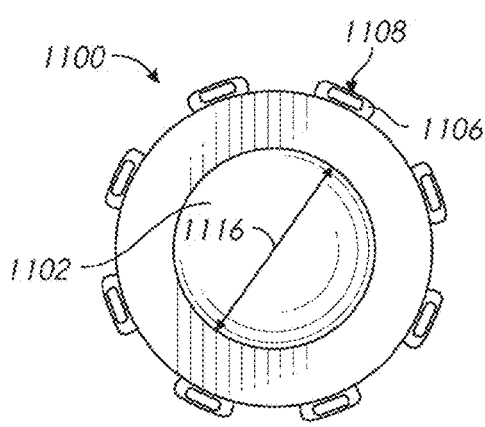
FIG. 11C depicts a posterior plan view of the prosthetic capsular device of FIG. 11A.
Figure 11D:
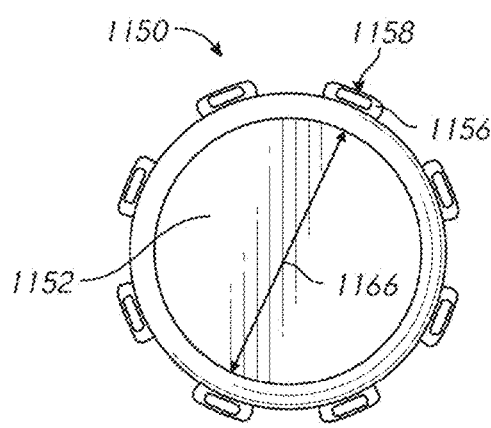
FIG. 11D depicts a posterior plan view of still yet another example prosthetic capsular device.
Figure 11E:
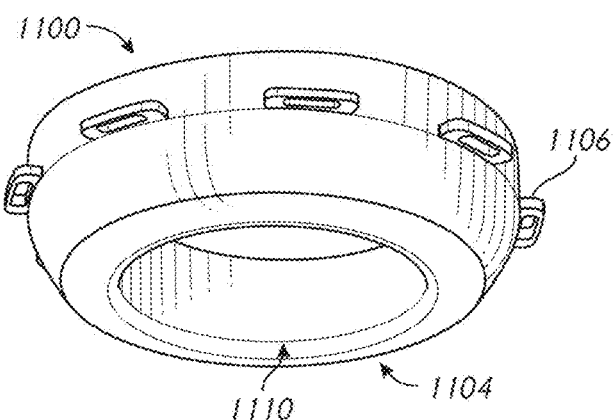
FIG. 11E depicts an anterior side perspective view of the prosthetic capsular device of FIG. 11A.

FIGS. 11A-11C and 11E illustrate still another example prosthetic capsular device 1100, in which FIG. 11A is a side view, FIG. 11B is a side cross-sectional view, FIG. 11C is a posterior plan view, and FIG. 11E is an anterior side perspective view. FIG. 11D depicts a posterior plan view of still yet another example prosthetic capsular device 1150 that is similar to the device 1100 except for the refractive portion, as described in further detail below. The prosthetic capsular device (e.g., bag, bowl, housing, structure, cage, frame) 1100 does not include or is free of a flange, although combination with a flange (e.g., the flange 20) is also possible. The device 1100 comprises a posterior side 1102 and an anterior side 1104.

The posterior side 1102 has a generally flat edge with a convex central portion. As shown in FIG. 11C, convex central portion of the posterior side 1102 comprises a refractive portion, which provides a refractive property to the device 1100 for refractive powers >0 D (positive or converging lens power). The posterior side 1102 can include a concave central portion for refractive powers <0 D (negative or diverging lens power). As shown in FIG. 11C, the refractive portion of the device 1100 has a diameter 1116 that is about 6 mm. As shown in FIG. 11C, the refractive portion of a similar device 1150 has a diameter 1166 that is about 8 mm. Most IOL optics have a diameter between 5.5 mm and 6 mm since the refractive power range of IOLs is typically ±35 D, and IOLs are designed to be substantially the same throughout the refractive power range such that even low refractive power IOLs have a diameter similar to that of a high refractive power IOL. The diameters of the refractive portion of the devices 1100, 1150 are not limited by refractive power value, which can allow larger diameter refractive portions as evidenced by the device 1150. The devices 1100, 1150 could provide a small refractive power value to aid an IOL, which could allow IOLs with smaller refractive powers to be used, resulting in a total refractive power, which could potentially increase the diameter of such IOLs if no longer designed based on a full refractive power range. The devices 1100, 1150 could provide a refractive surface that has sufficient refractive power that no IOL providing additional refractive power is inserted into device 1100, 1150.

As shown in FIGS. 11B and 11D, the anterior side 1104 comprises an opening 1110, which allows the insertion of an IOL as discussed herein. The opening 1110 may have sharp edges (e.g., as shown in other implementations herein), rounded edges (e.g., as depicted in FIGS. 11B and 11E), etc.

As shown in FIGS. 11B and 11E, the device 1100 lacks or is free of an internal lip. Lack of an internal lip may reduce volume and/or mass, which can aid insertion into small incisions (e.g., by being easier to compress into and/or advance through an injection device). Lack of an internal lip may reduce costs due to use of less material. Alternatively, the device 1100 may comprise an internal lip, as the features described with respect to the devices described in the present application may be optionally substituted, interchanged, rearranged, etc. when compatible.

The device 1100 comprises, around a perimeter of the device 1100, a plurality of tabs or haptics 1106. The device 1150 comprises, around a perimeter of the device 1150, a plurality of tabs or haptics 1156. The tabs 1106, 1156 can comprise the same options and/or features as discussed herein (e.g., with respect to the tabs 906, 1006, 1007). The pluralities of tabs 1106, 1156 are not in contact and may be considered not continuous. The tabs 1106, 1156 are not biased in an anterior and/or posterior direction, which may be easier to manufacture than biased tabs. The tabs 1106, 1156 are larger than the tabs 906, 1006, 1007 described herein. Larger tabs 1106, 1156 may increase apposition of the device 1100, 1150 to a natural capsular bag and/or increase fibrosis surface area. Larger tabs 1106, 1156 may also allow the formation of larger openings 1108, 1158. Openings that extend all the way through a tab, if desired, may be difficult to produce in small tabs, so the larger tabs 1106, 1156 may enable easier formation of larger openings 1108, 1158 that fully extend through the tabs 1106, 1156. Larger openings 1108, 1158 may aid in suturing.

The prosthetic capsular devices described herein or similar prosthetic capsular devices may be compatible with any IOLs that are currently commercially available or developed in the future, regardless of manufacturer (e.g., AcrySof from Alcon, TECNIS from Abbott Medical Optics, enVista, TRULIGN, Akreos, SofPort, and Crysalens from Bausch and Lomb, iSert from Hoya Corporation, ELENZA Sapphire from Elenza, Calhoun light adjustable lens from Calhoun Vision, and others), material (e.g., comprising PMMA, silicone, relatively hydrophobic acrylic, relatively hydrophilic acrylic, other acrylic, collamer, combinations thereof, and the like), product type (e.g., aphakic, pseudophakic), refractive power (e.g., negative, planar, and positive), number of pieces (e.g., one, two, three, and more), accommodation (e.g., accommodating and non-accommodating), size (e.g., diameter, thickness), shape (e.g., disc, toroid, symmetric, and asymmetric), haptic type and quantity, delivery system, delivery profile, expansion profile, combinations thereof, and the like.

Referring again to the potential advantages described above, the prosthetic capsular devices described herein or similar prosthetic capsular devices can increase the options for IOL replacement. A physician may be less reluctant to perform IOL replacement if the initially-implanted lens fails due to the reduce risk of complications, such that the physician will more readily replace the initially-implanted lens with a more appropriate lens, thereby providing a better outcome (e.g., initial outcome). Even without replacement, the IOL selection capability provided by the refractive portion of the prosthetic capsular device and/or the positioning capability provided by the prosthetic capsular device and can improve outcome (e.g., initial outcome). Certain prosthetic capsular devices described herein may be able to provide more accurate refractive outcomes after initial surgery every or almost every time.

Since IOL replacement from a prosthetic capsular device involves less risk than IOL replacement without a prosthetic capsular device, physicians and patients may also be more open to replacement of the IOL over time. For example, IOL replacement may be potentially advantageous for medical reasons (e.g., due to changing physiological conditions (e.g., development of macular degeneration, glaucomatous optic neuropathy), refractive reasons (e.g., change of corneal power due to corneal dystrophy, the progressive hyperopic shift associated with previous refractive keratotomy), the patient's desire to access new intraocular technology (e.g., powered accommodating IOL, implantable intraocular wireless input/output computerized devices)), such that replacement of an IOL in a prosthetic capsular device can provide improved outcomes even after the initial surgery. The reduced risk of complications due to removal from and placement in a prosthetic capsular device may even permit physicians and patients to exchange the IOL as often as desirable. The ability to change the IOL more often due to a prosthetic capsular device may also permit surgery at an earlier age, as the physician may dispossess concerns that the initially-implanted IOL must last the rest of the patient's life or risk serious complications upon replacement. Such IOL replacement procedures may even be able to substitute for removable corrective devices such as glasses and contact lenses.

The prosthetic capsular devices described herein or similar prosthetic capsular devices may provide a platform by which a technology device (e.g., a wearable miniaturized electronic technology device) can be inserted and carried in the eye independent of or in combination with an IOL. As used herein, the phrase "technology device" is a broad term including any device that generally provides biometric measurement functions, computer functions (e.g., digital data input directly via wireless signals and/or indirectly through sensors, data analysis, input, and/or output), image generation and projection onto the retina, and/or internet/WiFi capabilities and is small enough to fit functionally within the eye (e.g., having a diameter less than or equal to about 11 mm and a thickness less than or equal to about 6 mm), some of which can be used to perform useful electronic functions for the wearer. Examples of such devices include, but are not limited to, computers (e.g., Google Glass, Microsoft Hololens), virtual reality devices, head-mounted displays (such as graphic or image displays, map displays), devices with WiFi and/or internet connectivity, image receivers (e.g., television or movies), game devices, projectors (including image viewers, image readers, or image senders), GPS devices, biometric measurement devices (e.g., blood glucose level sensors, electrolyte sensors, heart rate sensors, basal metabolic rate sensors, temperature sensors, EEG, EKG, intraocular pressure sensors, ciliary muscle contraction sensors, dynamic pupil change sensors), retinal prostheses, camera functions (e.g., still image and/or video recording), and e-mail senders or receivers. Such devices do not necessarily have to be characterizable as wearable (e.g., because they are implanted rather than "worn"), miniaturized (e.g., because they may have already been a certain size), or electronic (e.g., because they may be mechanical), but would still be a "technology device" as described herein.

In use, the technology device is in the prosthetic capsular device, and the output from the electronic device is provided to the user, either through viewing of the output visually through the eye or otherwise (e.g., wireless transmission to an external computing device). Data from the outside of the body can be transmitted to and/or from the technology device in a wireless electromagnetic energy format including, but not limited to, currently available modalities such as Bluetooth, radio signals, WiFi, and/or analog and/or digital cellular format signals. This data may be processed and output in the form of a visual display that could be projected onto the retina, creating the perception of a digital heads-up display, for example how Google Glass employed this technology in an external device. For technology devices configured to sense biometric data (for example, but not limited to, glucose level, electrolyte level, basal metabolic rate, temperature, EEG, EKG, heart rate, intraocular pressure (e.g., for glaucoma patients or glaucoma candidates), ciliary muscle contraction, papillary construction or dilation, eye movement, blink rate, combinations thereof, and the like), the data could be collected by the technology device and transmitted wirelessly by the technology device to an external device configured to receive the data The electronic technology or the external device may be configured to process the data. For example, before transmission, the technology device may transform the data for privacy, security, data transfer efficiency, etc. The external device may be configured to process the data, for example because the external device may more easily be linked to a power source, cooled, etc. The external device can be configured to provide the data in a format that can be utilized in a health care decision. The data may be accessible by the wearer and/or a doctor or other healthcare professional, for example locally and/or through via a secure (e.g., HIPAA-compliant) network.

Another application of this technology could be use by people in environmentally challenging environments, for example intelligence agents, special forces soldiers, astronauts, police officers, and/or firefighters. Various sensors (e.g., external environmental sensors (e.g., for oxygen level, atmospheric pressure, temperature, infrared heat sensors) and/or internal biometric sensors (e.g., for oxygen level, temperature, heart rate, heart rhythm, glucose level, etc.) could be centrally assessed in an external computing device (e.g., a smartphone), and then transmitted to the intraocular lens to project information onto the retina in a dashboard type configuration. This information could be used to help them avoid danger and/or more effectively perform their duties. The technology could also be advantageous to performing any tasks that could benefit from a heads-up display such as surgery (e.g., recognition and labeling of anatomical structures), mechanical repair (e.g., recognition and labeling of mechanical elements), translation (e.g., from a first language to a second language), business identification (e.g., based on user ratings, health ratings, etc.), directions, design, etc.

Generally, as blood glucose increases, the refractive index of the aqueous humor increases, which is optically detectable. In an example implementation of an electronic device, a blood glucose monitor may comprise an optical detector configured to monitor the refractive index of the aqueous humor through the pupil, for example using an optical detector such as a camera. The refractive index may be correlated to blood glucose level via in situ electronics and/or raw data (e.g., images, histograms, etc.) may be transmitted to an external device configured to perform the correlation. The results may be available on and/or transmitted to an external device (e.g., smartphone, smartwatch), which could trigger an alarm if the blood glucose value is above and/or below certain thresholds. The blood glucose value can inform the user about the need to ingest sugar, take an insulin shot, etc. Other bodily parameters that can be measured in the eye include, but are not limited to, body temperature, heart rate, intraocular pressure, VEGF levels in macular degeneration patients, diabetic retinopathy, and retinal vein occlusion. One or all of these values may be visualizable on an external device (e.g., smartphone, smartwatch) and/or via an internal display system (e.g., a heads-up display).

The technology device can be used in combination with an intraocular lens. For example, the technology device can be used to control the properties of the intraocular lens (e.g., the refractive power, ultraviolet (UV) or visual light transmission properties of the IOL, etc.) and/or the properties of the prosthetic capsular device. For example, the technology device could be used to control the properties of a Calhoun adjustable lens (e.g., as described in U.S. Pat. No. 7,988,285, which is hereby incorporated by reference in its entirety), an Elenza lens (e.g., as described in further detail below), etc. When used in combination with an IOL, the technology device and the IOL may be positioned such that the technology device does not interfere with the sight lines of the IOL (e.g., the technology device does not block or interfere with light and images transmitted through the IOL and, ultimately, to the retina). The technology device may be around the outside perimeter edge of the intraocular lens. For example, two separate devices, (1) an IOL and (2) the technology device, may each be attached at the outer edge of the IOL. For another example, the IOL can be manufactured or adapted to have the technology device integral to the IOL at the outer perimeter edge of the IOL. If an IOL has a diameter of about 6 mm, a technology device having a width of about 2 mm may be added around the outer perimeter of the IOL, resulting in the IOL and technology device having a total diameter of about 10 mm. Such devices can vary in size, but the center is preferably at least about 1 mm to serve as the optic, and the entire device (technology device and optic) is preferably small enough to be implanted through an incision into the eye (e.g., the entire device may be similar in size to an IOL).

FIGS. 12A-12C illustrate example prosthetic capsular devices including technology devices and IOLs, and a manner of positioning the technology device and the IOL within a prosthetic capsular device. FIG. 12A shows a cross-section of a ring-like technology device 1202 inside a prosthetic capsular device 1200. FIG. 12A also depicts an IOL 1204 in the prosthetic capsular device 1200. FIG. 12B depicts a front view of an example intraocular lens 1250 usable in the example prosthetic capsular device 1200 shown in FIG. 12A in which the technology device 1202 surrounds the outer edge of the IOL 1250 (e.g., surrounds the outer edge of the optical surface of the IOL 1250). FIG. 12C depicts a top front perspective of the example intraocular lens 1250. The optical surface 1260 is not blocked by the technology device elements of the IOL 1250. The technology device 1202 includes an element 1252 for data output, an element 1254 for data input or receiving, and an element 1256 for data processing.

The prosthetic capsular device can comprise a material configured to shield the other internal eye structures from the small amount of heat or electromagnetic waves that might be generated by the technology device. Examples of such materials include silicone and silicone derivatives, acrylic, acrylic derivatives, collamer, biocompatible methacrylates (e.g., PMMA), biocompatible polymers, olefins (e.g., polypropylene), polyimide, combinations thereof (e.g., silicone and polyimide), and the like. A device comprising a thermally insulating material such as silicone, polyimide, acrylic, silicon dioxide, flexible glass, aerogels, combinations thereof (e.g., silicone and polyimide), and/or the like may be used to inhibit or prevent heat transfer due to conduction. Certain device dimensions can be increased to increase heat insulation, although injectability concerns may also be considered. A reflective and/or opaque material such as polyimide may be used to inhibit or prevent heat transfer due to radiation. Since the device is capsular, the device can be configured to shield (e.g., selectively shield) the ciliary body from heat. In some implementations, the prosthetic capsular device may comprise a combination of silicone and polyimide (e.g., polyimide overmolded on silicone).

The prosthetic capsular device can comprise a material or have a configuration configured to protect the interior of the eye from unwanted transmission of light. For example, the prosthetic capsular device can be designed to shield the posterior segment of the eye from UV light (for example, therapeutic UV light that is used in high concentration during procedures such as corneal cross-linking and in the refractive change that occurs through UV light modification of the Calhoun light adjustable lens). There are reports of retinal toxicity to UV exposure during these treatments because the pupil commonly dilates beyond the borders of the optic (e.g., greater than about 6 mm), and the UV filter coating on the posterior aspect of these lenses is prone to being rubbed off during folding and injecting, leaving the retina exposed to high doses of UV light transmittance through areas in which the coating is scratched off and around the outer border between the pupil edge and the rim of the IOL. By using a prosthetic capsular device which is about 10.5 mm in diameter, there would be no gap between the border of the iris and the IOL. Other sizes of prosthetic capsular devices can also provide UV benefits. Using established materials and methods well known in the art of intraocular lens manufacturing, the UV chromophore could be substantially incorporated into the material of the prosthetic capsular device so this property would not be susceptible to failure due to inadvertent mechanical removal (e.g., scratching and/or scraping off) during folding, insertion, and/or unfolding of the prosthetic capsular device.

The prosthetic capsular device can have a near-UV and UV blocking ability, which can protect the eye from energy or radiation in the form of near-UV or UV light emanating from the environment and utilized for therapeutic and refractive purposes. Intraocular lenses have been made with coatings that include UV blocking chromophores, which can suffer from scratching issues upon implantation and other issues, as described above. There are currently multiple ophthalmic therapies that utilize UV light as a treatment modality. For example, the Calhoun light adjustable lens (available from Calhoun Vision, Inc. of Pasadena, California) is an intraocular lens in which the refractive power can be changed post-operatively through the targeted application of near-UV and UV light of a specific wavelength for various time periods using a proprietary exposure algorithm. The back surface of the Calhoun light adjustable lens has a UV blocking layer, but that UV blocking layer is prone to being mechanically damaged (e.g., rubbed or scratched off) upon insertion of the lens, rendering the UV blocking layer potentially ineffective such that when the near-UV or UV light treatment is performed to adjust the lens power post-operatively, the patients are prone to near-UV and UV radiation exposure related complications to the contents of the posterior segment (ciliary body, retina, optic nerve, etc.). The diameter of the Calhoun lens optic is 6.0 mm, which for many patients is smaller than the dilated pupil such that UV light may pass by the edges of the lens. For these patients, applying a wide beam of near-UV or UV light to the lens has the potential to cause UV radiation exposure related complications to the contents of the posterior segment (ciliary body, retina, optic nerve, etc.). If this light adjustable lens is placed inside a prosthetic capsular device that is larger or much larger than the dilated pupil and that has the ability to block near-UV and UV light, there could be a reduced likelihood of UV radiation related complications during the post-operative treatment.

In some implementations, a capacitor, series of capacitors, and/or a rechargeable battery that can be recharged by a device from outside the eye (such as by external induction) may supply power to the technology device. The battery changer could be incorporated into a sleeping device such as a facemask, pillow, mattress, or bed linen to charge the battery during a user's sleep, sunglasses, a headband, or a hat to charge the battery while the user is outdoors, and/or spectacle frames or other appropriate devices for when the user is indoors. Preferably, the transfer of electricity to power a technology device either directly or through the charging of a battery is via an inductive charging system such as through resonant inductive coupling. For example, the external device could contain an induction coil and would be connected to a power source in order to generate an alternating electromagnetic field, and the technology device could contain a second induction coil configured to harness power from the alternating electromagnetic field generated by the external device and to convert the power into electricity to charge the battery. The prosthetic capsular device can be designed to shield the posterior segment structures, such as the iris, zonules, ciliary body, ciliary process, etc., from heat generated by the charging of batteries through external induction, or the discharge of heat generated by a technology device, for example using certain materials and techniques as described above. Increased local temperatures can result in inflammation and uveitis, and ultimately limit the biocompatibility of technology device. Utilizing a prosthetic capsular device having optical clarity and with thermal insulating properties (e.g., comprising silicone, silicone derivatives, polyimide, combinations thereof, the like, and/or other appropriate materials) could provide appropriate thermal insulation without adversely affecting visual function.

The prosthetic capsular device can be designed to be photo-responsive so as to shield the retina from unwanted light, which could provide a number of uses.

For a first example, people with chronic light-sensitivity may want a permanent decrease in the light transmitted. This would function like permanent internal sunglasses. A light blocking chromophore of any and all various wavelengths, and of any and all densities of transmission could be added to the material formulation, baked into material, contained in a film that can be layered and bonded to the prosthetic capsular device, and/or absorbed/adsorbed into/onto the prosthetic capsular device.

For a second example, people might want to have a device in the eye that darkens in the light and becomes more clear/transparent in the dark (photogrey, photobrown). Photochromatic materials (e.g., silver chloride, silver halide), which change shape and light absorption profile in response to the presence or absence of UV light, could be added to the material formulation, baked into material, contained in a film that can be layered and bonded to the prosthetic capsular device, and/or absorbed/adsorbed into/onto the prosthetic capsular device. Photochromatic materials may be combined with light blocking chromophores.

For a third example, people might want to take advantage of the pinhole effect that can be created by using a small aperture. This can be achieved by darkening all but the central 1-2 mm (approximately) of the prosthetic capsular device. This effect could be permanent (e.g., comprising an opaque annular mask (e.g., comprising polyvinylidene fluoride (PVDF) and carbon nanoparticles) embedded in and/or on one or both surfaces of the refractive portion) or transient (e.g., using a color shifting and/or liquid crystal technology to create an annular mask that is opaque or has reduced transmittance). The mask could have an outer diameter between about 3 mm and about 3.5 mm (e.g., about 3.25 mm). The mask could have an inner diameter between about 1 mm and about 1.5 mm (e.g., about 1.35 mm). The mask could have a thickness between about 4 µm and about 6 µm (e.g., about 5 µm), although thickness may vary based on the number of masks. The mask may comprise a plurality of microperforations, for example small enough to not allow substantial light passage or to create diffractive dispersion, but removing enough material to increase flexibility of the mask. In good lighting, the patient would be able to read due to the transient pinhole effect that would be created. In low lighting, the pinhole effect would be removed. Such a device could improve near and intermediate vision, increase depth of focus (e.g., by at least about 1.5 D), maintain good distance vision, inhibit creation of competing focal points, glare, halos, night-vision problems, double vision, ghosting, etc., maintain binocularity for distance, and/or maintain binocular contrast sensitivity.

In certain non-limiting examples, the prosthetic capsular devices described herein could perform one or more of the following functions: provide a protected prosthetic receptacle having refractive properties, for an intraocular electronic technology device having the ability to send and receive wireless data, and/or interact with internal or external controls through external eye movements, pupil movement, ciliary body contraction, voice, and/or controls from other prostheses (contacts, glasses, computer screens, projectors); provide a protected prosthetic receptacle for battery storage, designed to power electronic intraocular technology; provide a protected prosthetic receptacle for an electric powered accommodating intraocular lens (such as the Elenza lens); and/or provide a protected prosthetic receptacle for the repair or replacement of intraocular technology including traditional lenses, and electric powered devices as described above.

Referring again to FIGS. 4B-4G and the description of example animal study procedures, FIGS. 13A-23E are photographs of results of an animal study conducted along the same lines. In five rabbits, a prosthetic capsular device 400 as shown in FIGS. 4G-4I and described above, and then an IOL (AcrySof SN60AT, a single-piece hydrophobic acrylic IOL manufactured by Alcon) were inserted into the right eye of each rabbit, and only an IOL was inserted into the left eye of each rabbit. The procedure for the prosthetic capsular device and IOL eyes was as described above, and the procedure for the IOL-only eyes was substantially the same without the prosthetic capsular device steps.

Figure 13A:
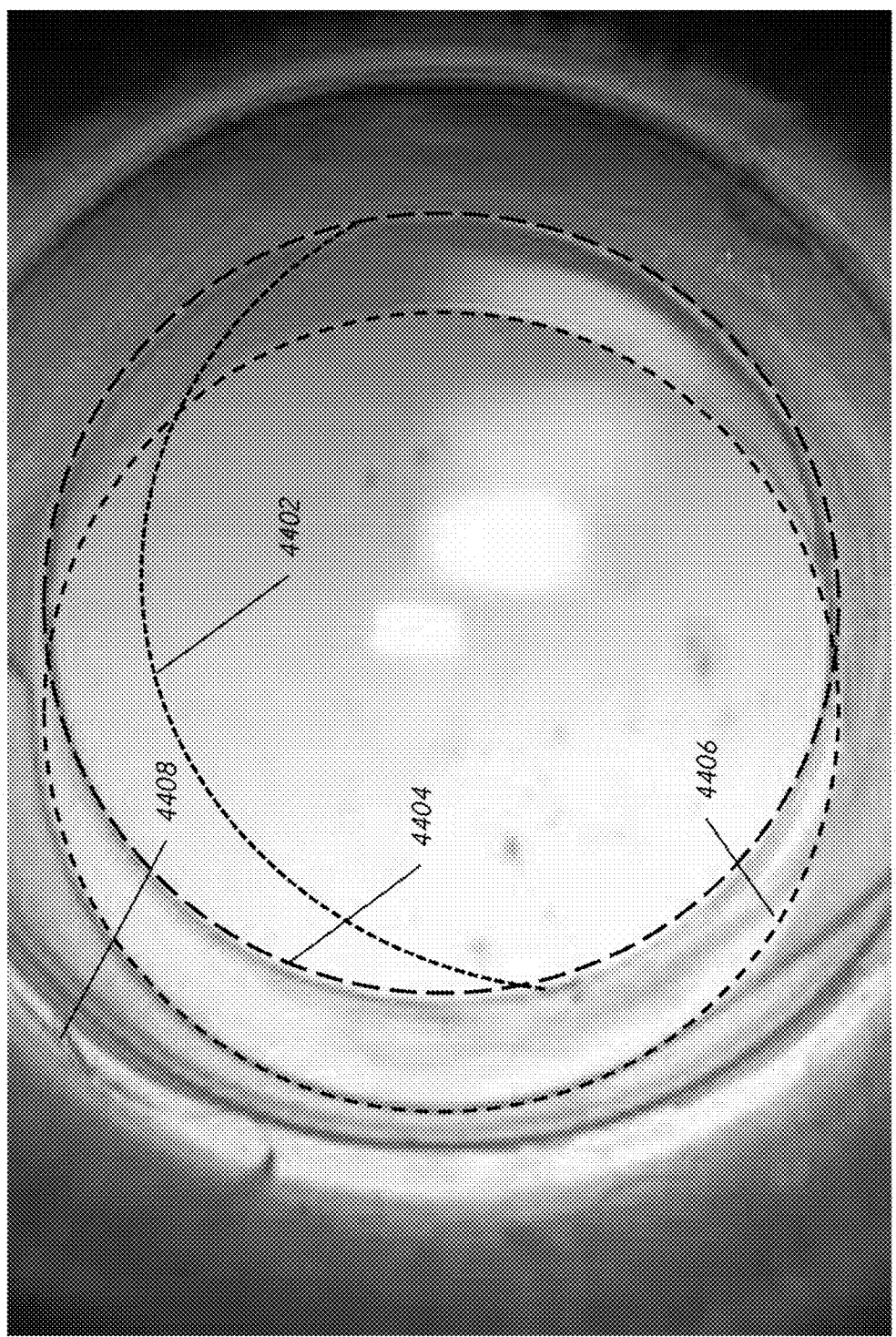
FIGS. 13A and 13B are photographs of animal study results annotated to highlight certain features.
Figure 13B:
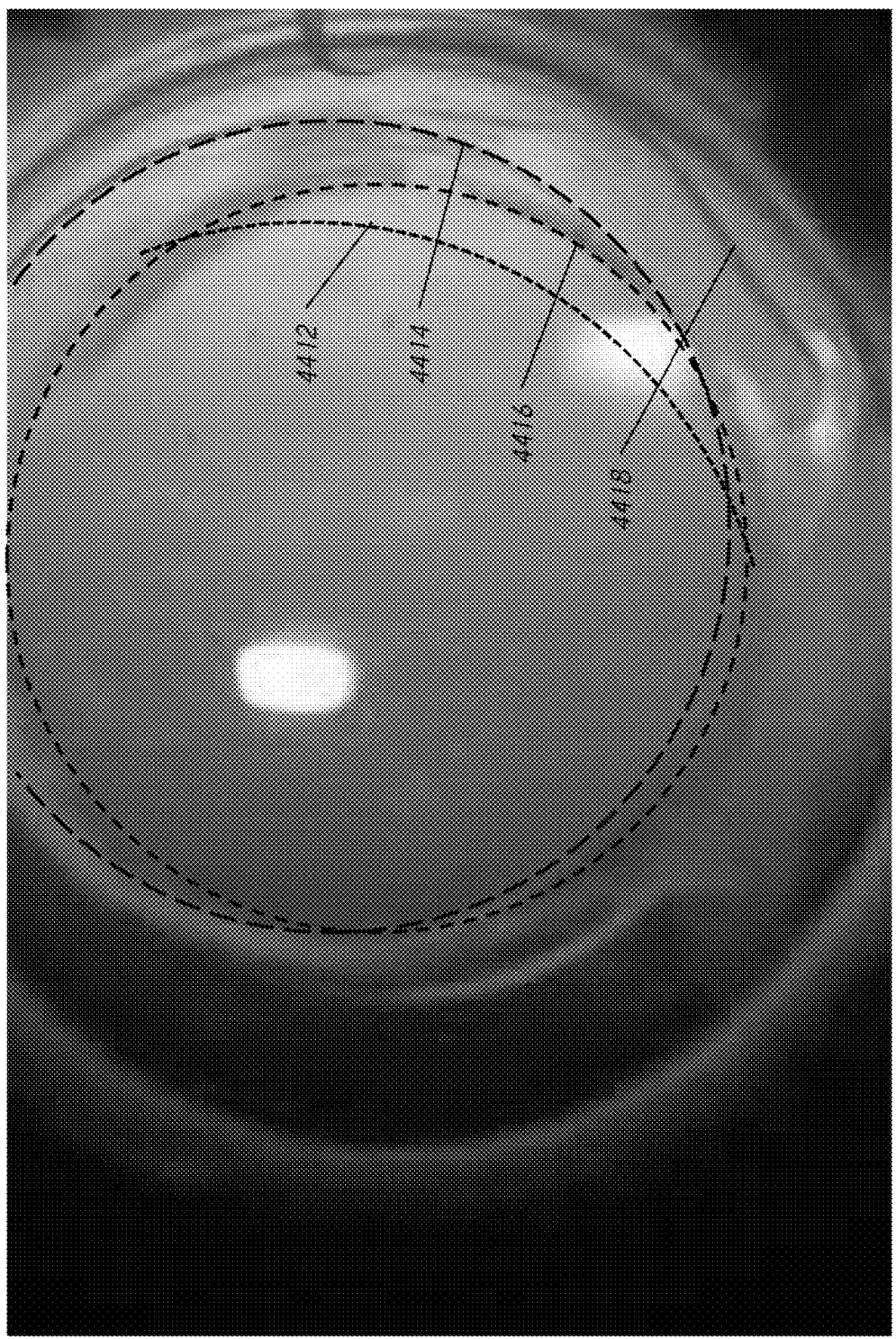

FIGS. 13A and 13B are photographs of animal study results annotated to highlight certain features. Since the location, shading, coloration, etc. can vary based on variations in device location, lighting, anatomy, and the like, FIGS. 13A and 13B are somewhat redundantly provided to provide the reader with the ability to identify the identified features in the variety of photographs described below. In FIGS. 14A-23C, four photographs are provided for each figure with different lighting conditions, focal points, angles, etc. to provide at least one figure illustrative of the condition of the eye; however, the photographs in each figure are of the same eye at the same time (e.g., after one week, after two weeks, after three weeks, or after four weeks).

Figure 18A:
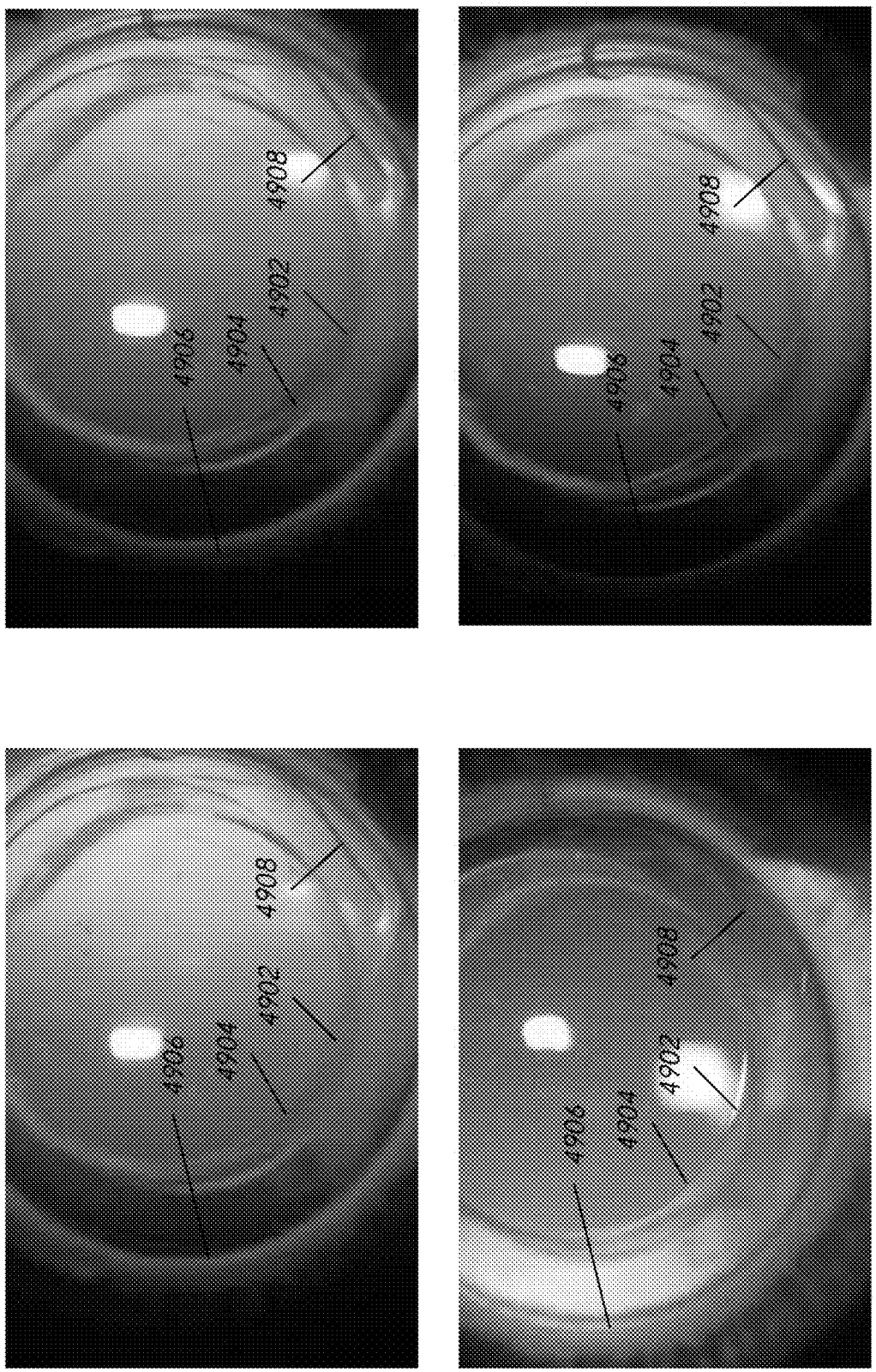
Figure 18B:
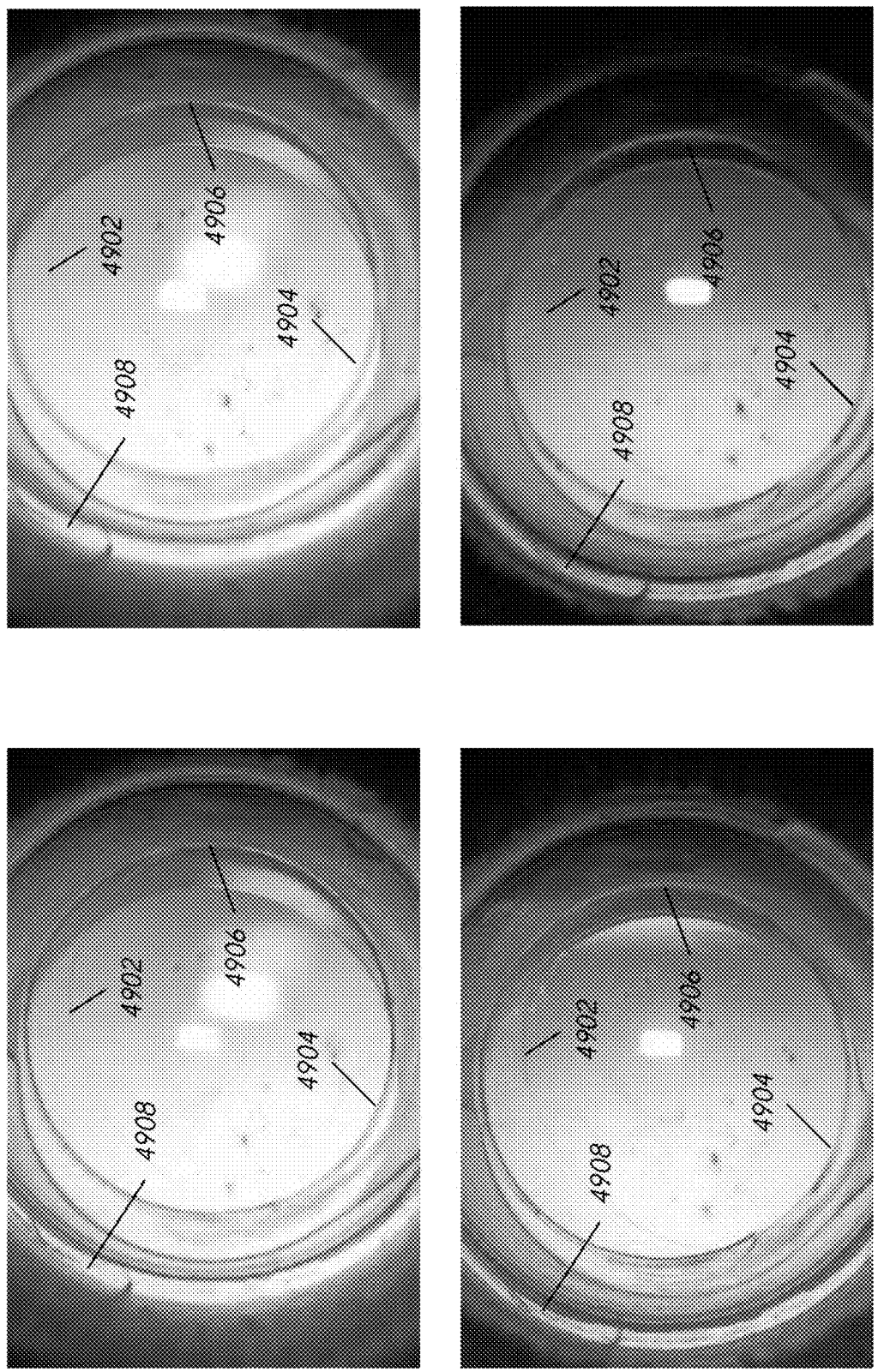

FIG. 13A, which is an annotated version of FIG. 18B (upper left photograph), illustrates an anterior capsulorhexis 4402 (shown by short dashes), a refractive surface 4404 (shown by long dashes) of an IOL, an anterior opening 4406 (shown by intermediate dashes) of a prosthetic capsular device containing the IOL, and IOL haptics 4408. FIG. 13B, which is an annotated version of FIG. 18A (upper right photograph), illustrates an anterior capsulorhexis 4412 (shown by short dashes), a refractive surface 4414 (shown by long dashes) of an IOL, an anterior opening 4416 (shown by intermediate dashes) of a prosthetic capsular device containing the IOL, and IOL haptics 4418. Photographs of eyes used for control (e.g., consisting essentially of an IOL) do not show an anterior opening of a prosthetic capsular device.

Rabbit eyes are highly inflammatory such that each week in a rabbit is approximately six months in a human. Four weeks in a rabbit, the last two sets of photographs in each figure set (i.e., "D" and "E"), is substantially equivalent to the effects after approximately two years in a human.

Figure 14A:
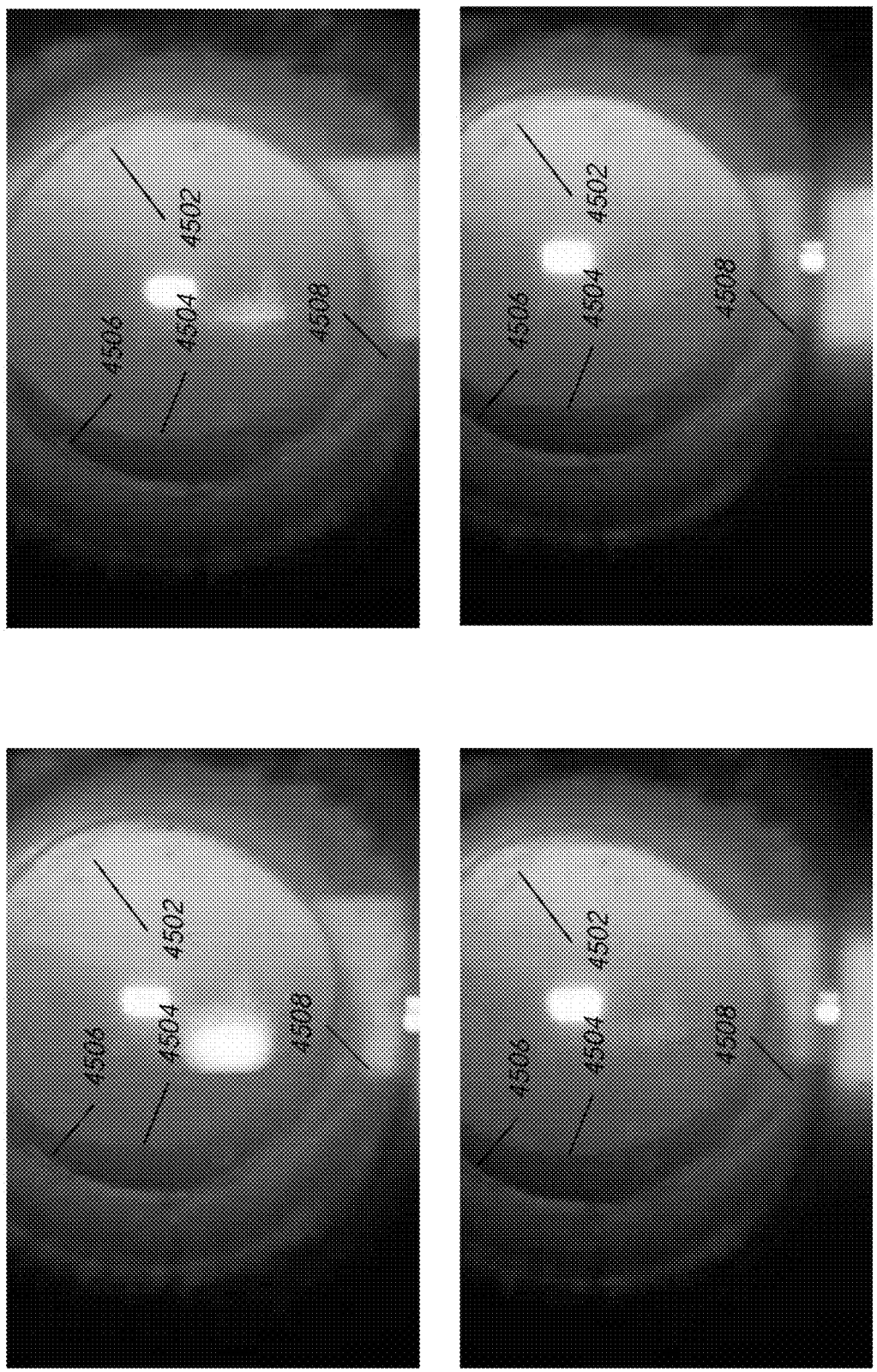
Figure 14E:
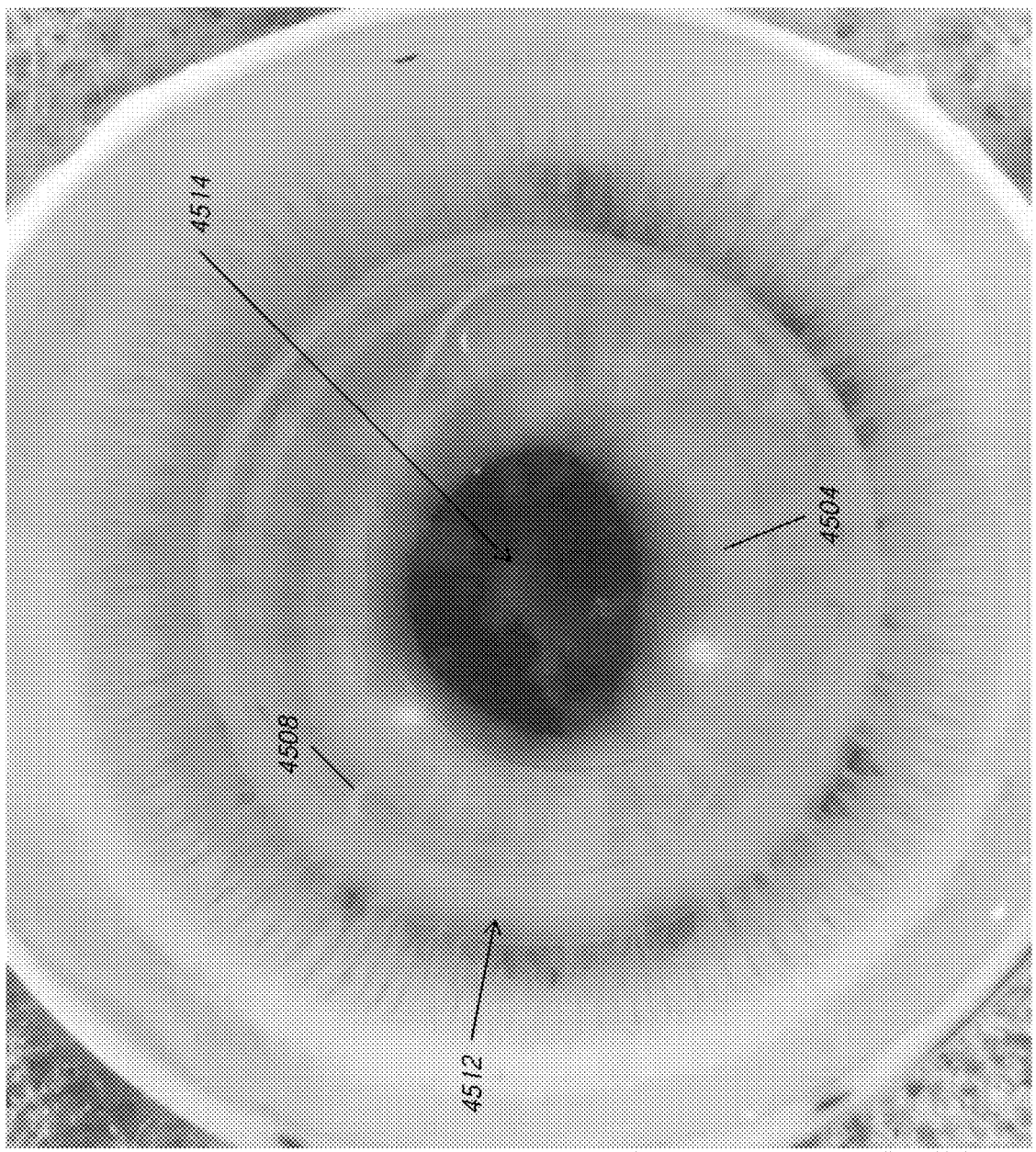

FIGS. 14A-14E are photographs of animal study results for a right eye of a first rabbit. FIG. 14A is after one week, FIG. 14B is after two weeks, FIG. 14C is after three weeks, and FIGS. 14D and 14E are after four weeks. FIGS. 14A-14E illustrate an anterior capsulorhexis 4502, a refractive surface 4504 of an IOL, an anterior opening 4506 of a prosthetic capsular device containing the IOL, and IOL haptics 4508. The IOL haptics 4508 are not visible in some figures, although the position of the haptics may be assumed based on other figures and/or the position of any visible portions of the IOL flared radially outwardly to form the start of the haptics.

As described above, the natural capsular bag undergoes chronic changes after cataract surgery believed to be largely due to the presence and continued growth of epithelial cells remaining on the natural capsular bag. If the entire natural capsular bag becomes fibrotic, and phimosis persists, there can be zonular dehiscence and changes to the effective lens position over time. Significant opacification of the natural capsular bag may be remedied by a Nd:YAG laser posterior capsulotomy. FIGS. 14A-14C show that epithelial cell migration and propagation has been successfully mediated by use of the prosthetic capsular device. Even after four weeks, the natural capsular bag is substantially free of PCO, which is best seen by comparison to FIGS. 15A-15D, which show the left eye of the same rabbit during the same time periods. Without being bound by any particular theory, the Applicant believes that the prosthetic capsular device filling or substantially filling the natural space or volume of the natural capsular bag inhibits or prevents PCO.

FIG. 14B shows a small tear 4510 in the prosthetic capsular device at approximately a 9 o'clock position. Even with this small defect, which was not present in the other four eyes containing a prosthetic capsular device and which is not believed to be a chronic problem, no irritation or opacification is evidenced in eyes containing a prosthetic capsular device. The eyes containing a prosthetic capsular device show some irritation of the vitreous.

FIG. 14E shows a Soemmering's ring 4512 and material 4514 on a posterior surface of the IOL. The Soemmering's ring 4512 is a toroidal collection of lens epithelial cells that have transformed and grown after the cataract has been removed. This occurs in the natural capsular bag after removal of the natural lens as a result of mesenchymal epithelial transformation thought to be caused by a combination of inflammatory mediators and contact between the anterior capsule and the posterior capsule.

Figure 15A:
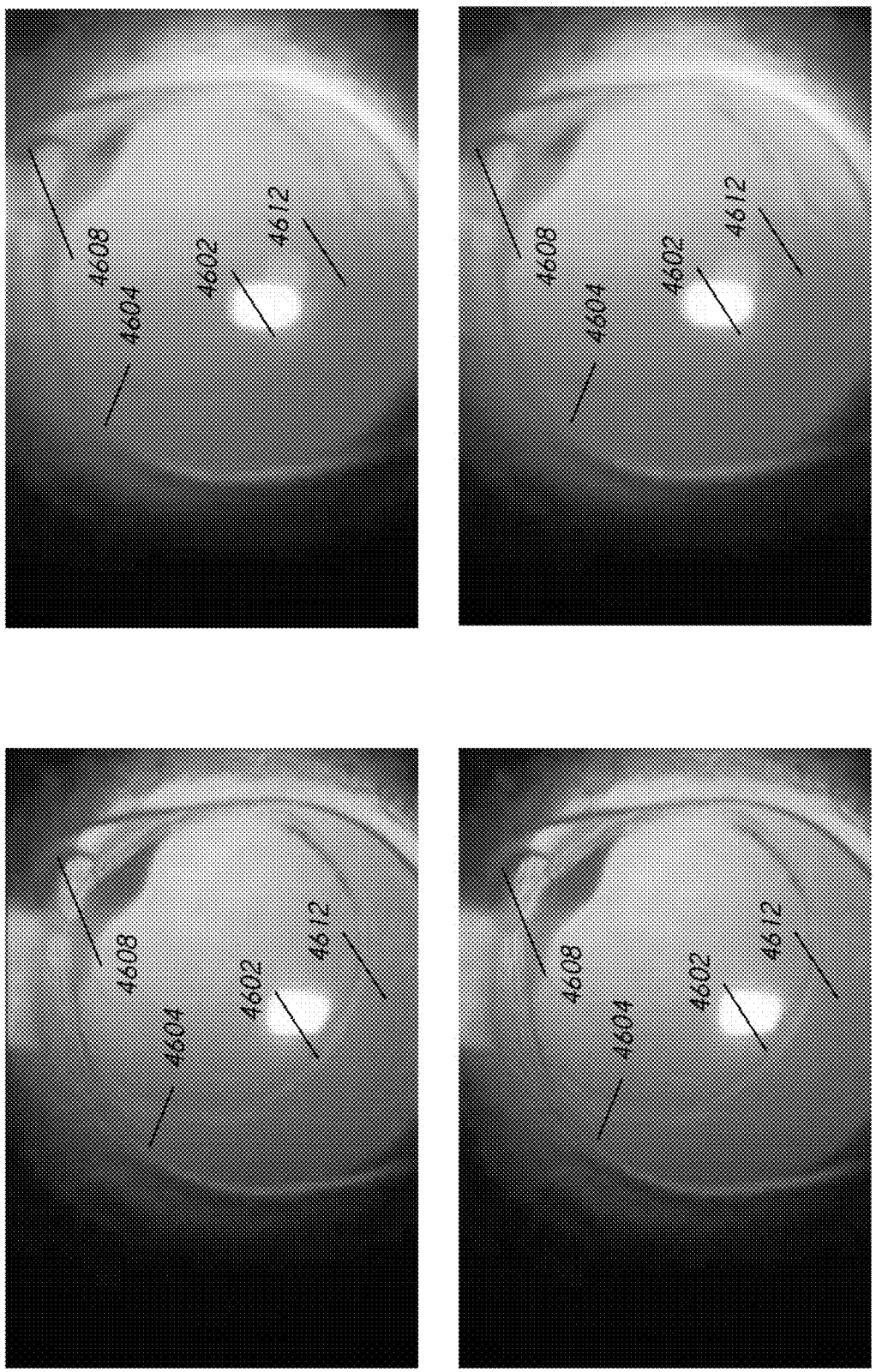
Figure 15B:
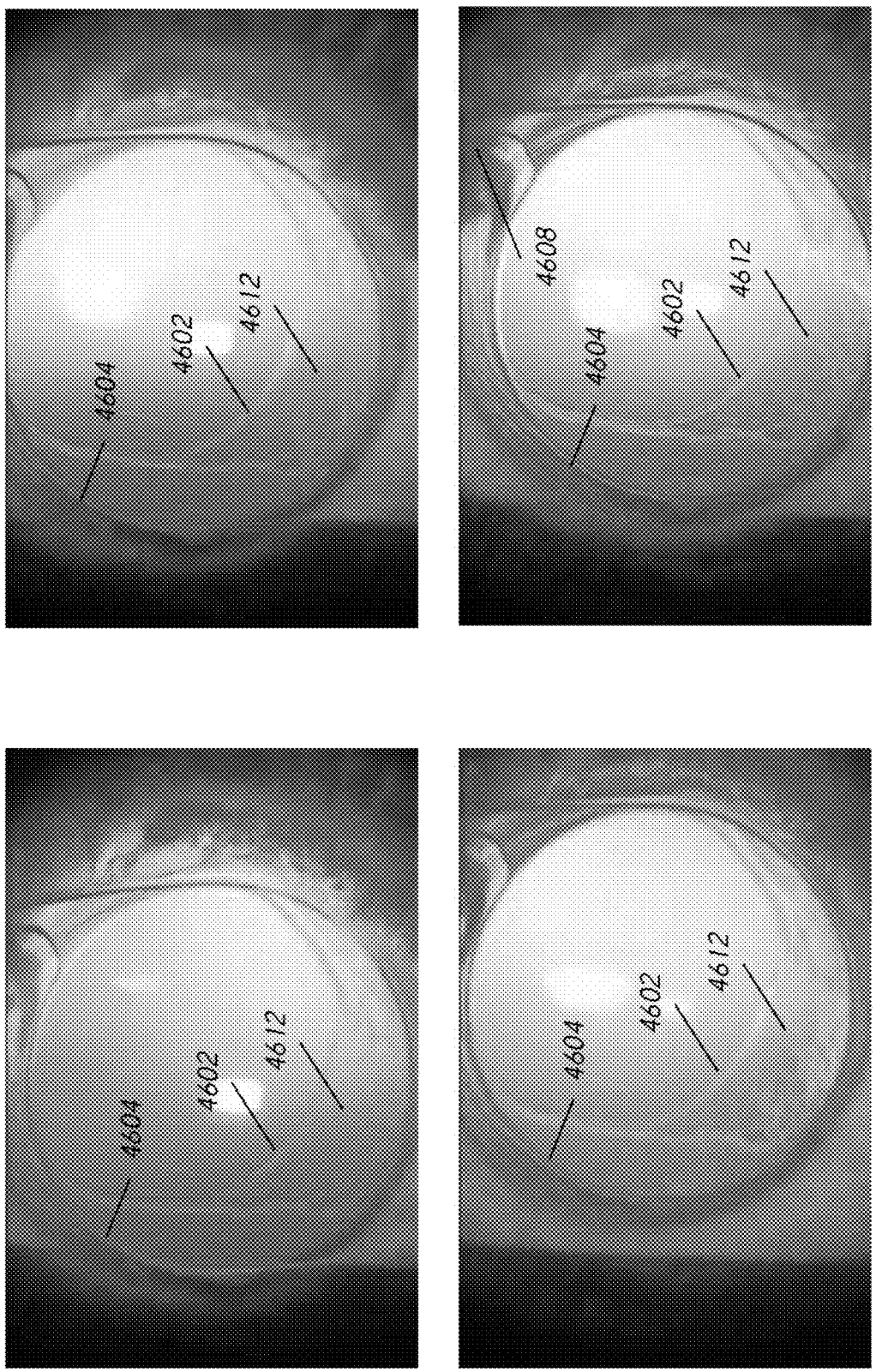
Figure 15D:
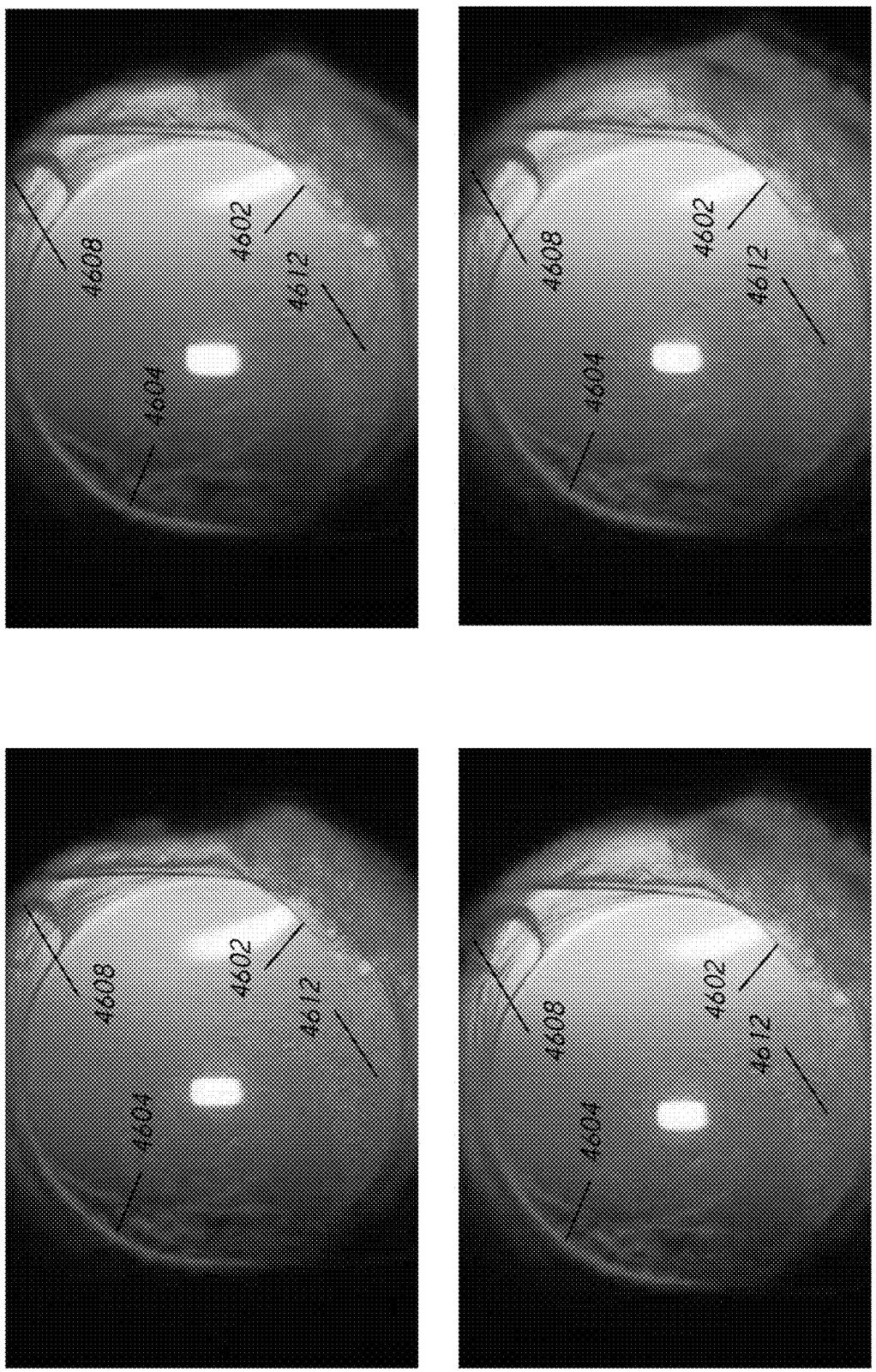
Figure 15E:
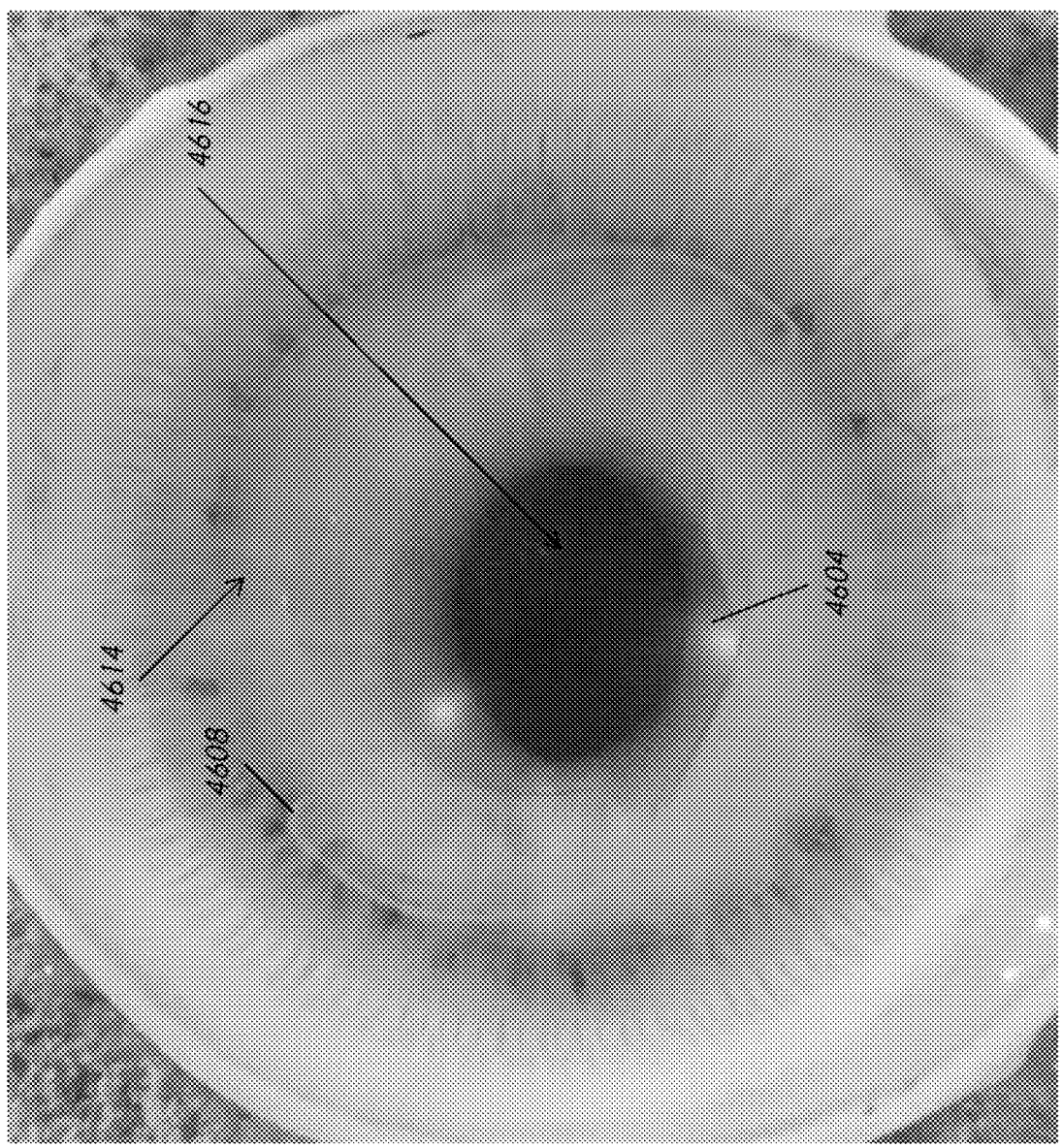

FIGS. 15A-15E are photographs of animal study results for a left eye of the first rabbit. FIG. 15A is after one week, FIG. 15B is after two weeks, FIG. 15C is after three weeks, and FIGS. 15D and 15E are after four weeks. FIGS. 15A-15E illustrate an anterior capsulorhexis 4602, a refractive surface 4604 of an IOL, and IOL haptics 4608. The IOL haptics 4608 are not visible in some figures, although the position of the haptics may be assumed based on other figures and/or the position of any visible portions of the IOL flared radially outwardly to form the start of the haptics.

The first easily identifiable difference between the right eye of FIGS. 14A-14D and the left eye of FIGS. 15A-15D is the significant fibrosis 4612 of the natural capsular bag, even after only two weeks (FIG. 15B). Fibrosis, the epithelial-mesenchymal transition of the lens epithelial cells to muscle cells (or contractile tissue or myofibroblast tissue), can cause opacification and/or can increase the elasticity of the natural capsular bag, which can cause contraction. Each are undesirable, but in combination, contraction and opacification can reduce an amount of light that can pass through the eye to the retina, reducing vision.

A normal eye under normal lighting conditions takes in light between about 3 mm and about 6 mm. Under bright light conditions, the normal eye may reduce light intake to between about 1 mm and about 2 mm. Under low light conditions, the normal eye may increase light intake to between about 7 mm and about 8 mm. Due to the contraction and fibrosis, the effective diameter at which the left eye of FIGS. 15A-15D can take in light is about 4.1 mm, which significantly impairs the vision in that eye except under the best lighting conditions. The effective diameters provided herein are rough approximations based on the photographs, but are precise enough to show visual impairment.

The second easily identifiable difference between the right eye of FIGS. 14A-14D and the left eye of FIGS. 15A-15D is the migration or shifting of the position of the IOL. The last figure ("E") for each set of eye figures, which is a gross section, best shows the centering of the IOL. The IOLs in the right eyes, which also include a prosthetic capsular device, were generally more centered and sat more posterior than the IOLs in the left eyes, in which the IOL is more flat in line with the collapsed natural capsular bag.

FIG. 15E shows a Soemmering's ring 4614 and the inception of PCO 4616. As described in further detail herein, PCO is the formation of a partially opaque membrane by the reproduction of lens epithelial cells along the posterior of the natural capsular bag. In contrast, material on the posterior surface, for example as described with respect to FIG. 14E, is most likely retrained viscoelastic that has some residual trapped fibrin or inflammatory precipitate contained within it.

Figure 16A:
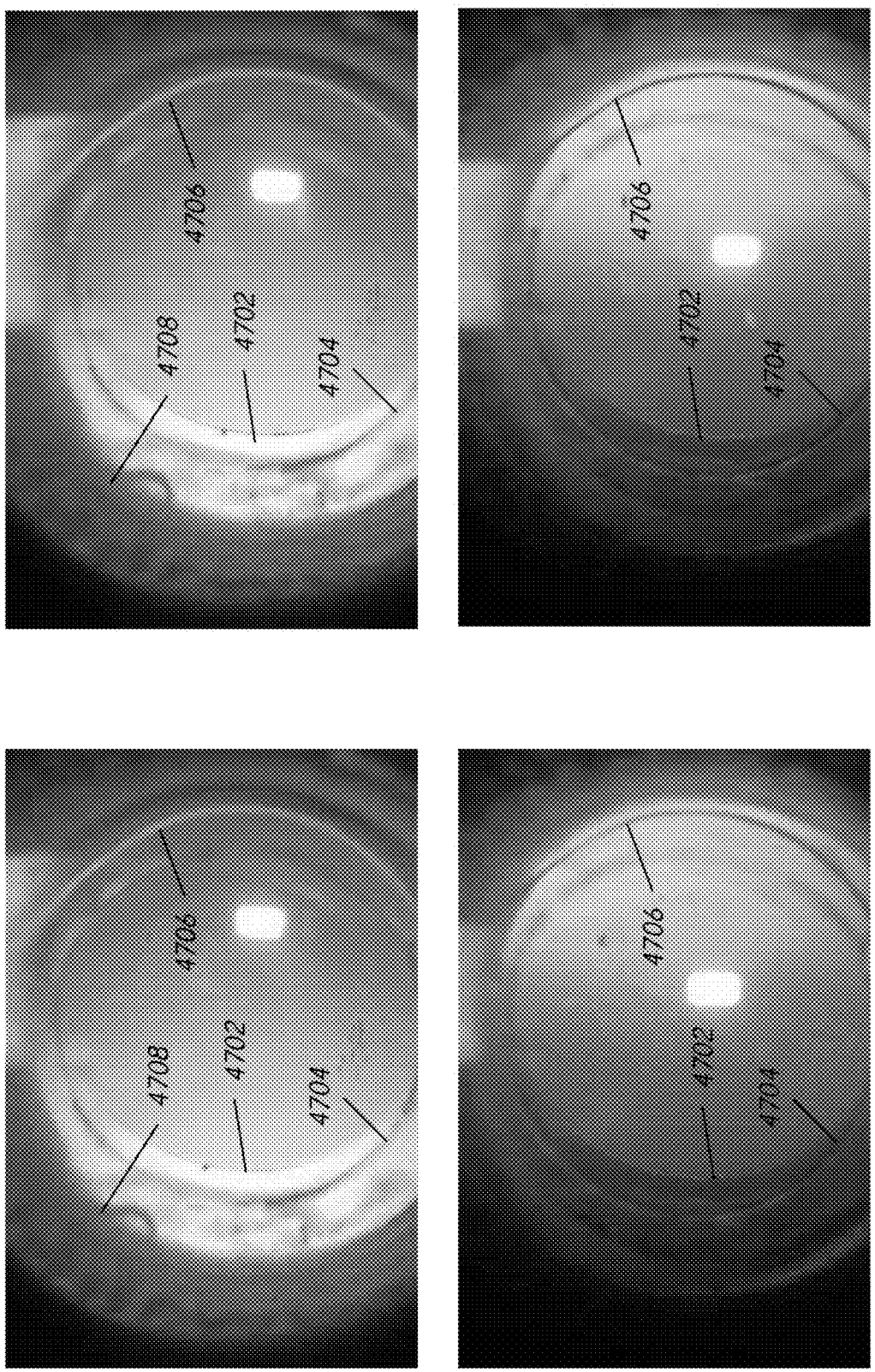
Figure 16C:
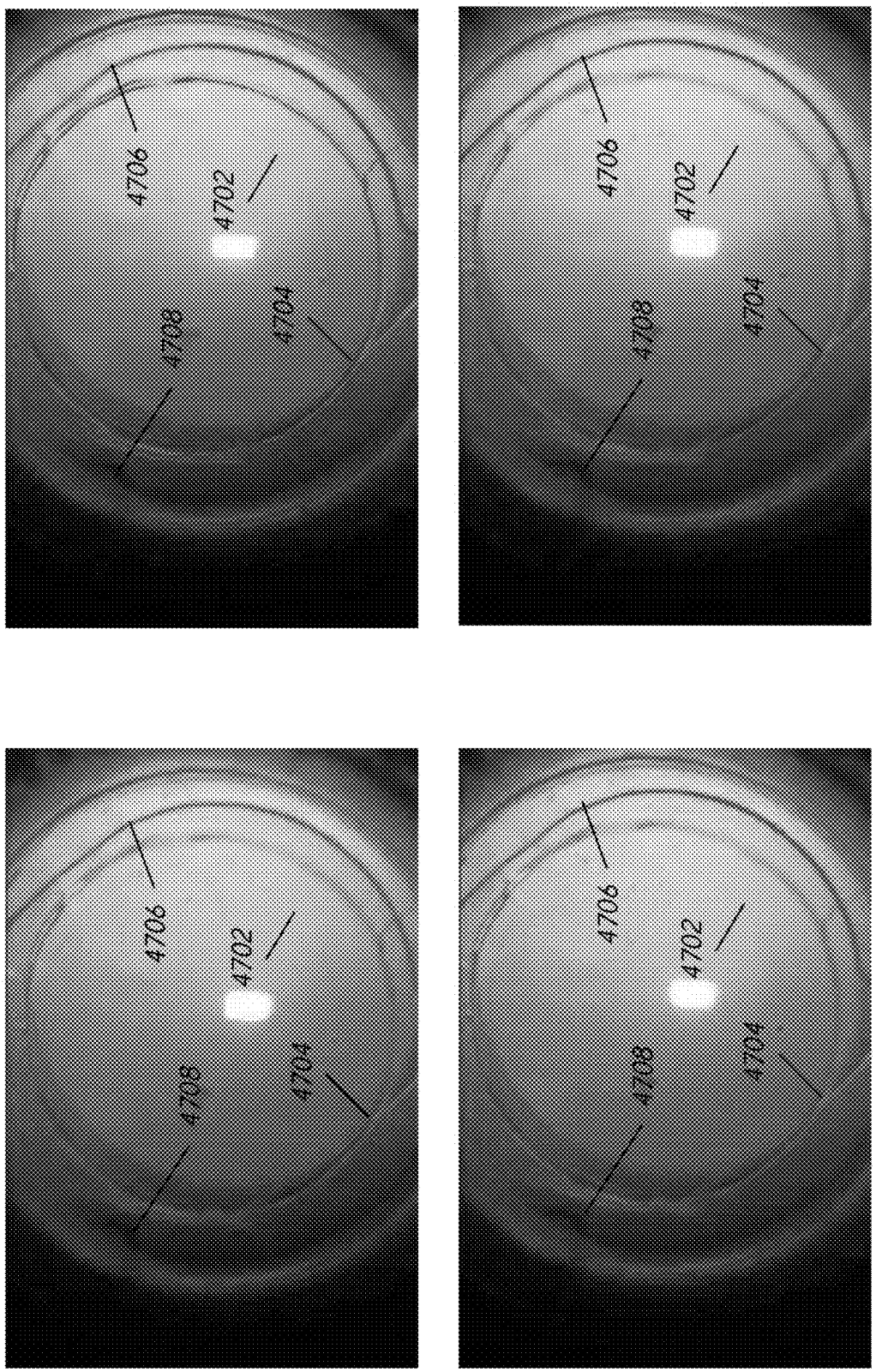
Figure 16D:
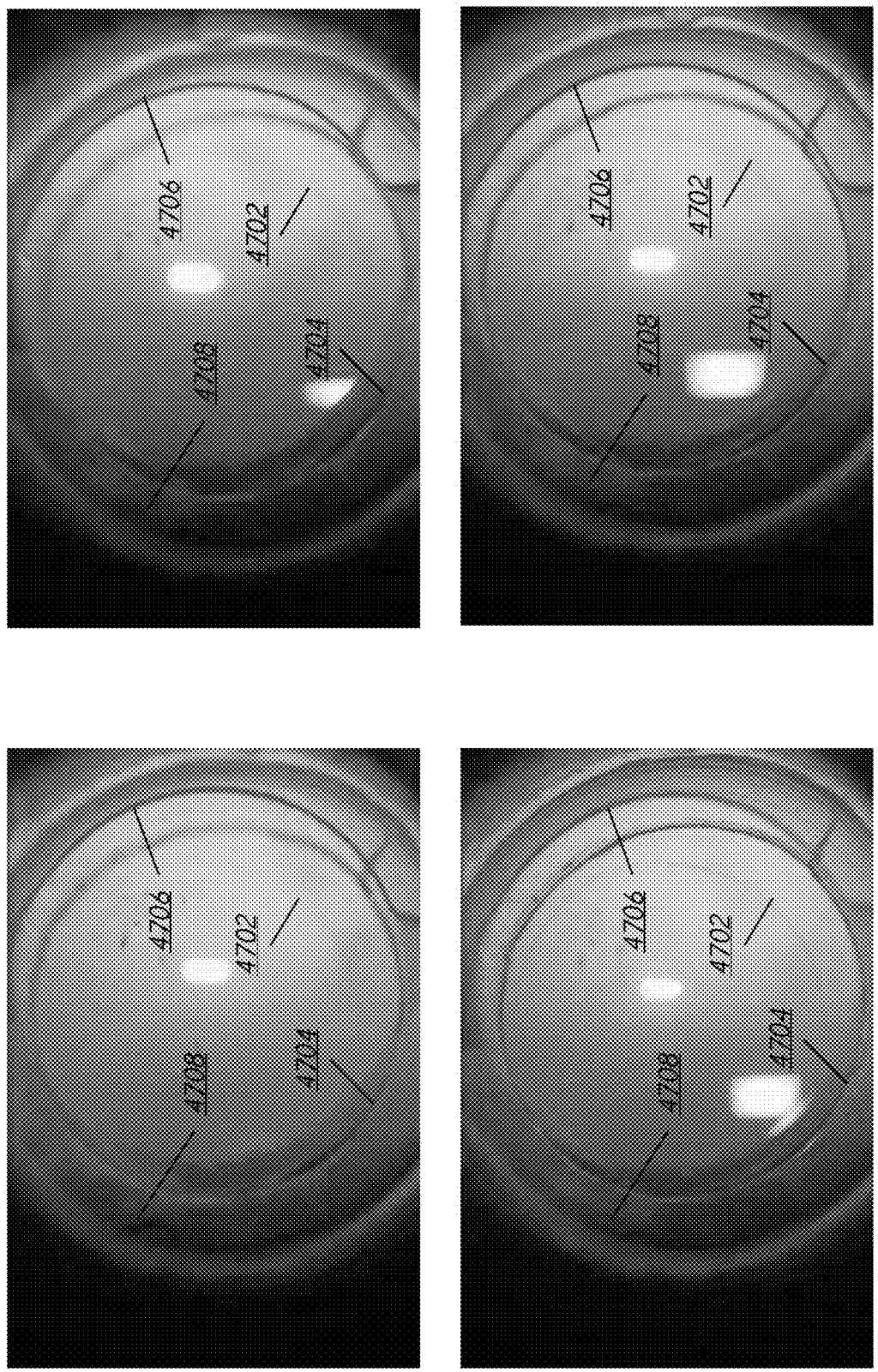
Figure 16E:
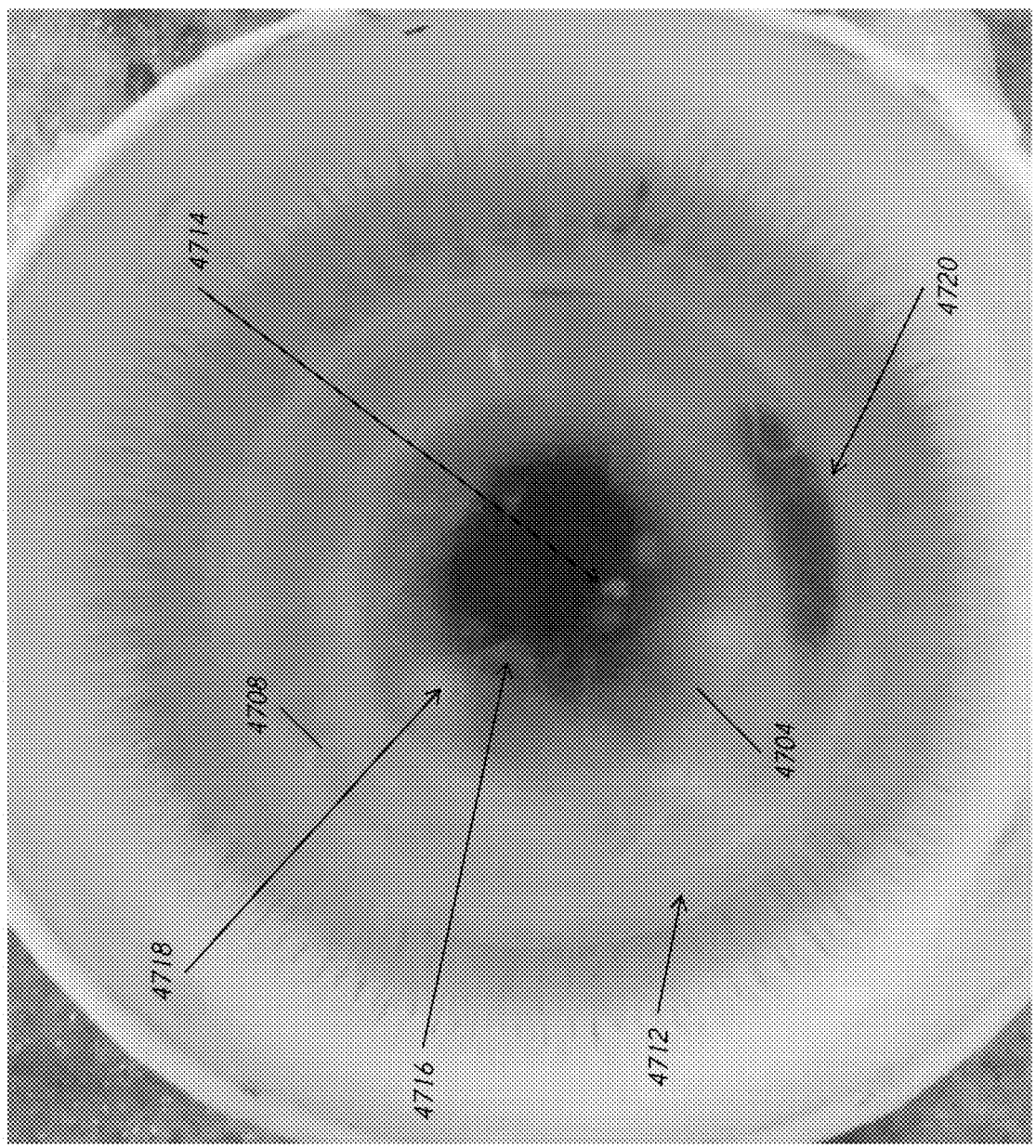

FIGS. 16A-16E are photographs of animal study results for a right eye of a second rabbit. FIG. 16A is after one week, FIG. 16B is after two weeks, FIG. 16C is after three weeks, and FIGS. 16D and 16E are after four weeks. FIGS. 16A-16E illustrate an anterior capsulorhexis 4702, a refractive surface 4704 of an IOL, an anterior opening 4706 of a prosthetic capsular device containing the IOL, and IOL haptics 4708. The IOL haptics 4708 are not visible in some figures, although the position of the haptics may be assumed based on other figures and/or the position of any visible portions of the IOL flared radially outwardly to form the start of the haptics. The IOL is well centered in the prosthetic capsular device, which can be seen by the positions of the refractive surface 4704 of the IOL and the anterior opening 4706 of the prosthetic capsular device. In contrast to FIGS. 14A-14D, FIGS. 16A-16D, as well as FIGS. 18A-18D, 20A-20D, and 22A-22D, show that the prosthetic capsular device was not torn, which is generally preferably even though tearing did not cause irritation in the eye of the first rabbit. The natural capsular bag is substantially free of fibrosis.

FIG. 16E shows a Soemmering's ring 4712, material 4714 on the posterior surface of the IOL, material 4716 attached to the posterior capsule at the vitreous face, and the inception of peripheral PCO 4718. FIG. 16E also shows a mild reaction in the anterior vitreous with some small clumps of lymphocytes 4720 in the anterior vitreous, indicative of a low-grade vitritis.

Figure 17A:
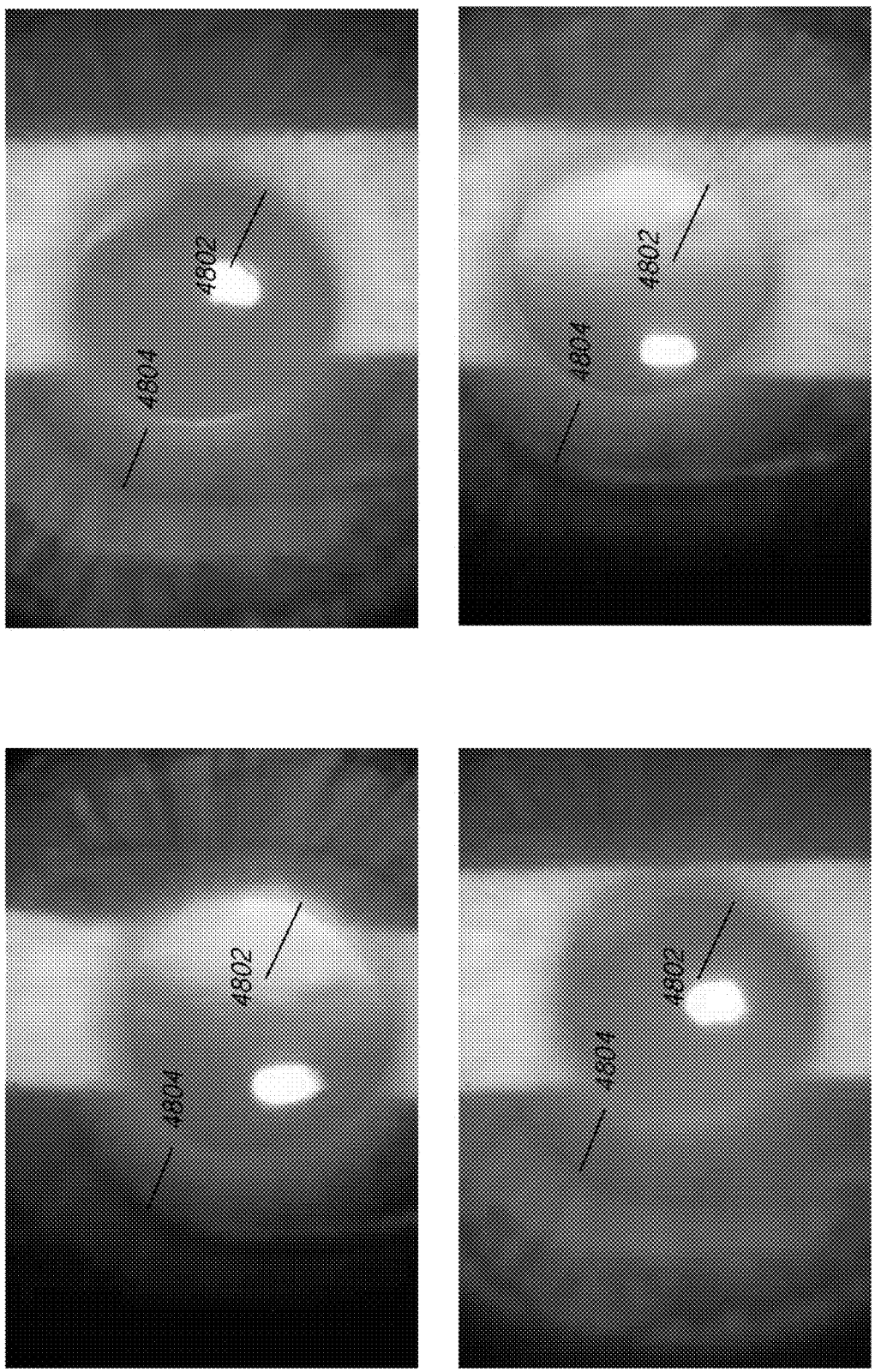
Figure 17B:
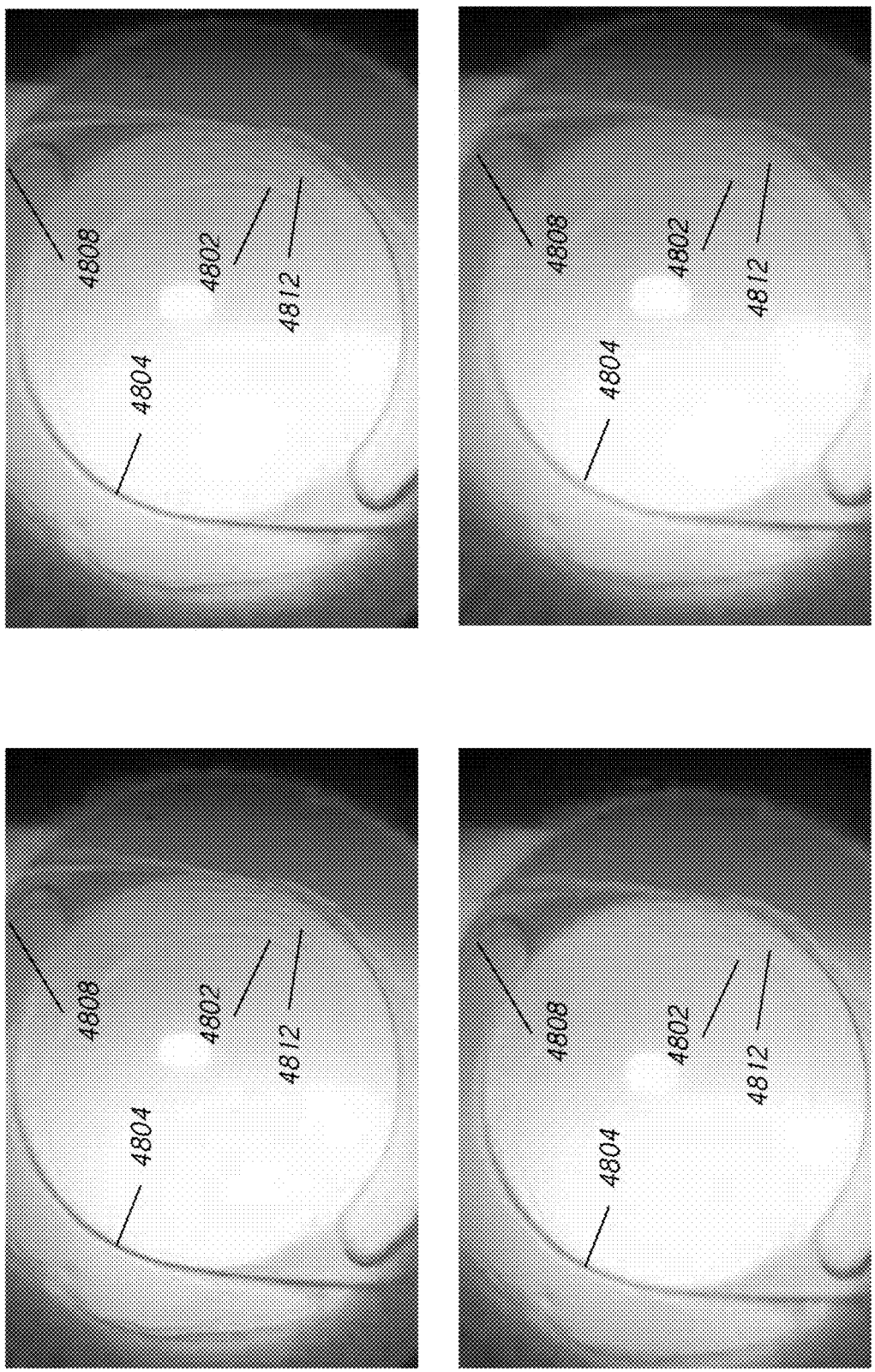
Figure 17E:
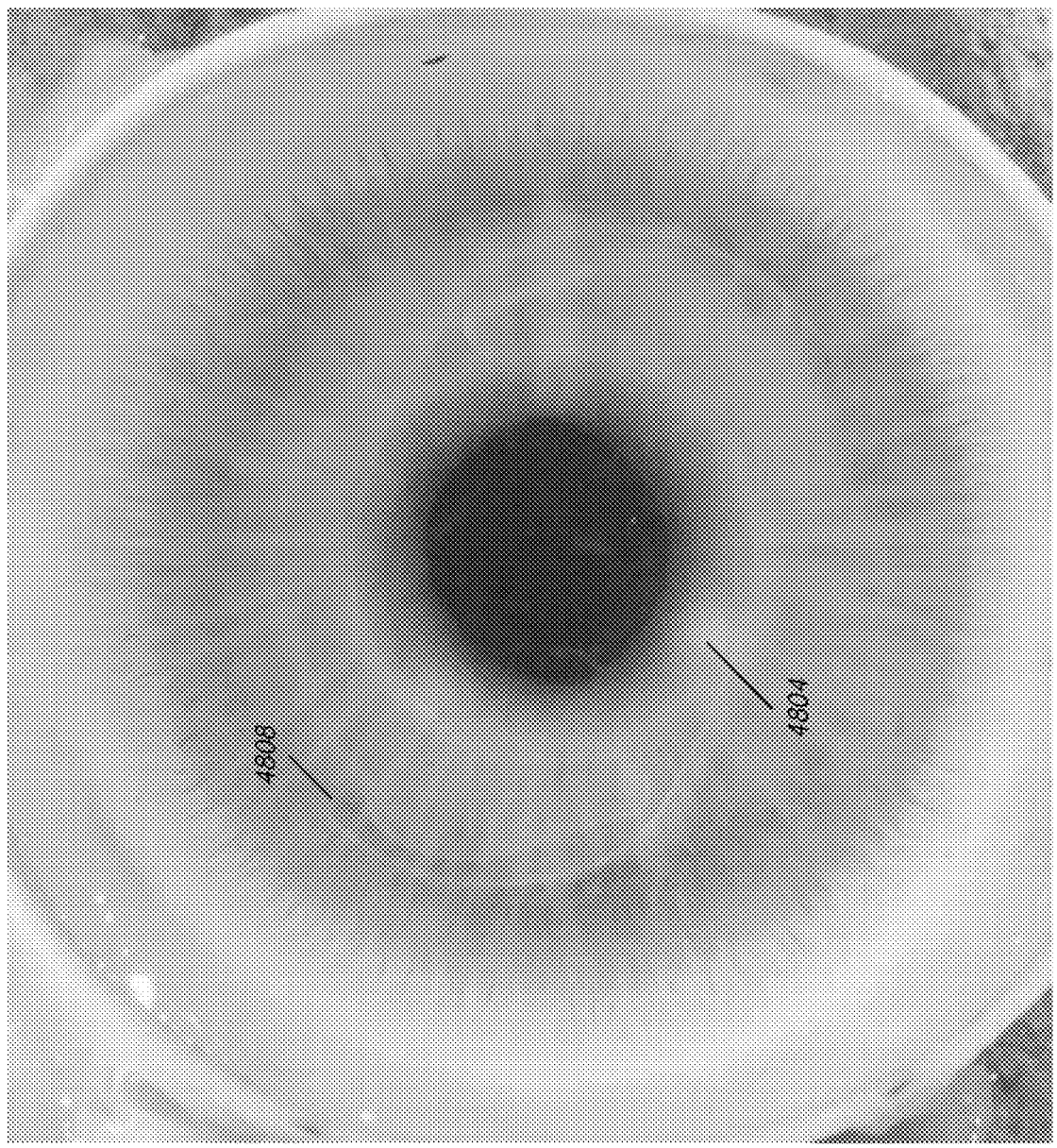

FIGS. 17A-17E are photographs of animal study results for a left eye of the second rabbit. FIG. 17A is after one week, FIG. 17B is after two weeks, FIG. 17C is after three weeks, and FIGS. 17D and 17E are after four weeks. FIGS. 17A-17E illustrate an anterior capsulorhexis 4802, a refractive surface 4804 of an IOL, and IOL haptics 4808. The IOL haptics 4808 are not visible in some figures, although the position of the haptics may be assumed based on other figures and/or the position of any visible portions of the IOL flared radially outwardly to form the start of the haptics. As in FIGS. 46A-46E, and in stark contrast to the right eye of FIGS. 16A-16E, the left eye of FIGS. 17A-17E evidence significant fibrosis 4812 of the natural capsular bag, best seen in FIG. 17C. FIGS. 15A-15E also shown contraction of the anterior capsulorhexis 4802. Due to the contraction and fibrosis, the effective diameter at which the left eye of FIGS. 17A-17E can take in light is about 4.3 mm, which significantly impairs the vision in that eye except under the best lighting conditions.

Figure 18D:
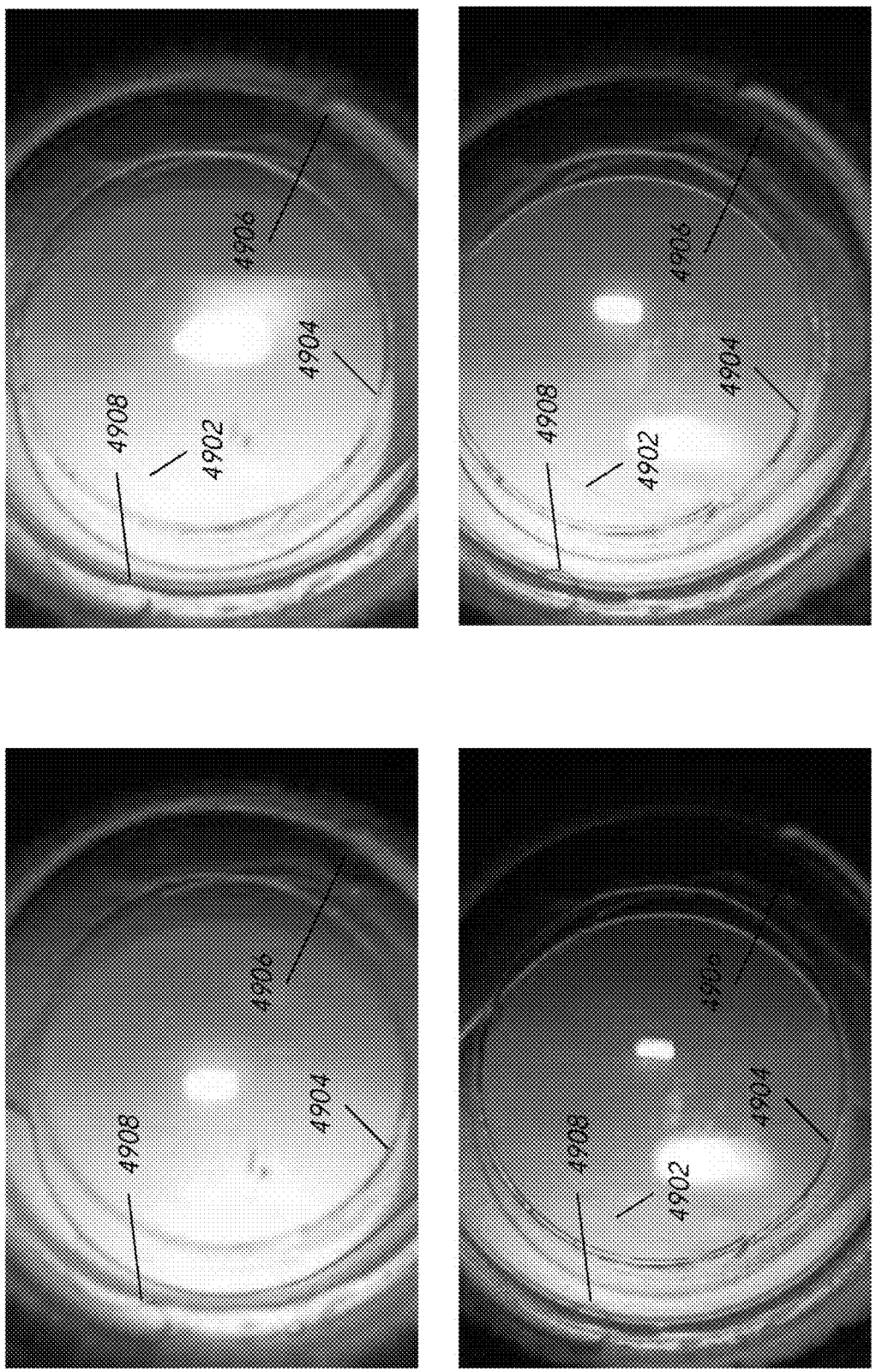
Figure 18E:
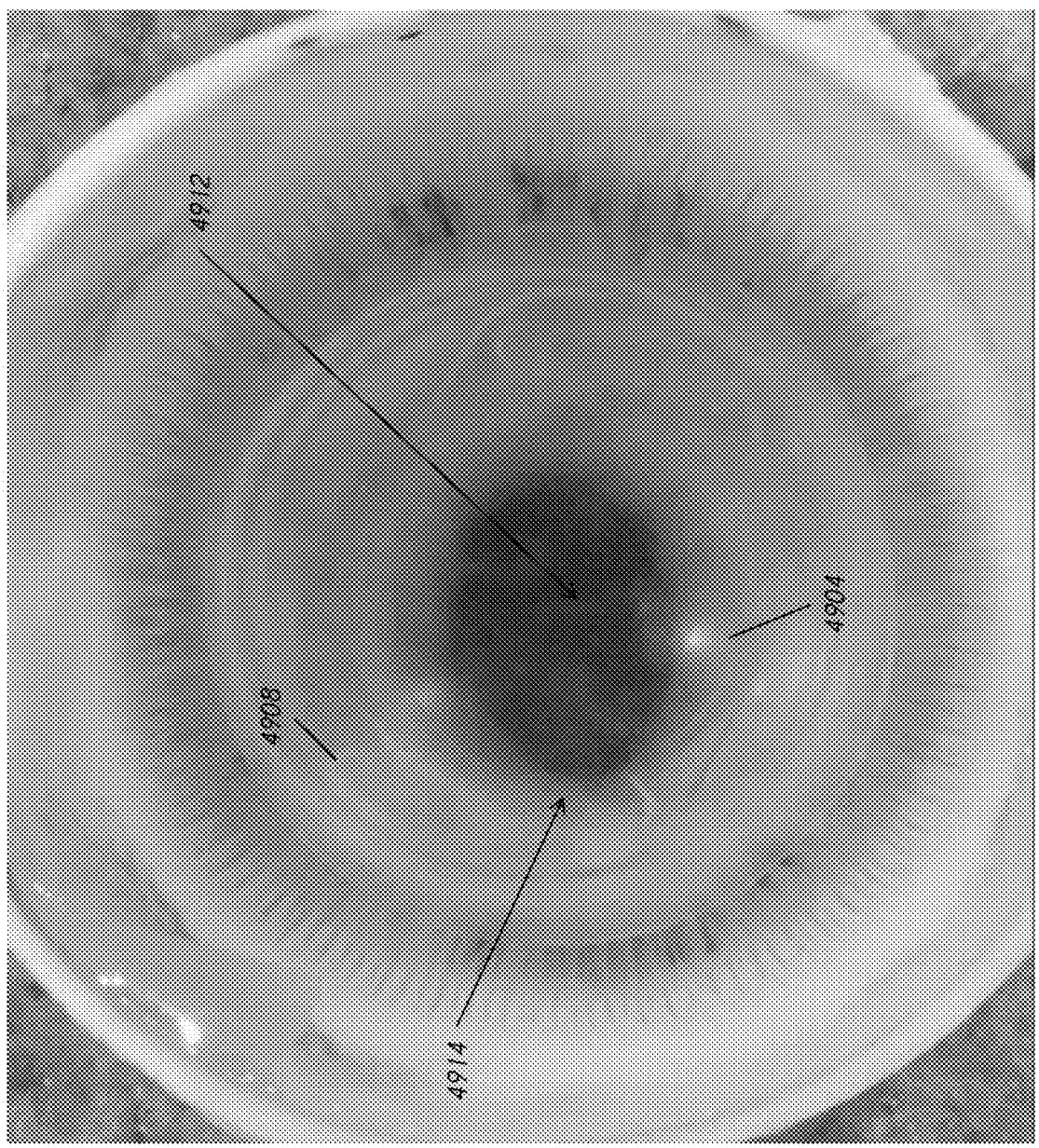

FIGS. 18A-18E are photographs of animal study results for a right eye of a third rabbit. FIG. 18A is after one week, FIG. 18B is after two weeks, FIG. 18C is after three weeks, and FIGS. 18D and 18E are after four weeks. FIGS. 18A-18E illustrate an anterior capsulorhexis 4902, a refractive surface 4904 of an IOL, an anterior opening 4906 of a prosthetic capsular device containing the IOL, and IOL haptics 4908. The IOL haptics 4908 are not visible in some figures, although the position of the haptics may be assumed based on other figures and/or the position of any visible portions of the IOL flared radially outwardly to form the start of the haptics. The natural capsular bag is substantially free of fibrosis. FIG. 18E shows material 4912 on a posterior surface of the IOL and the inception of peripheral PCO 4614.

Figure 19A:
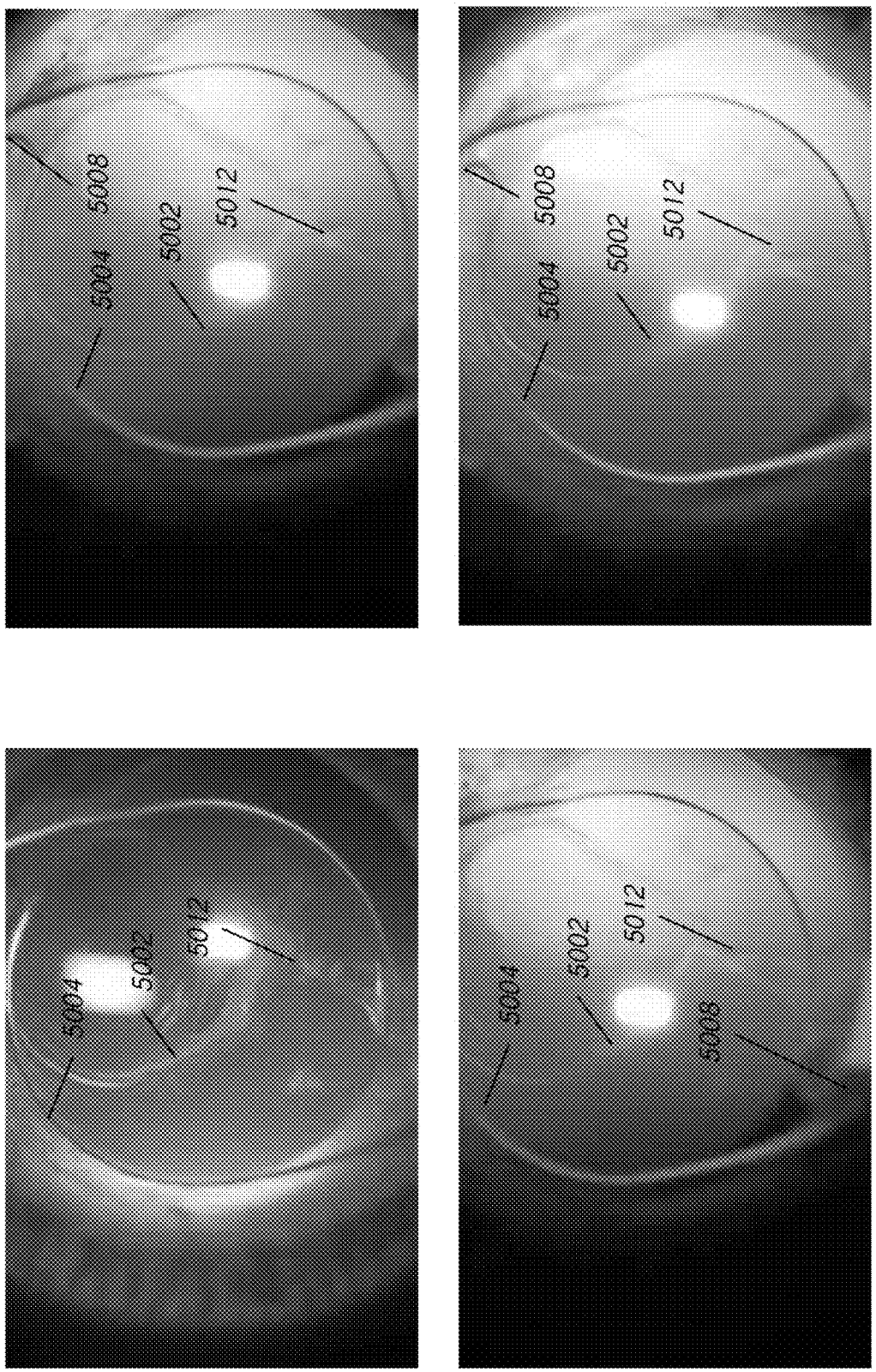
Figure 19B:
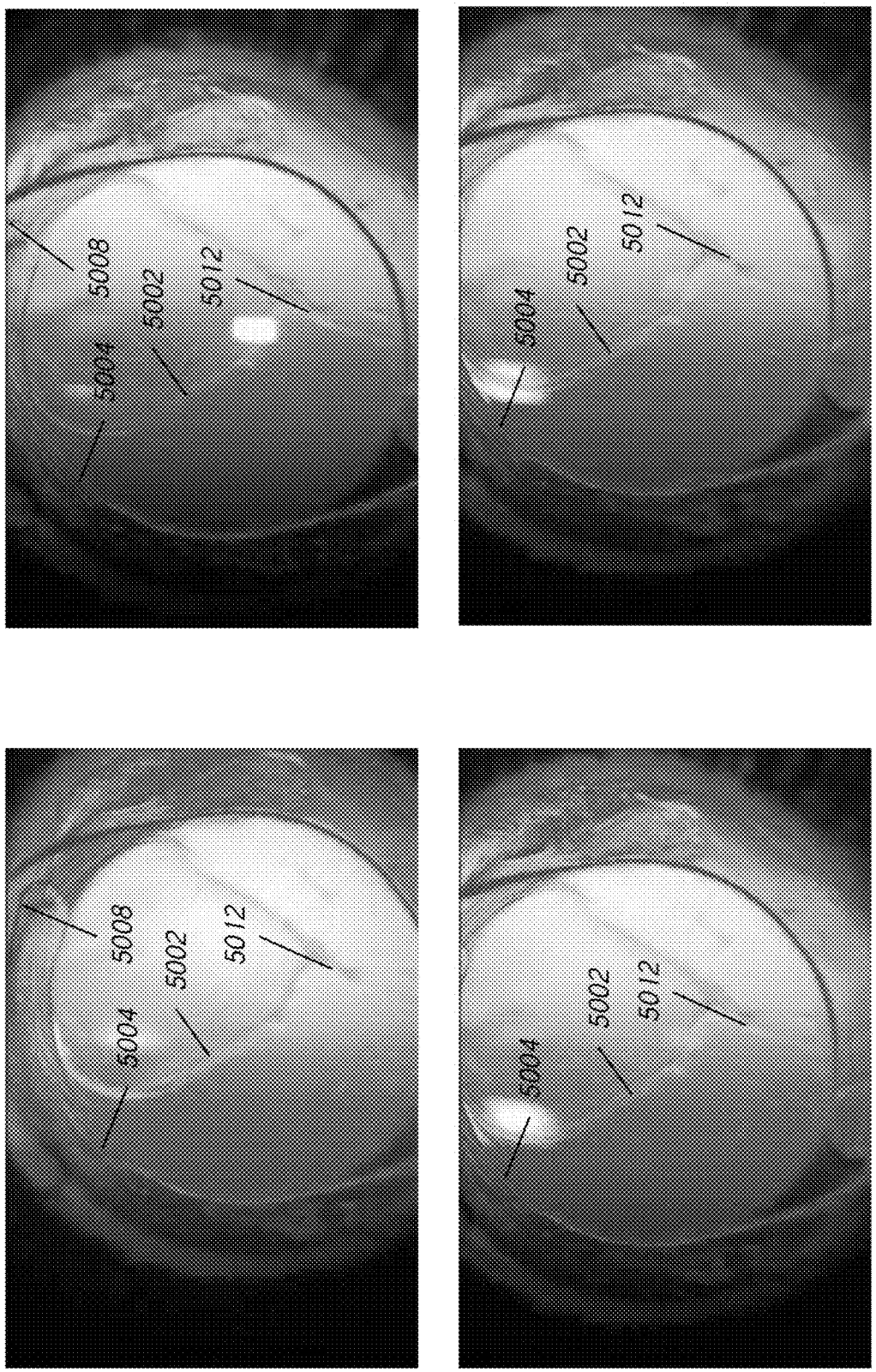
Figure 19E:
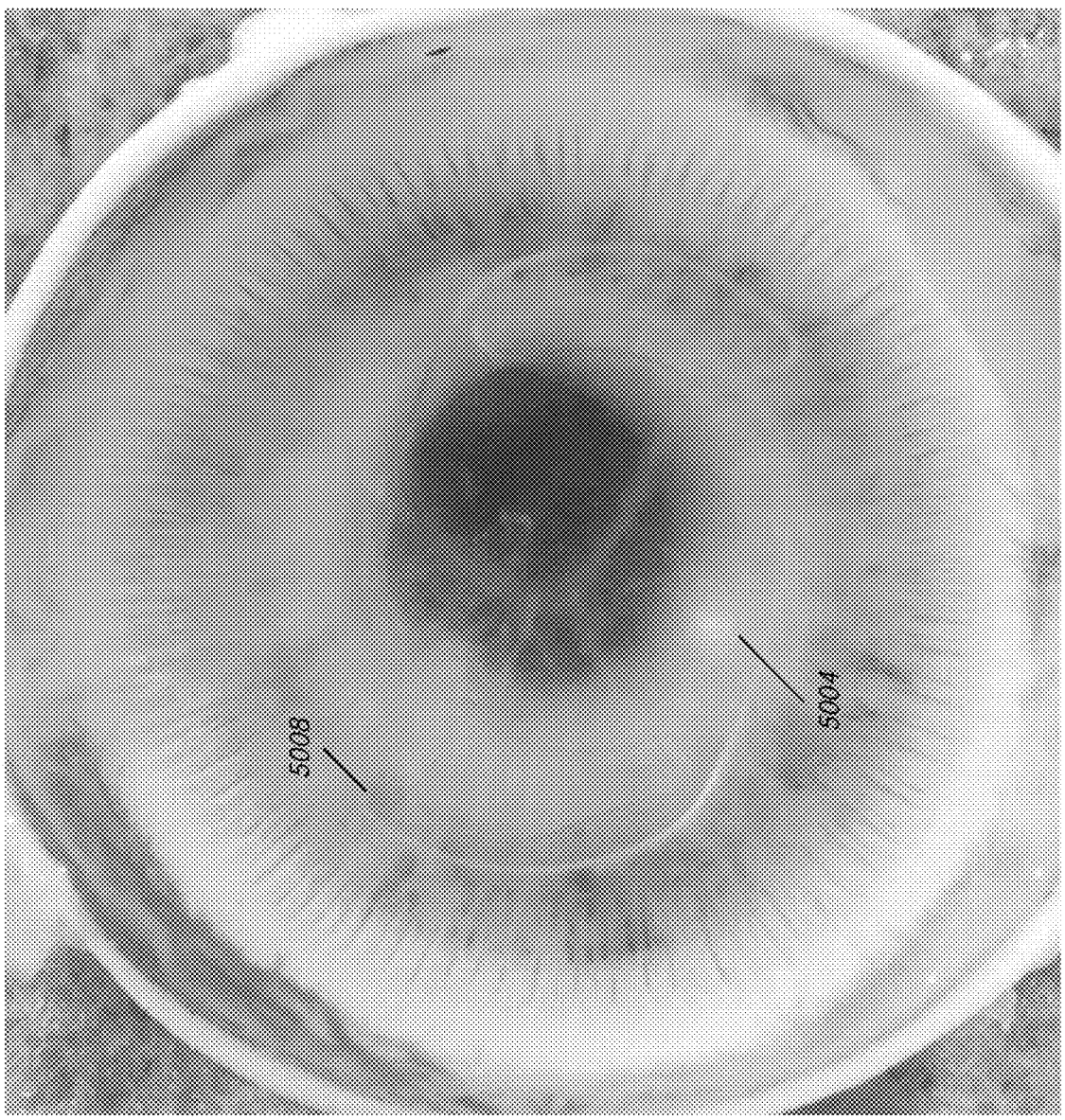

FIGS. 19A-19E are photographs of animal study results for a left eye of the third rabbit. FIG. 19A is after one week, FIG. 19B is after two weeks, FIG. 19C is after three weeks, and FIGS. 19D and 19E are after four weeks. FIGS. 19A-19E illustrate an anterior capsulorhexis 5002, a refractive surface 5004 of an IOL, and IOL haptics 5008. The IOL haptics 5008 are not visible in some figures, although the position of the haptics may be assumed based on other figures and/or the position of any visible portions of the IOL flared radially outwardly to form the start of the haptics. Out of all the left eyes, FIGS. 19A-19E show the most dramatic contraction of the natural capsular bag, which can be seen by the size of the anterior capsulorhexis 4902. Due to the contraction and fibrosis, the effective diameter at which the left eye of FIGS. 19A-19E can take in light is about 4.2 mm, which significantly impairs the vision in that eye except under the best lighting conditions. FIG. 19E also shows PCO.

Figure 20A:
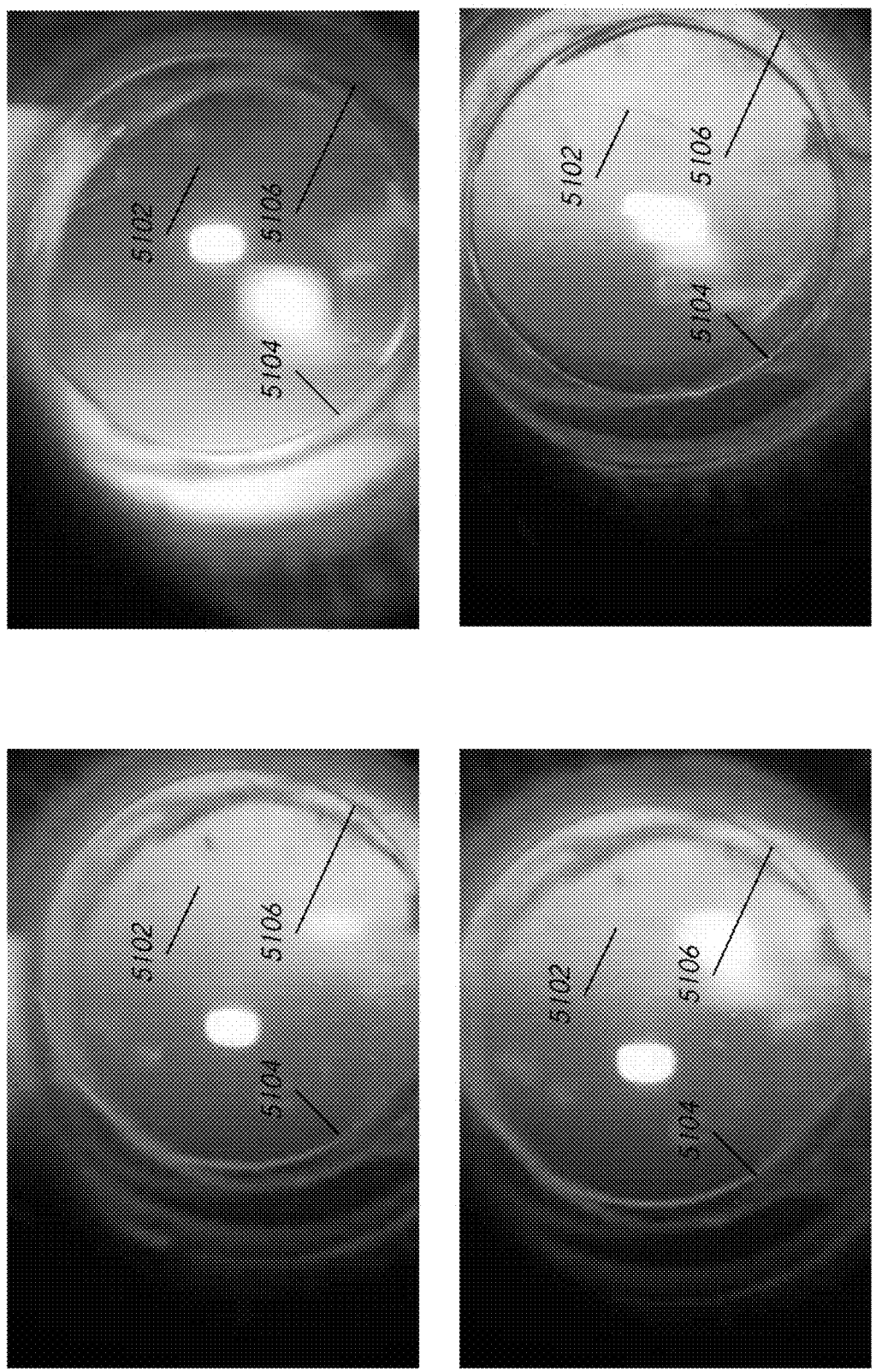
Figure 20B:
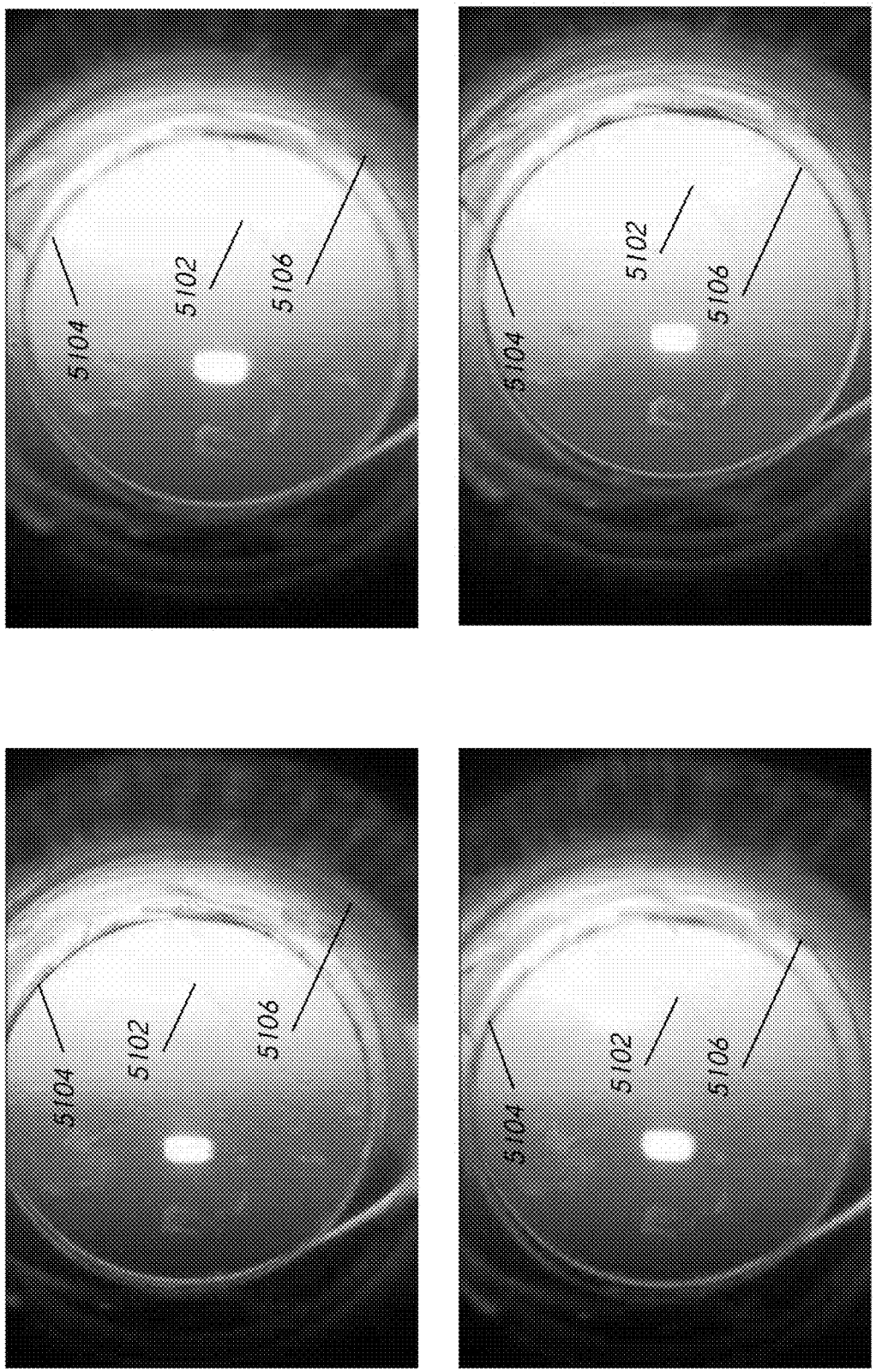
Figure 20D:
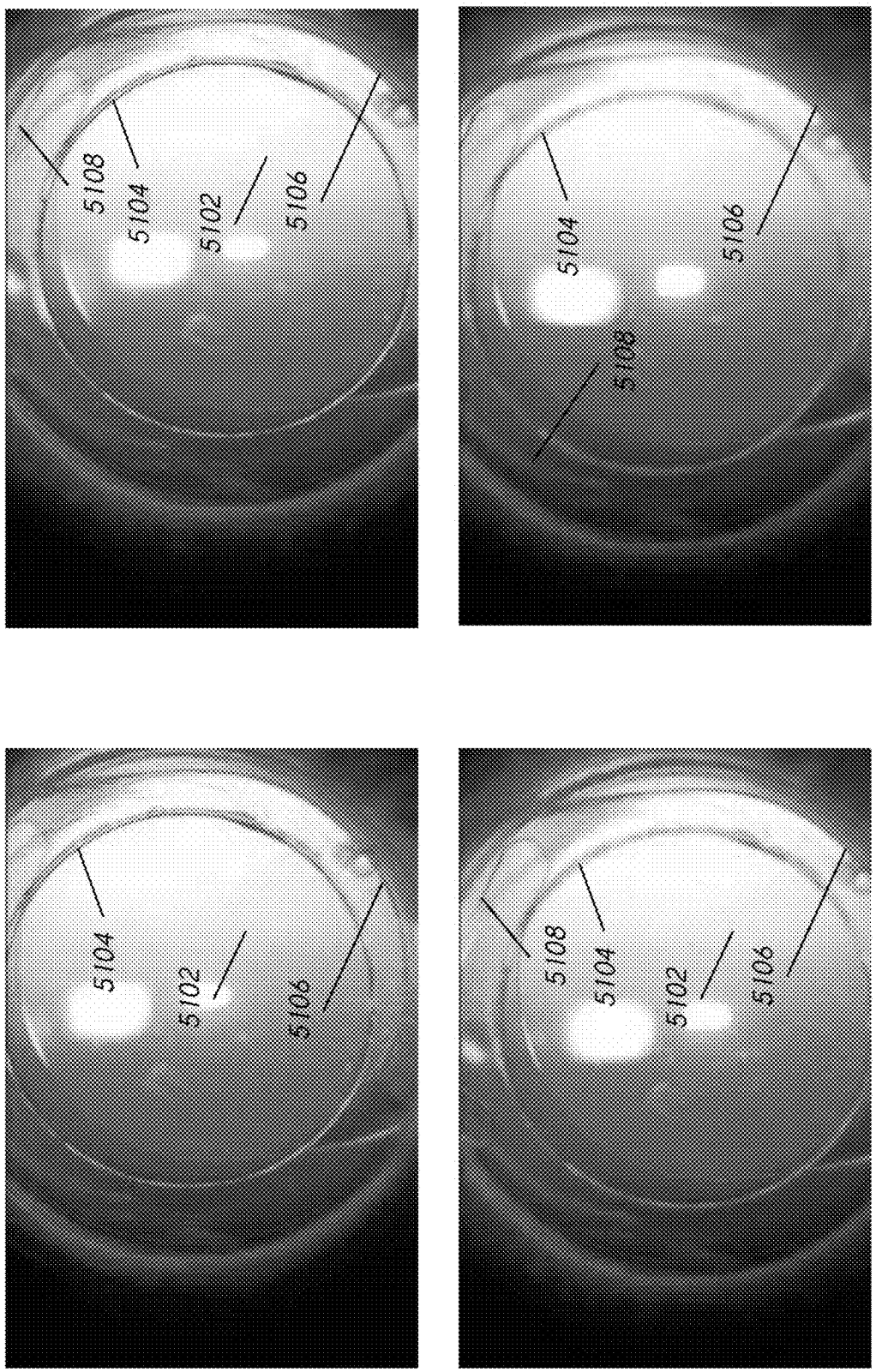
Figure 20E:
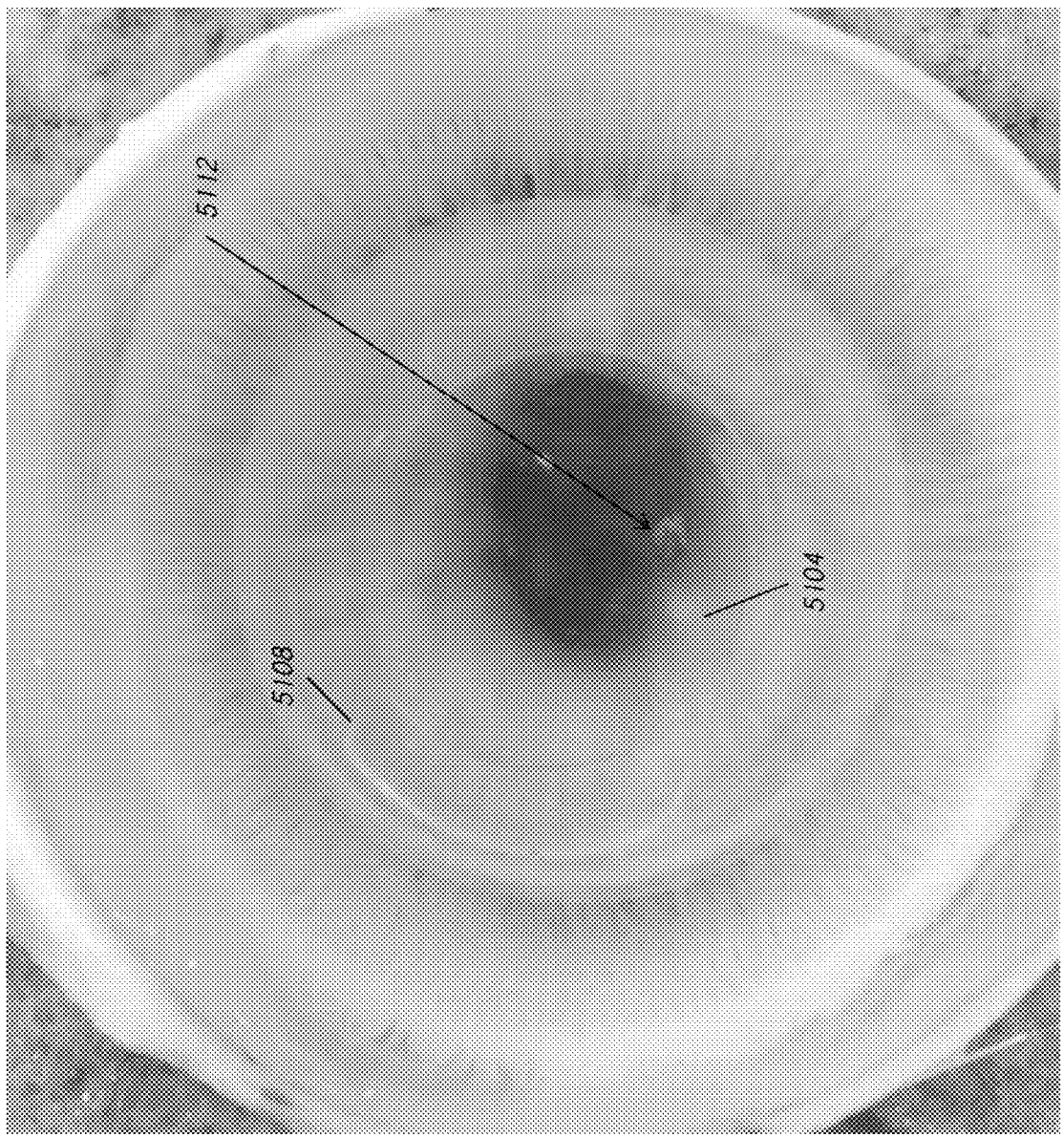

FIGS. 20A-20E are photographs of animal study results for a right eye of a fourth rabbit. FIG. 20A is after one week, FIG. 20B is after two weeks, FIG. 20C is after three weeks, and FIGS. 20D and 20E are after four weeks. FIGS. 20A-20E illustrate an anterior capsulorhexis 5102, a refractive surface 5104 of an IOL, an anterior opening 5106 of a prosthetic capsular device containing the IOL, and IOL haptics 5108. The IOL haptics 5108 are not visible in some figures, although the position of the haptics may be assumed based on other figures and/or the position of any visible portions of the IOL flared radially outwardly to form the start of the haptics. FIGS. 20A-20E show that the prosthetic capsular device may have been poorly centered in the natural capsular bag and/or that the natural capsular bag contracted, but the natural capsular bag is substantially free of fibrosis such that mis-centering and/or contraction does not present a serious issue, as light may pass through the still-epithelial natural capsular bag cells. FIG. 20E shows material 5112 on a posterior surface of the IOL. The right eye of the fourth rabbit also shows a small amount of fibrin peripherally between the prosthetic capsular device and the IOL, discussed in further detail below.

Figure 21A:
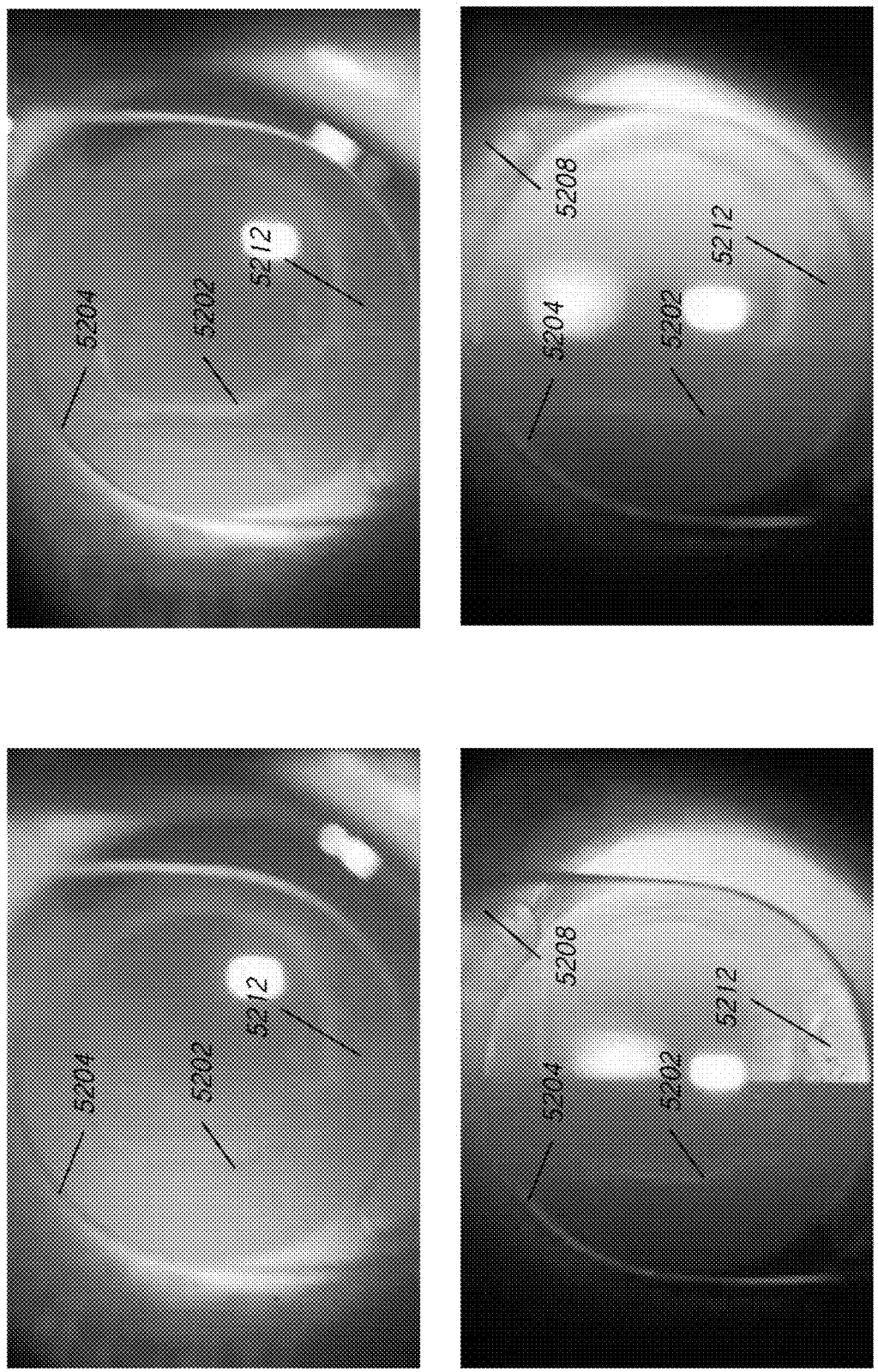
Figure 21B:
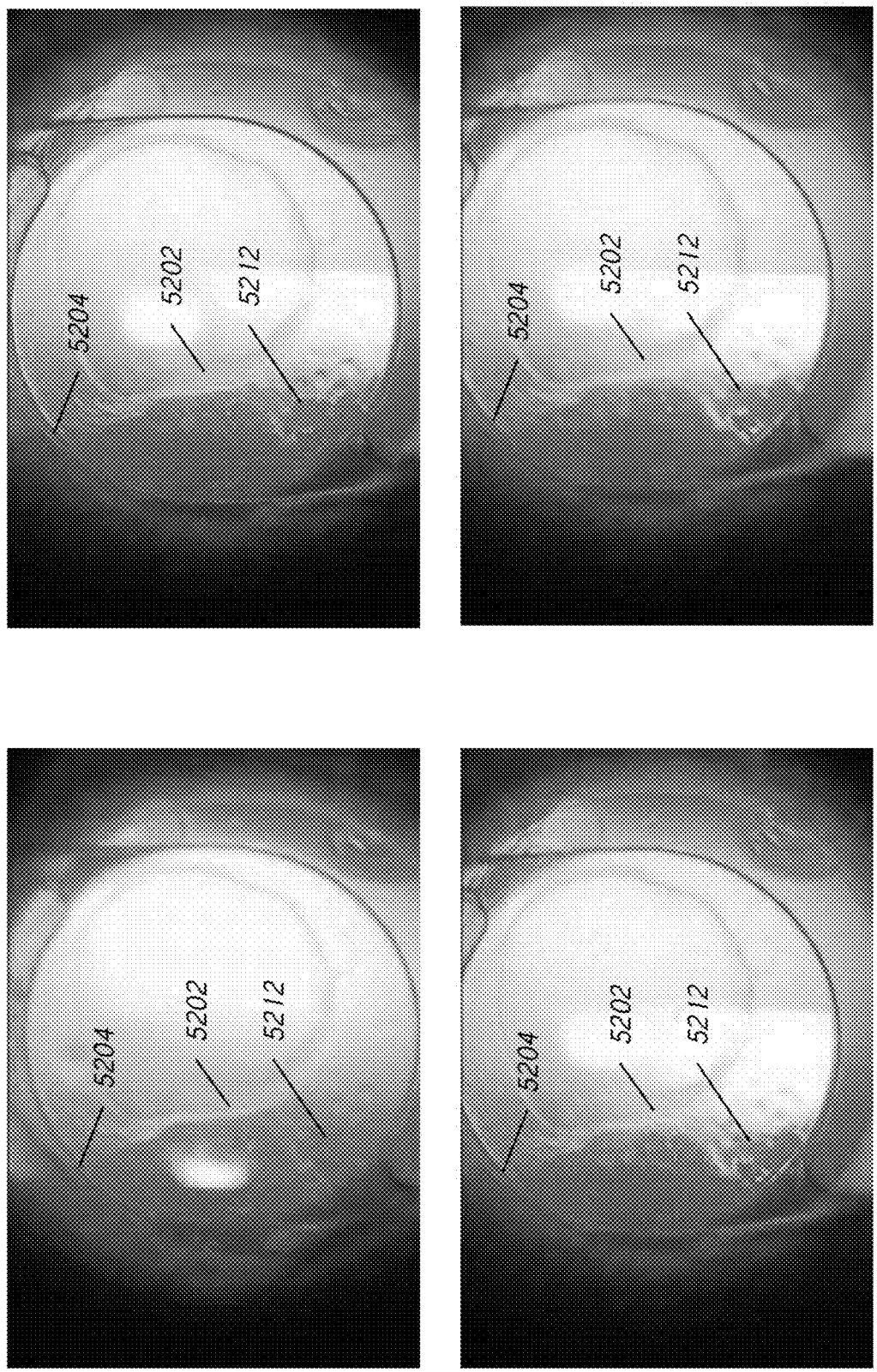
Figure 21C:
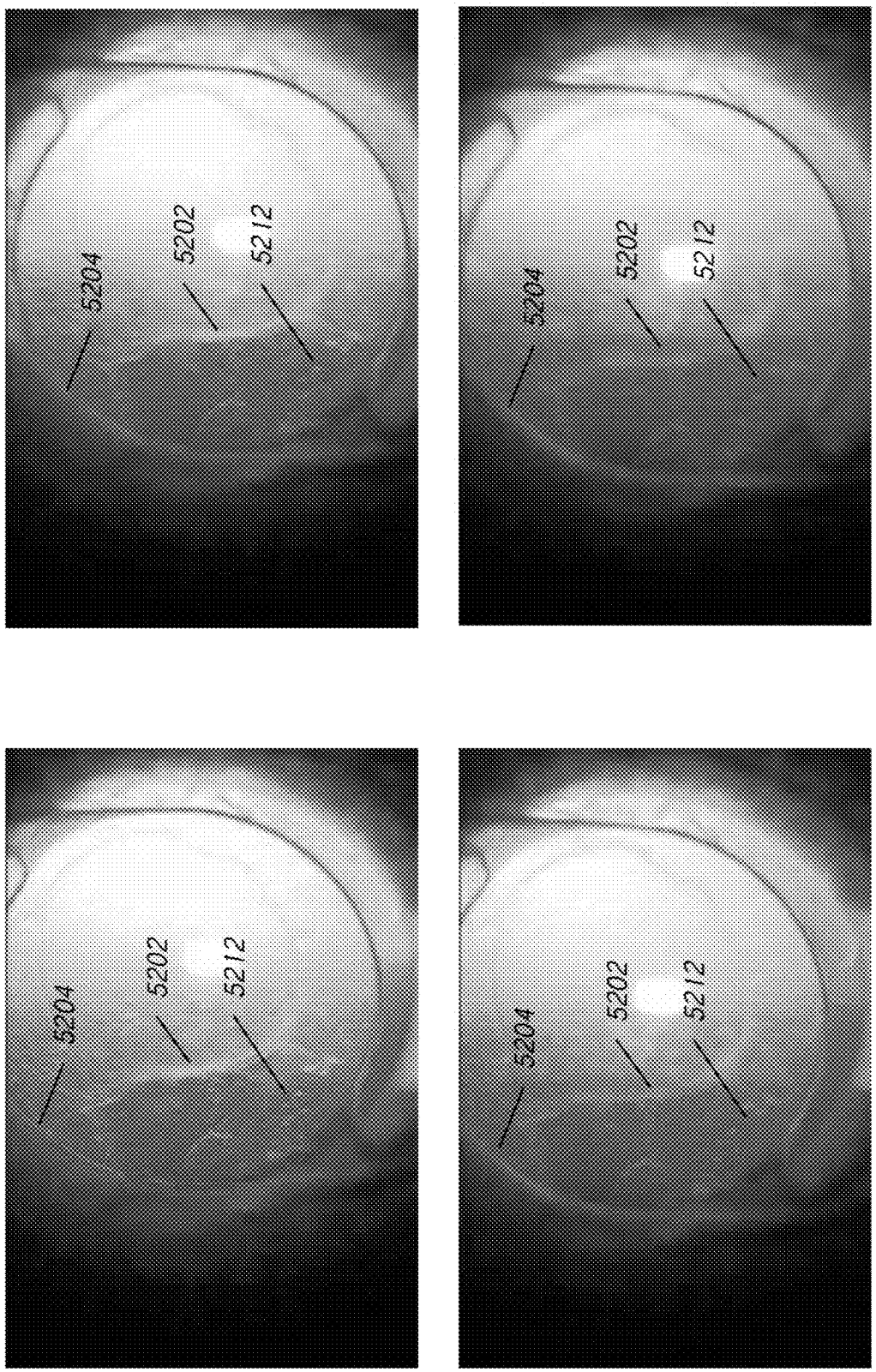
Figure 21E:
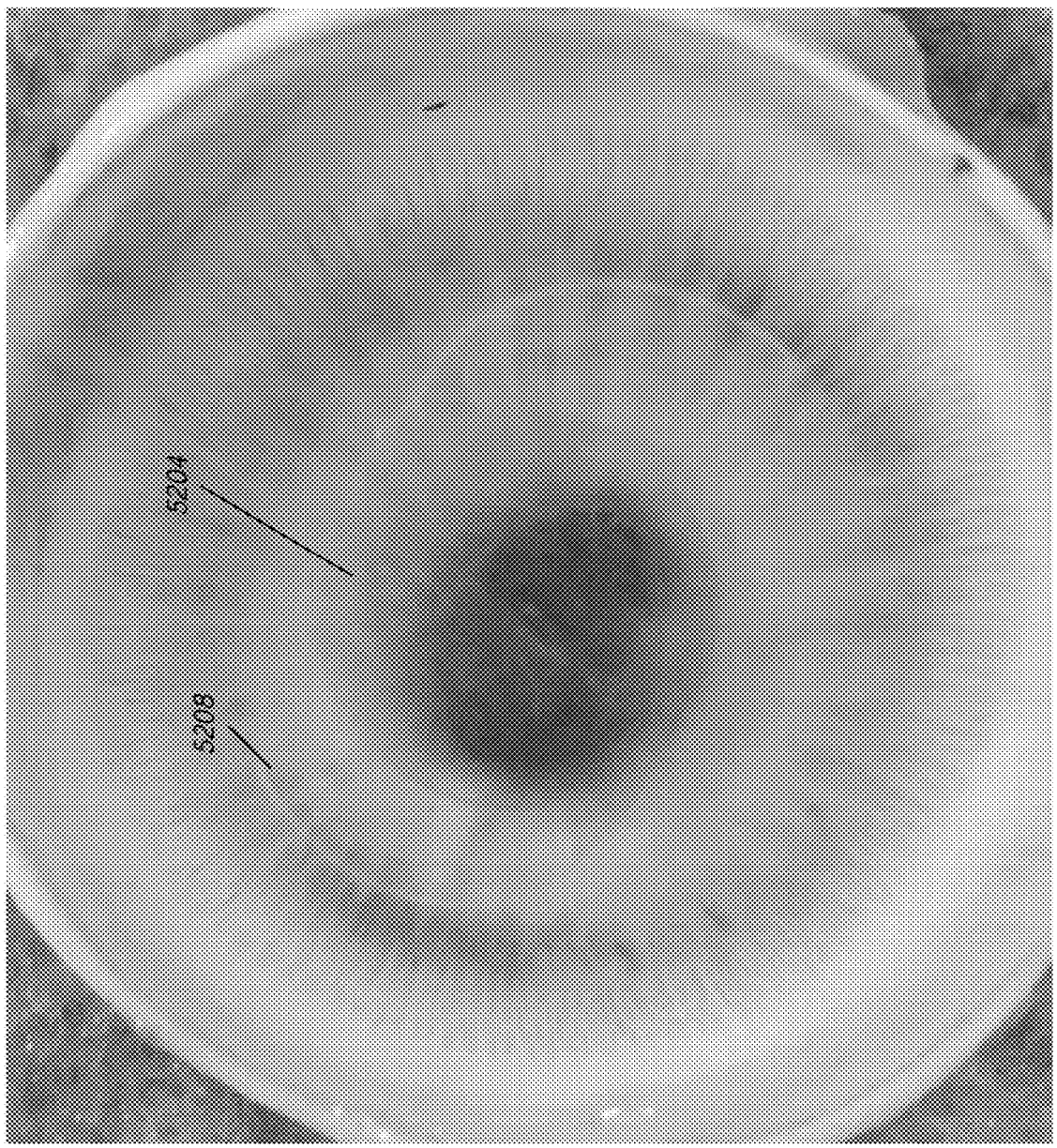

FIGS. 21A-21E are photographs of animal study results for a left eye of the fourth rabbit. FIG. 21A is after one week, FIG. 21B is after two weeks, FIG. 21C is after three weeks, and FIGS. 21D and 21E are after four weeks. FIGS. 21A-21E illustrate an anterior capsulorhexis 5202, a refractive surface 5204 of an IOL, and IOL haptics 5208. The IOL haptics 5208 are not visible in some figures, although the position of the haptics may be assumed based on other figures and/or the position of any visible portions of the IOL flared radially outwardly to form the start of the haptics. Like several of the other left eyes, FIGS. 21A-21E show significant fibrosis and contraction. Due to the contraction and fibrosis, the effective diameter at which the left eye of FIGS. 21A-21E can take in light is about 2.6 mm, which significantly impairs the vision in that eye except under the best lighting conditions. FIG. 21E also shows PCO.

Figure 22A:
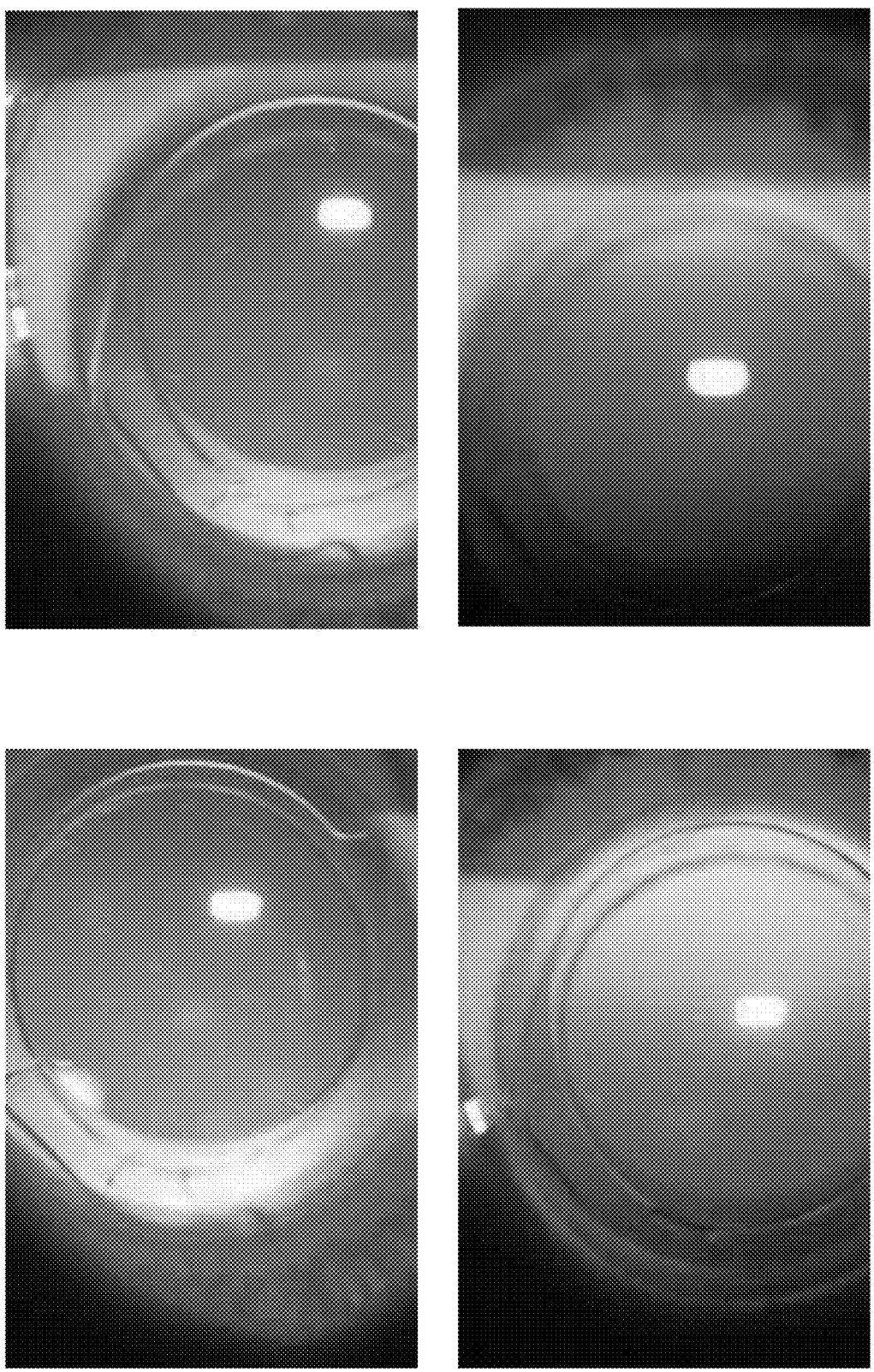
Figure 22B:
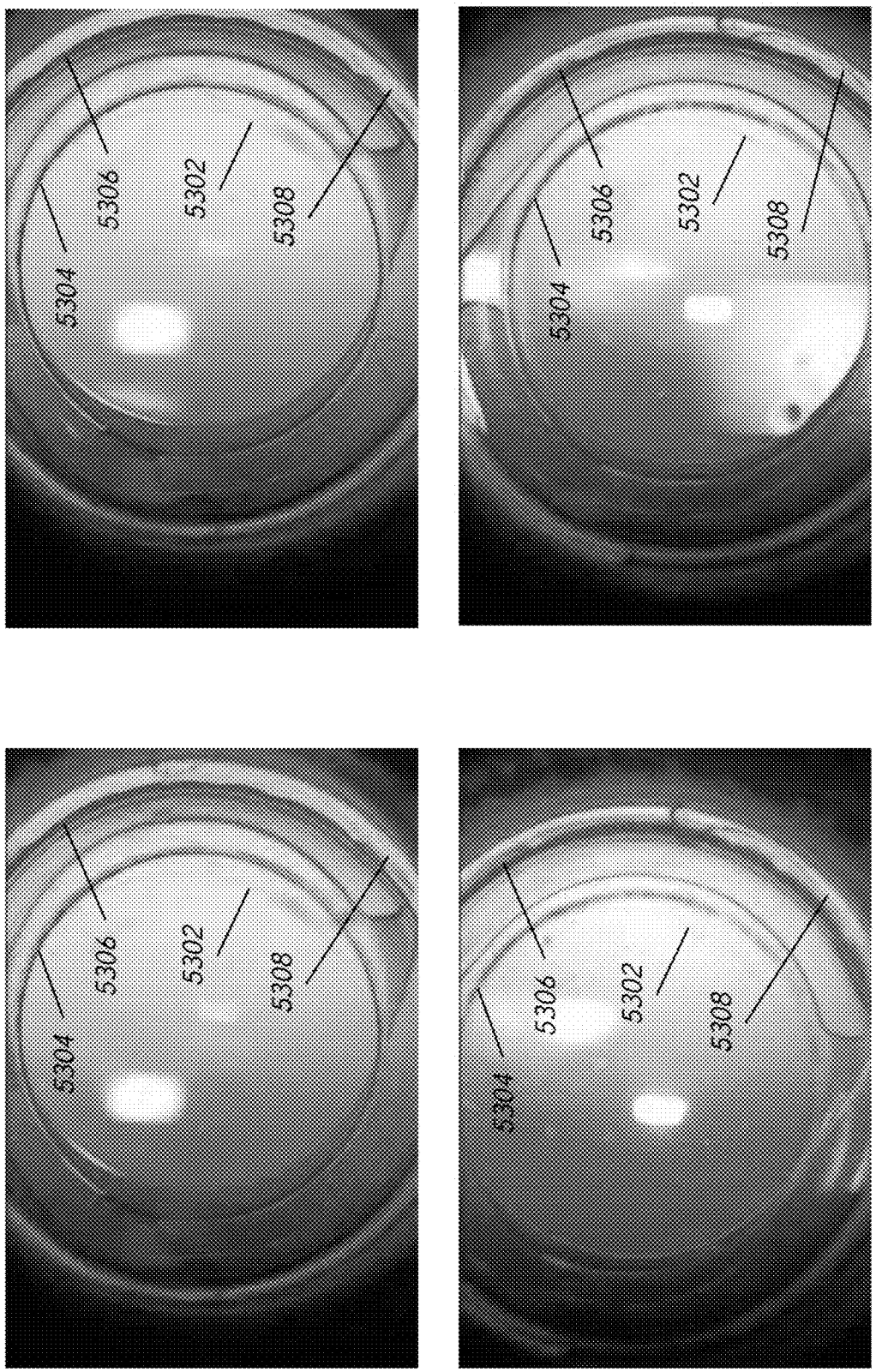
Figure 22C:
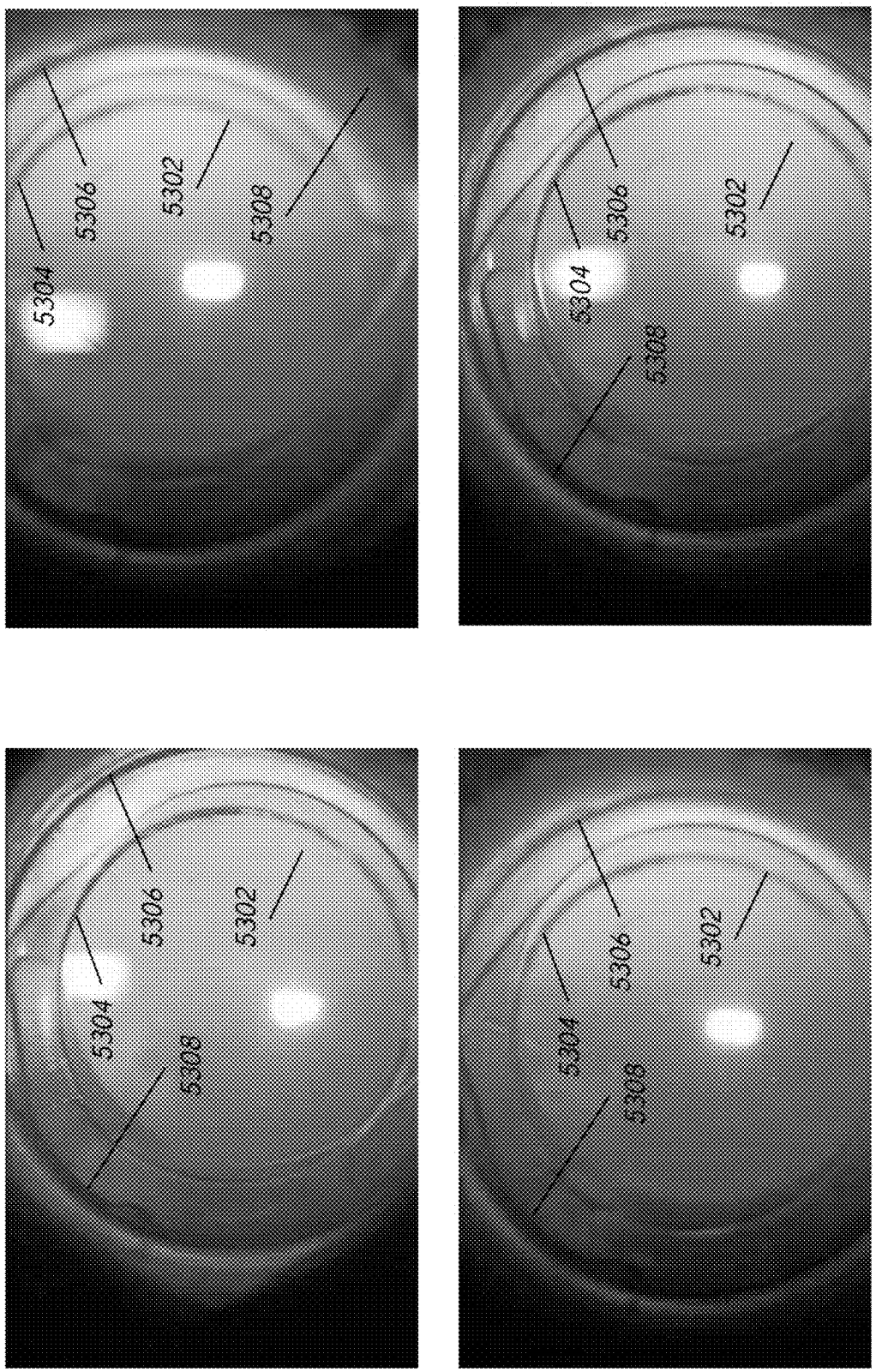
Figure 22D:
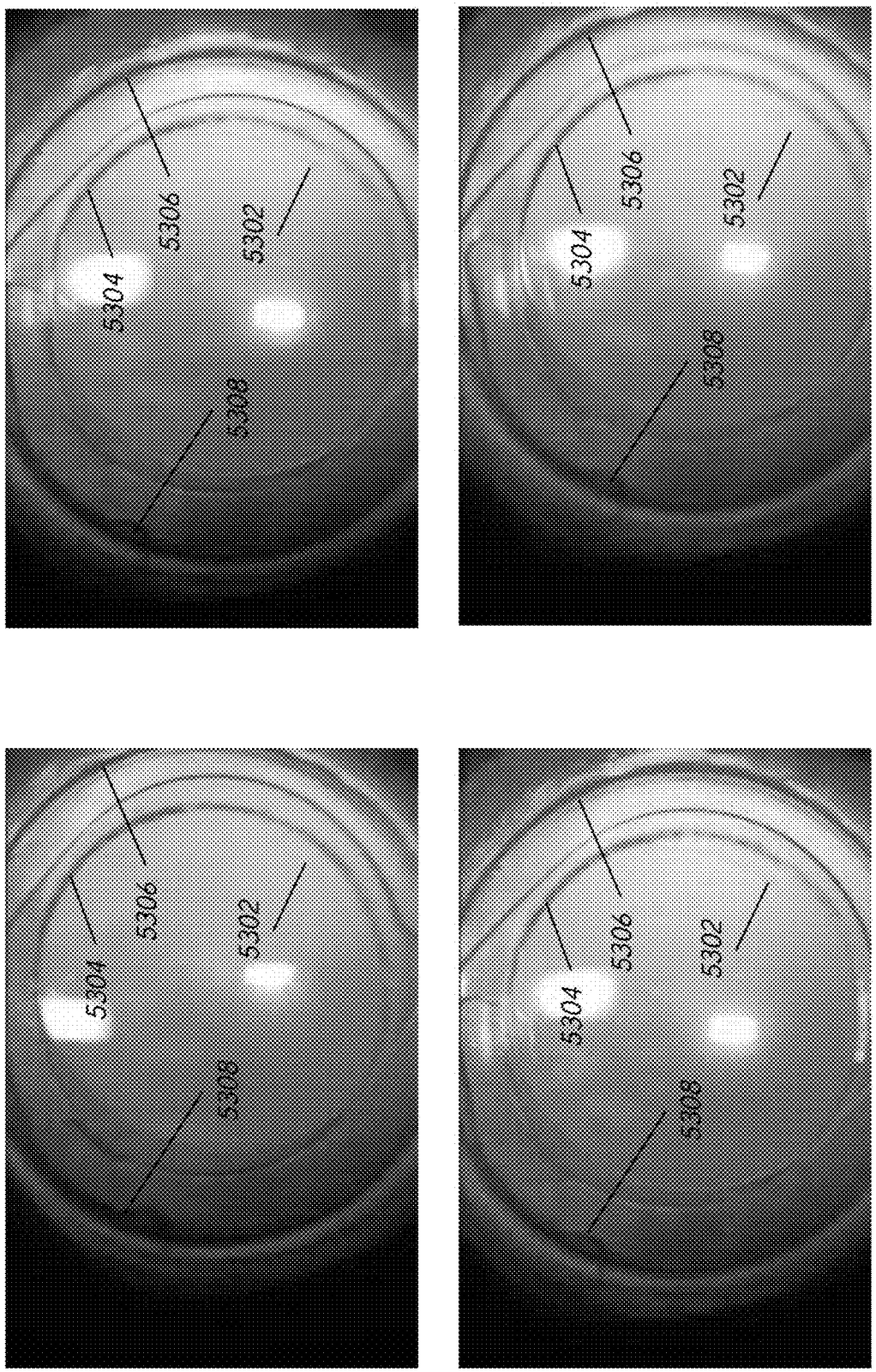

FIGS. 22A-22E are photographs of animal study results for a right eye of a fifth rabbit. FIG. 22A is after one week, FIG. 22B is after two weeks, FIG. 22C is after three weeks, and FIGS. 22D and 22E are after four weeks. FIGS. 22A-22E illustrate an anterior capsulorhexis 5302, a refractive surface 5304 of an IOL, an anterior opening 5306 of a prosthetic capsular device containing the IOL, and IOL haptics 5308. The IOL haptics 5308 are not visible in some figures, although the position of the haptics may be assumed based on other figures and/or the position of any visible portions of the IOL flared radially outwardly to form the start of the haptics. Like FIGS. 18A-18E, FIGS. 22A-22E show good centering of the prosthetic capsular device in the natural capsular bag, and lack of fibrosis. FIG. 22E shows material 5312 on a posterior surface of the IOL and peripheral PCO 5314.

Figure 23A:
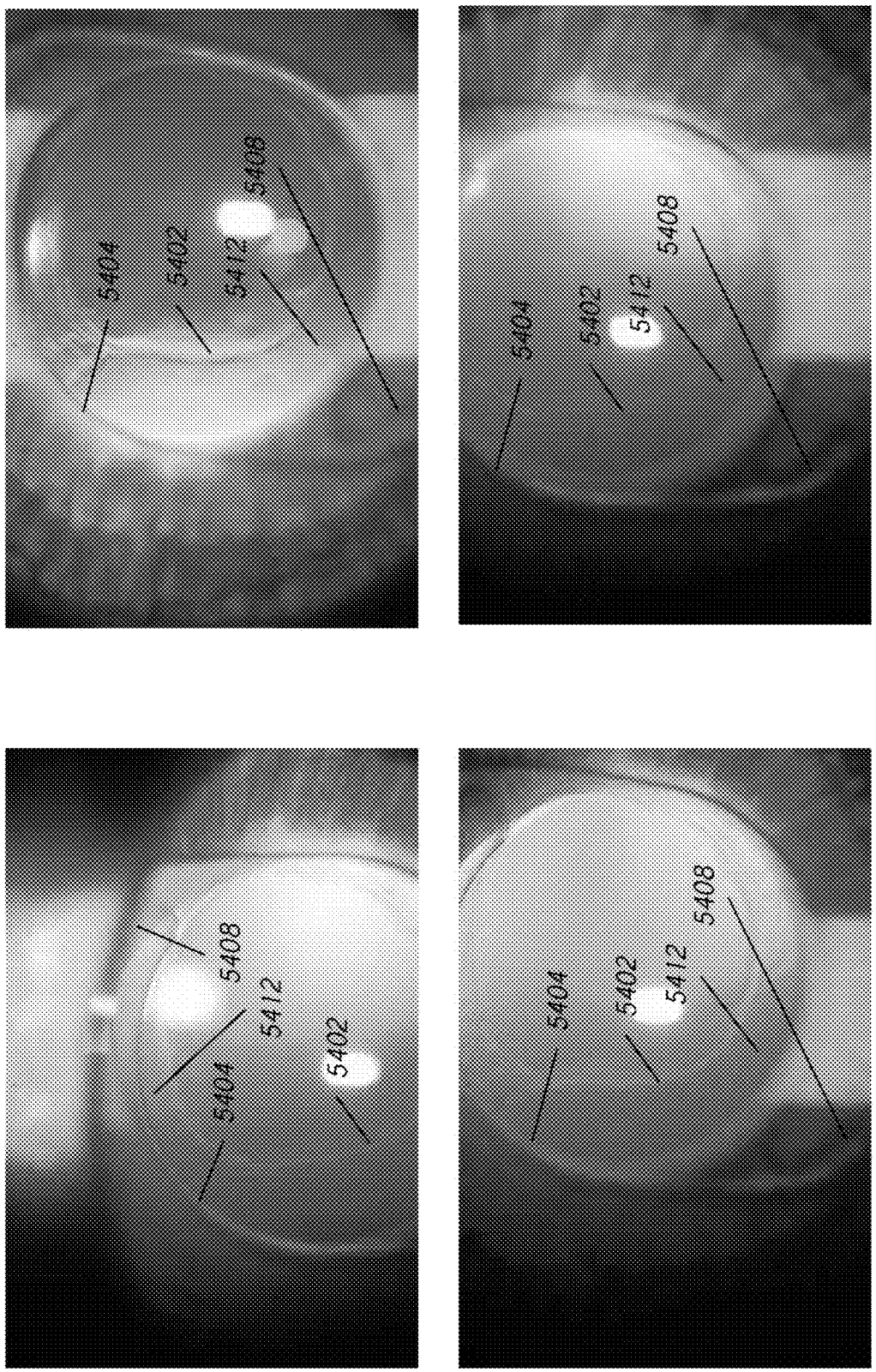
Figure 23B:
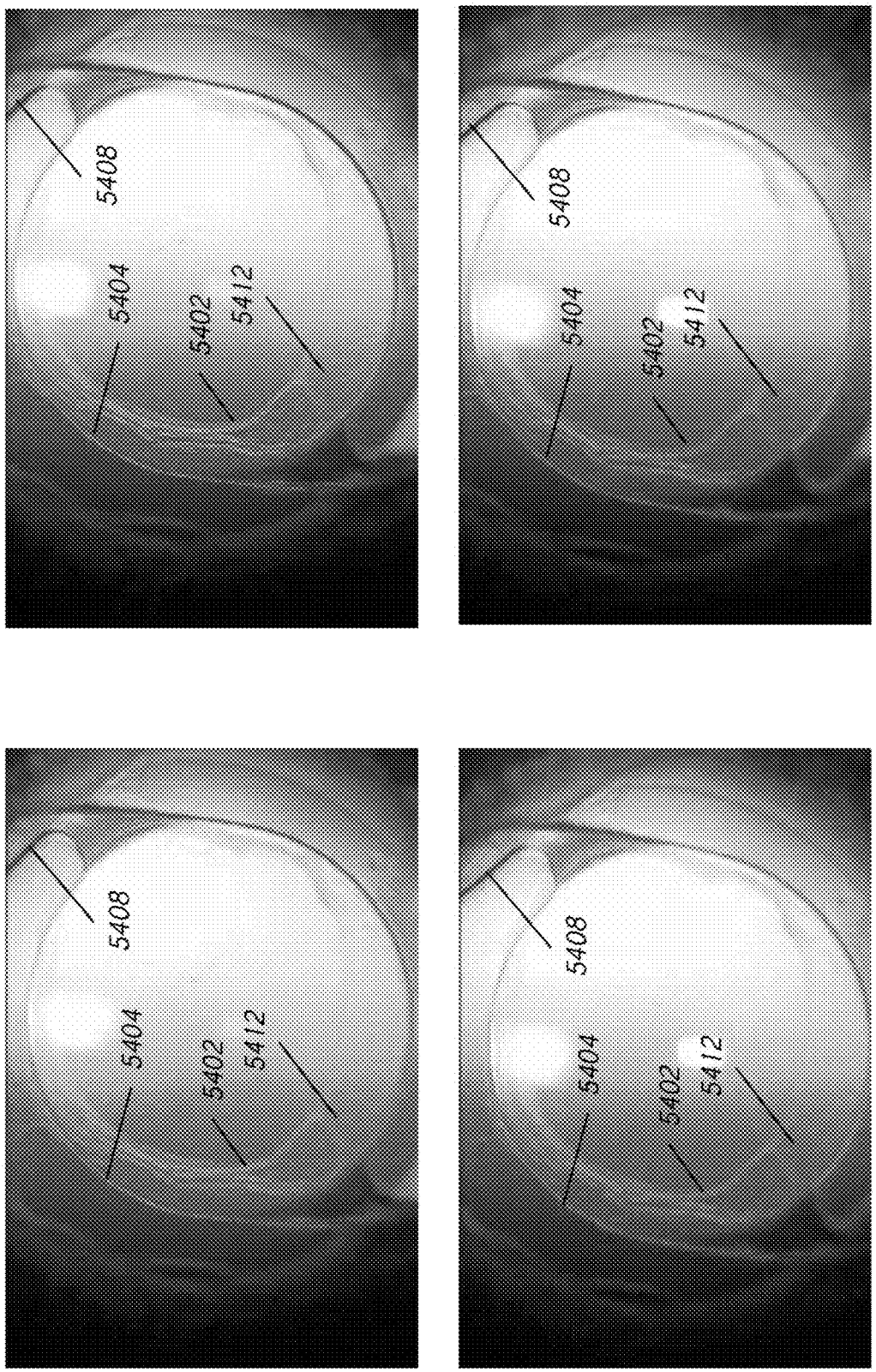
Figure 23C:
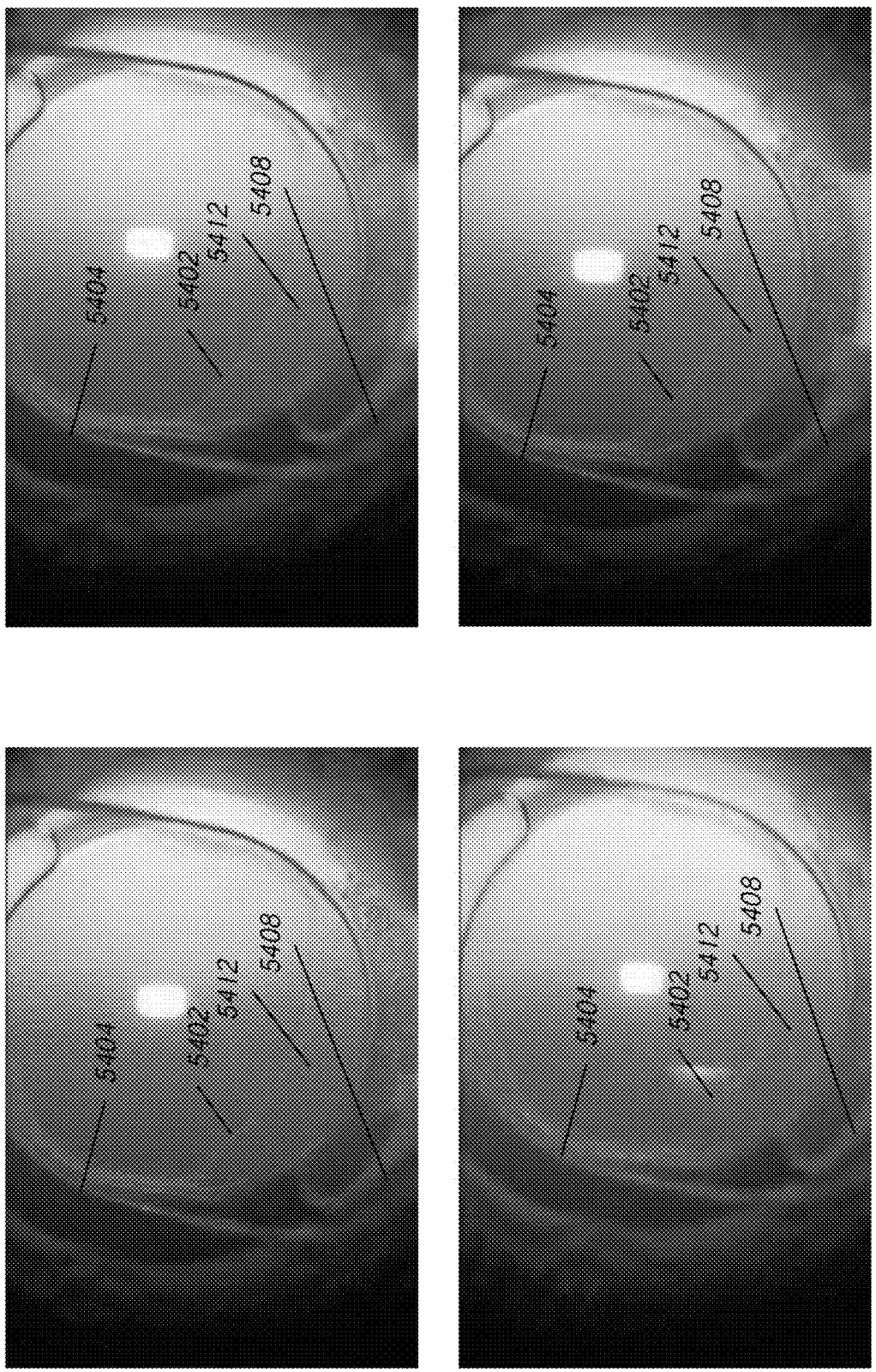
Figure 23E:
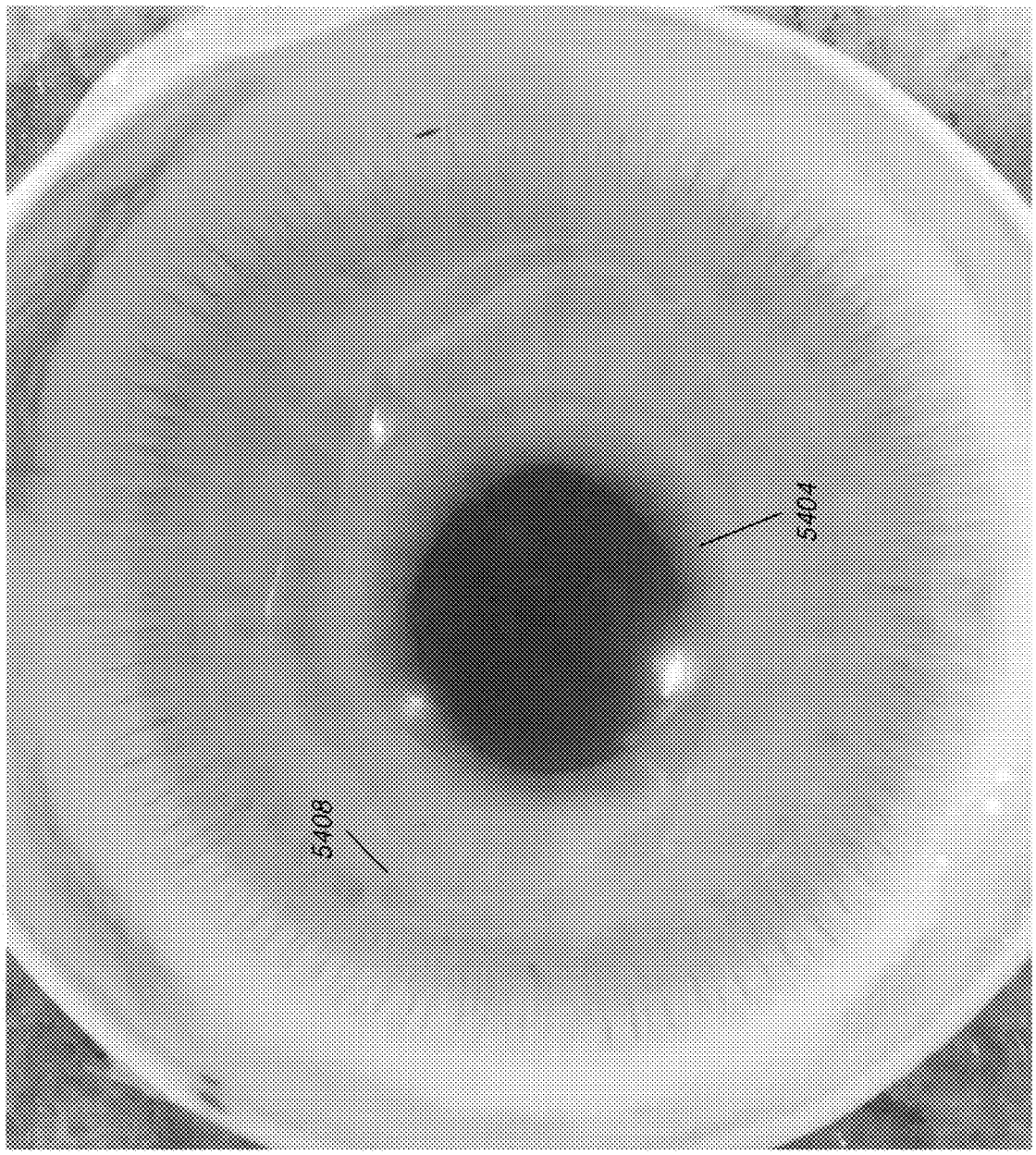

FIGS. 23A-23E are photographs of animal study results for a left eye of the fifth rabbit. FIG. 23A is after one week, FIG. 23B is after two weeks, FIG. 23C is after three weeks, and FIGS. 23D and 23E are after four weeks. FIGS. 23A-23E illustrate an anterior capsulorhexis 5402, a refractive surface 5404 of an IOL, and IOL haptics 5408. The IOL haptics 5408 are not visible in some figures, although the position of the haptics may be assumed based on other figures and/or the position of any visible portions of the IOL flared radially outwardly to form the start of the haptics. Like several of the other left eyes, FIGS. 21A-21E show significant fibrosis and contraction. Due to the contraction and fibrosis, the effective diameter at which the left eye of FIGS. 23A-23E can take in light is about 4.5 mm, which significantly impairs the vision in that eye except under the best lighting condition.

The reduction in the effective diameter shows why PCO can be so detrimental and preferably reduced or prevented. As described above, a Nd:YAG laser may be used to ablate the natural capsular bag to remove the opaque membrane. If the natural capsular bag separating the vitreous is removed, then post-PCO treatment operation on an IOL absent a prosthetic capsular device could result in anterior flow of vitreous. A careful user may be able to viscodissect an IOL from an eye and place a prosthetic capsular device comprising a posterior surface into the eye to inhibit or prevent the flow of vitreous. The eye of a post-PCO subject with an existing IOL issue may be salvageable using a prosthetic capsular device, providing another potential advantage and/or use.

One goal of the animal studies of FIGS. 14A-23E was to show that use of a prosthetic capsular device was not worse for the eye than use of an IOL alone. The right eyes were all substantially free of fibrosis (e.g., almost totally pristine), IOL position shift, and anterior capsulorhexis contraction. By contrast, the left eyes generally showed significant fibrosis, IOL migration, and significant asymmetric contraction of the capsulorhexis. The animal studies empirically show that the use of a prosthetic capsular device can provide at least some of the advantages discussed herein.

Slight damage to the prosthetic capsular devices such as small tears in the edge of the anterior opening may have occurred due to insertion through the Accuject 2.2 mm injectors. Upon any incomplete injection of the prosthetic capsular device into the natural capsular bag, the prosthetic capsular device was manipulated with a collar button hook after injection to complete in-the-bag fixation. The manipulation and/or a hard push on the injector may have caused the damage. Injection of the prosthetic capsular device fully into the natural capsular bag (e.g., without further manipulation or repositioning), for example using a different injector, may reduce the risk of tearing the prosthetic capsular device.

Inflammation of the vitreous in right eyes, starting after about two weeks and then decreasing throughout the follow up, may have been due to the material of the prosthetic capsular device being sterilized, but not having undergone an extensive extraction process such that uncrosslinked siloxane monomers can leach out of the material over time. Extraction prior to sterilization and packaging of the prosthetic capsular device, for example single, double, triple, or more extractions to promote crosslinking (e.g., substantially total crosslinking), may reduce such inflammation.

Fibrin formation between the prosthetic capsular device and the IOL may have been due to incomplete viscoelastic removal and/or residual OVD remained trapped behind the IOL. More aggressive viscoelastic evacuation after the implantation, use of a more cohesive viscoelastic material, which may be easier to remove than dispersive viscoelastic materials, and/or an OVD removal technique may reduce the such fibrin formation. There was little change in the fibrin material throughout the four weeks. Fibrin was also generally observed at the level of the capsulorhexis edge in the left eyes, which was resolved within two weeks.

Dilation or significant dilation of the natural capsular bag was generally associated with the presence of the prosthetic capsular device. However, ACO was absent, for example due to lack of contact between the residual anterior capsule and the anterior surface of the prosthetic capsular device, such that the dilation was not a negative result.

The right eyes, in which a prosthetic capsular device was placed before an IOL, showed significantly reduced Soemmering's ring formation compared to the left eyes, in which only an IOL was placed. The right eyes showed reduced central and peripheral PCO compared to the left eyes. A different edge profile (e.g., square) of a prosthetic capsular device, for example as described herein, may provide a better effect against PCO. PCO at week 4 of the examination was scored as a 0 in the right eyes and as 2±1 in the left eyes (two-tail P=0.01; t-Test: Paired Two Sample for Means). ACO was found to be absent in the right eyes and was mile (0.5 or 1) in the left eyes.

Central PCO was scored (two-tail P=0.05; t-Test: Paired Two Sample for Means) as 0.1±0.22 for right eyes and 1.2±0.75 for left eyes. Peripheral PCO was scored (two-tail P=0.23; t-Test: Paired Two Sample for Means) as 0.8±0.83 for right eyes and 1.8±0.83 for left eyes; the amount of PCO varied from a trace to moderate PCO. Soemmering's ring formation was scored (two-tail P=0.006; t-Test: Paired Two Sample for Means) as 2.8±0.83 for right eyes and 8.6±2.19 for left eyes; the left eyes all showed a moderate Soemmering's ring formation with proliferation of cortical material in the periphery. In all cases, a lower number indicates better results. In all parameters, eyes with a prosthetic capsular device scored better than eyes without a prosthetic capsular device.

All prosthetic capsular devices were found to be fully fixated inside of the natural capsular bag and centered. The IOL in FIGS. 14A-14E was very slightly decentered inside of the prosthetic capsular device. Mild IOL decentration (0.5 or 1) inside of the prosthetic capsular bag was observed in two left eyes.

There was no sign of untoward inflammation or toxicity on any of the left eyes. There was no sign of any toxicity or inflammation on four of the five right eyes. As mentioned above with respect to FIG. 16E, one right eye showed a mild anterior vitritis.

Figure 24B:
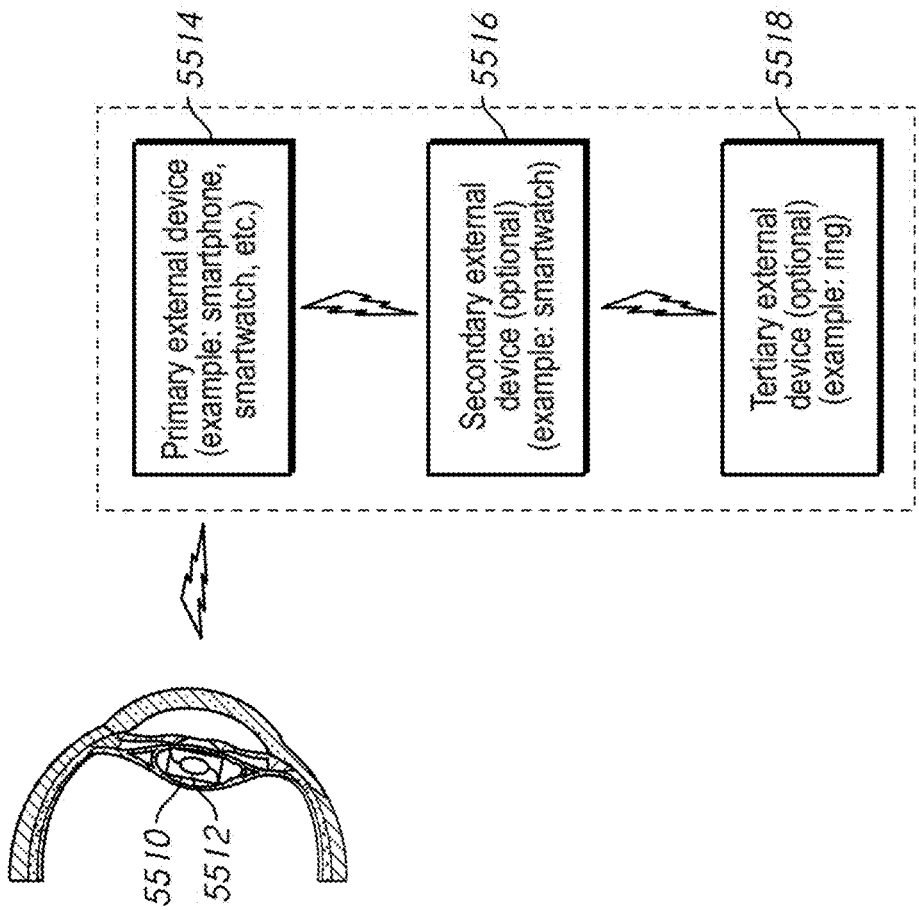
FIG. 24B is a schematic of a system for controlling an electronic device using an external device.
Figure 24A:
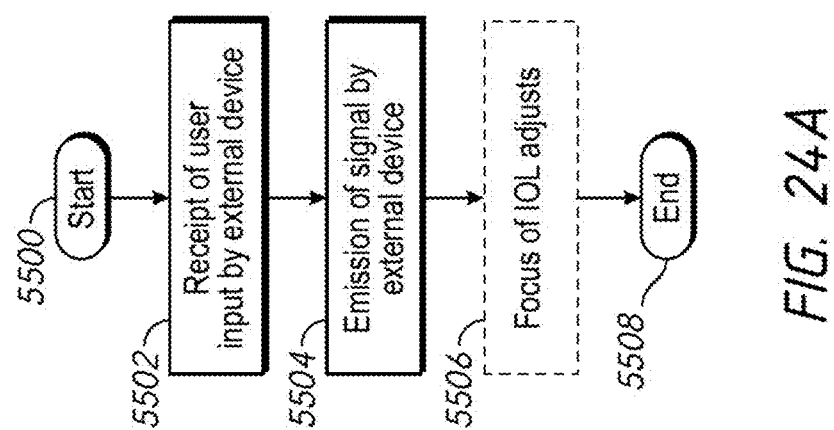
FIG. 24A is a flowchart of an example of controlling focus of an IOL using an external device.

Referring again to the disclosure regarding use of the technology device to control the properties of an IOL, FIG. 24A is a flowchart of an example of controlling focus of an IOL using an external device. Starting at block 5500, the external device receives input from a user at block 5502. An example of user input is control of an external device (e.g., external to the eye) such as a smartwatch, smartphone, and the like. In some implementations, control of the external device is with a second external device. For example, a user wearing a ring on one hand may touch a smartwatch worn on the opposite wrist to complete a circuit, send a signal (e.g., via near-field communication (NFC)), or otherwise communicate. In some implementations, the user operation 5502 does not require full attention of the user (e.g., attention to a display) such that the focus can be controlled without the user deviating from another activity such as driving or communicating with someone. For example, a user may initiate an operation by a series of taps on a smartwatch or a voice command based on built-in voice recognition such as Siri on Apple devices or OK Google on Android devices. In some implementations, features of a smartphone (e.g., volume buttons) and/or a smartwatch (e.g., a rotatable knob) can be manipulated, which may provide fine tuning of and/or adjusting of the focus. Operation of a software application running on an external device that is configured to control the IOL is also possible.

Upon receipt of the user input at block 5502, the external device wirelessly transmits an electronic message at block 5504 to the IOL. The wireless transmission may be in accordance with a standard wireless protocol such as Bluetooth or a specialized wireless protocol, for example to enhance security and/or safety. As described above, the external device may be a single device or a series of devices operating in conjunction with each other. For example, the external device that emits the wireless transmission at block 5504 may be a smartwatch. For another example, the external device that emits the wireless transmission at block 5504 may be a smartphone that received a first wireless transmission from a smartwatch. The wireless transmission is configured to be received by a technology device and/or an IOL configured to process the wireless transmission and cause focus adjustment.

In some implementations, the wireless transmission is received by the technology device of the prosthetic capsular device, which then controls operation of an adjustable-focus IOL in the prosthetic capsular device. In some implementations, the wireless transmission is received by the adjustable-focus IOL in the prosthetic capsular device directly (e.g., if the prosthetic capsular device lacks a suitable technology device or any technology device, or in the absence of the use of a prosthetic capsular device for suitable IOLs). In some implementations, the wireless transmission is received by another device that communicates with the technology device of the prosthetic capsular device and/or the adjustable-focus IOL in the prosthetic capsular device. For example, the smartwatch may send a wireless transmission to a smartphone, which emits a secondary wireless transmission that may be received by the IOL, the technology device, etc. One or more of the wireless transmissions may be sent over a network. Intraocular communication may be wireless (e.g., based on the same or different wireless standard) or wired (e.g., based on electrical contact between an exterior of the IOL haptics and an interior of the prosthetic capsular device).

In response to the wireless transmission or a secondary wireless transmission, the IOL focus adjusts at block 5506. The block 5506 is shown in dashed outline because the process may be performed by another device (e.g., the IOL). The focus may adjust for near objects by increasing refractive power (e.g., to allow the user to focus on near objects) and/or adjust for intermediate to distance vision by decreasing refractive power (e.g., to allow the user to focus on intermediate and/or distant objects).

An example of an IOL that may be focus adjusted at block 5504 is ELENZA Sapphire from Elenza. Upon sensing a change in the natural pupil, the Elenza IOL can accommodate, or focus. For example, upon sensing that the natural pupil is constricting, the Elenza IOL can myopically accommodate. As another example, upon sensing that the natural pupil is dilating, an IOL may return to the dis-accommodated state for emmetropia. As another example, upon sensing that the natural pupil is dilating, an IOL may return adjust focus for intermediate and/or distant object viewing. In some implementations, the transmission at block 5506 may effect accommodation regardless of a state of the natural pupil. In some implementations, the transmission at block 5506 may effect accommodation in combination with sensing of a change in a natural pupil.

Another example of focus adjustment at block 5504 is by a technology device comprising an artificial pupil or electronically-controlled iris diaphragm configured to selectively block light transmission into the eye. The transmission at block 5506 can instruct the artificial pupil to constrict and/or dilate. In some implementations, an artificial pupil could effectively work for patients with damaged or missing iris tissue and/or to provide increased depth of focus, creating a hyperfocality by decreasing the effective aperture size. In some implementations, an artificial pupil allows the user to achieve better near and intermediate vision in adequate lighting, without the loss of distance vision. An example of a static device that could achieve these refractive benefits is the Acufocus Kamra. This device is typically implanted either in the cornea or upon an IOL, and heretofore not been controllable by the user, for example in a manner that can increase or optimize functionality. In some implementations, upon application of an electrical wireless transmission, the technology device works similarly to a camera aperture, closing circumferentially from the limbal toward the visual axis. In some implementations, upon application of an electrical wireless transmission, the molecular configuration of liquid crystals in the technology device orient to make an edge opaque, akin to the result of pupil constriction. The artificial pupil may work in combination with the natural pupil, or may provide beneficial refractive effects independent of the natural pupil. In some implementations, an artificial pupil may work in combination with accommodation of an IOL such as the Elenza IOL. In some implementations, a technology device of the prosthetic capsular device comprises the artificial pupil, which may be used in combination with an IOL, an accommodating IOL, or without an IOL.

Another example of an IOL that may be focus adjusted at block 5504 is Light Adjustable Lens (LAL) from Calhoun Vision that has not been locked in. Upon application of an electrical wireless transmission, light is directed to cause photopolymerization of macromers and swelling in an illuminated area, causing a change in power. The focus of the IOL may be changed using a microsolenoid (e.g., application of an electrical wireless transmission to a coil creates a magnetic field that attracts or repels a magnetic material coupled to a refractive surface), MEMS (e.g., application of an electrical wireless transmission creates an electrostatic charge that attracts a hinged metallic material coupled to a refractive surface), etc. The entire IOL or portions thereof (e.g., a refractive surface) may move within the prosthetic capsular device, providing a focusing mechanism to non-adjustable IOLs.

In some implementations, the IOL and/or the technology device may send a wireless transmission, command instruction, computer-generated message, or the like to the external device to confirm that focus adjusted. Although the focus adjustment may be visible to a user, such feedback may aid in initial setup, calibration, troubleshooting, etc. In certain such implementations, the process may optionally further comprise receipt of a confirmation wireless transmission by the external device that the focus was adjusted.

The external device may optionally be configured to receive other wireless transmissions from the IOL and/or the technology device (e.g., low battery, error codes, limits reached, etc.). In certain such implementations, the emission of the wireless transmission by the external device 5504 may be based on confirmation that the IOL is able to focus in accordance with the wireless transmission. The external device may optionally be configured to receive other wireless transmissions from the IOL and/or the technology device other than regarding focus, for example as described in further detail herein.

The process ends at block 5508. The focus of the IOL may revert after some amount of time or in response to a second wireless transmission from the external device (e.g., upon receipt of a second user input). Some of the processes discussed above and other processes are described in more detail with respect to FIGS. 24B-24F.

FIG. 24B is a schematic of a system for controlling an electronic device (e.g., technology device and/or an IOL) using an external device. In the illustrated flowchart, a prosthetic capsular device 5510 includes a technology device. The prosthetic capsular device 5510 at least partially contains an IOL 5512. The technology device of the prosthetic capsular device 5510 and/or the IOL 5512 is in communication with a primary external device 5514. The primary external device 5514 may comprise, for example, a smartphone, a smartwatch, etc. The primary external device 5514 is optionally in communication with a secondary external device 5516. The secondary external device 5516 may comprise, for example, a smartwatch (e.g., in combination with the primary external device 5514 comprising a smartphone). The secondary external device 5516 is optionally in communication with a tertiary external device 5518. The tertiary external device 5518 may comprise, for example, a ring (e.g., in combination with the secondary external device 5516 comprising a smartwatch). The primary external device 5514, the secondary external device 5516, and the tertiary external device 5518 may act singly, in subcombination, or in full combination to, inter alia, receive input by a user and emit a wireless transmission to the technology device of the prosthetic capsular device 5510 and/or the IOL 5512. Additional external devices (e.g., quarternary, quinary, etc.) are also possible.

FIG. 24C is a flowchart of an example method of controlling an electronic device (e.g., technology device and/or an IOL) using an external device. Starting at block 5520, the external device receives input from a user at block 5522. Upon receipt of the user input at block 5522, the external device processes the user input at block 5524. The external device may include a processing module, a static memory module, a dynamic or temporary memory module, a power source, a user input receipt module, a wireless transmission emitting module, a wireless transmission receiving module, and the like. Upon processing of the user input at block 5524, the external device generates an instruction command for transmission to an electronic device (e.g., a technology device of a prosthetic capsular device, an IOL, etc.) implanted in the eye at block 5526. The generation of the instruction command may be automatic upon receipt and processing of the user input, or may include further interaction with the user or another device. The instructions may include, for example, to focus the IOL. Upon generation of the instruction command at block 5526, the external device may optionally receive confirmation and/or a current status input from the electronic device (e.g., a technology device of a prosthetic capsular device, an IOL, etc.) implanted in the eye at block 5528. Depending on generation of the instruction command and/or receipt of the confirmation and/or current status input from the electronic device, the process may repeat starting at block 5522 or end at block 5530.

FIG. 24D is a flowchart of another example method of controlling an electronic device (e.g., technology device and/or an IOL) using an external device. Referring to FIG. 24B, for example, the external device comprises a primary external device (e.g., a smartphone) and a secondary external device (e.g., a smartwatch). Starting at block 5532, the secondary external device receives input from a user at block 5534. Upon receipt of the user input at block 5534, the primary external device receives the user input from the secondary external device at block 5536. The primary external device may be in wired or wireless communication with the secondary external device so as to receive the user input directly or as a result of a wireless transmission from the secondary external device. Upon receipt of the user input at block 5536, the primary external device processes the user input at block 5538. Upon processing of the user input at block 5538, the primary external device generates an instruction command for transmission to an electronic device (e.g., a technology device of a prosthetic capsular device, an IOL, etc.) implanted in the eye at block 5540. The generation of the instruction command may be automatic upon receipt and processing of the user input, or may include further interaction with the user, the secondary external device, another device, etc. The instructions may include, for example, to focus the IOL. Upon generation of the instruction command at block 5540, the primary external device may optionally receive confirmation and/or a current status input from the electronic device (e.g., a technology device of a prosthetic capsular device, an IOL, etc.) implanted in the eye at block 5542. The primary external device and/or the secondary external device may optionally display the confirmation and/or current status input at block 5544. Depending on generation of the instruction command, receipt of the confirmation and/or current status input from the electronic device, and/or display of the confirmation and/or current status input, the process may repeat starting at block 5534 or end at block 5546.

Figure 24E:
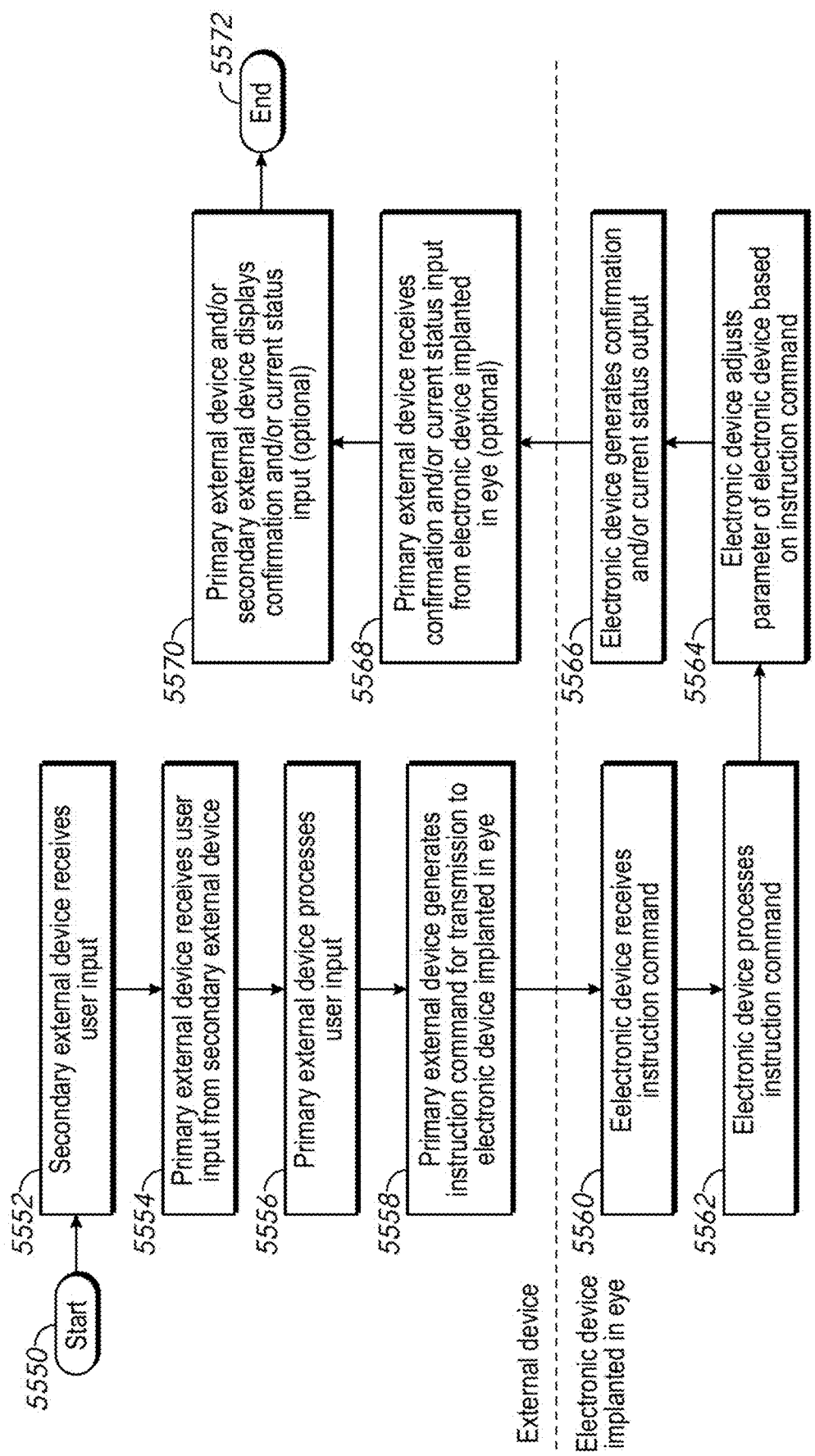
FIG. 24E is a flowchart of another example of controlling an electronic device using an external device.

FIG. 24E is a flowchart of another example method of controlling an electronic device (e.g., technology device and/or an IOL) using an external device. Referring to FIG. 24B, for example, the external device comprises a primary external device (e.g., a smartphone) and a secondary external device (e.g., a smartwatch). Starting at block 5550, the secondary external device receives input from a user at block 5552. Upon receipt of the user input at block 5552, the primary external device receives the user input from the secondary external device at block 5554. The primary external device may be in wired or wireless communication with the secondary external device so as to receive the user input directly or as a result of a wireless transmission from the secondary external device. Upon receipt of the user input at block 5554, the primary external device processes the user input at block 5556. Upon processing of the user input at block 5556, the primary external device generates an instruction command for transmission to an electronic device (e.g., a technology device of a prosthetic capsular device, an IOL, etc.) implanted in the eye at block 5558. The generation of the instruction command may be automatic upon receipt and processing of the user input, or may include further interaction with the user, the secondary external device, another device, etc. The instructions may include, for example, to focus the IOL.

FIG. 24E includes a dashed horizontal line indicative of processes that may be performed by the electronic device (e.g., a technology device of a prosthetic capsular device, an IOL, etc.) implanted in the eye. It will be appreciated that the electronic device may be separate from the external device, and that the processes described with respect to FIG. 24E are examples for reference only. In some implementations, the external device and the electronic device form a system or kit.

The electronic device may receive the instruction command at block 5560. Upon receipt of the instruction command at block 5560, the electronic device may process the instruction command at block 5562. Upon processing of the instruction command at block 5562, the electronic device may adjust a parameter of the electronic device based on the instruction command at block 5564. The adjustment of the parameter may be automatic upon receipt and processing of the instruction command, or may include further interaction with the user, the primary external device, the secondary external device, and/or another device, analysis of the parameter and/or another parameter, etc. The parameter may include, for example, IOL focus (e.g., an amount of masking, an amount of movement, an amount of rotation, etc.). Upon adjustment of the parameter at block 5564, the electronic device may generate confirmation and/or a current status output at block 5566. The electronic device may perform more, fewer, different, differently ordered, etc. processes, may include interaction between multiple electronic devices (e.g., between a technology device of a prosthetic capsular device and an IOL), etc.

The primary external device may optionally receive confirmation and/or a current status input (generated as output) from the electronic device implanted in the eye at block 5568. The primary external device and/or the secondary external device may optionally display the confirmation and/or current status input at block 5570. The process ends at block 5572.

Figure 24F:
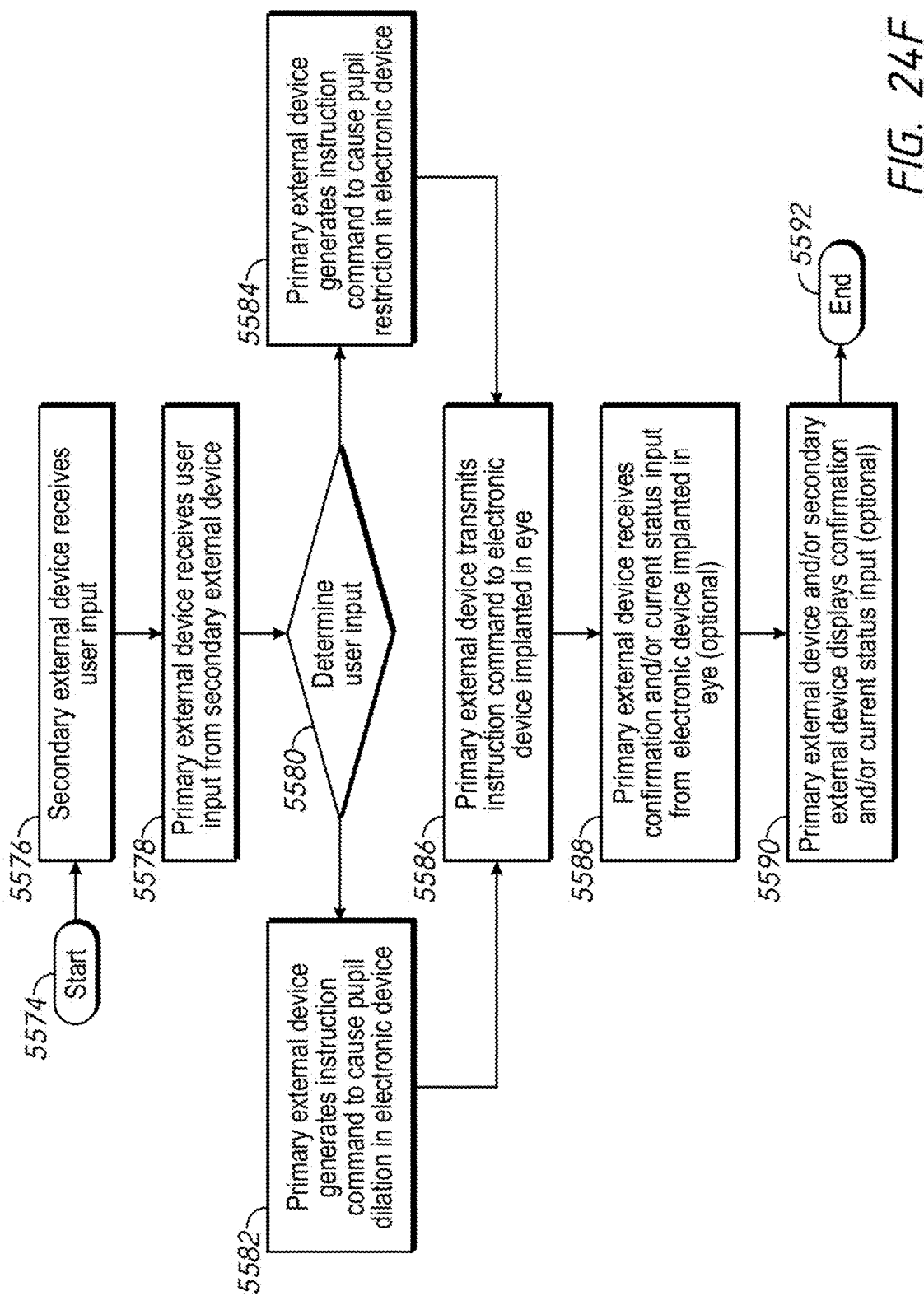
FIG. 24F is a flowchart of another example of controlling an electronic device using an external device.

FIG. 24F is a flowchart of another example method of controlling an electronic device (e.g., technology device and/or an IOL) using an external device. Referring to FIG. 24B, for example, the external device comprises a primary external device (e.g., a smartphone) and a secondary external device (e.g., a smartwatch). Starting at block 5574, the secondary external device receives input from a user at block 5576. Upon receipt of the user input at block 5576, the primary external device receives the user input from the secondary external device at block 5578. The primary external device may be in wired or wireless communication with the secondary external device so as to receive the user input directly or as a result of a wireless transmission from the secondary external device.

The primary external device determines the user input at block 5580. In the event of a first user input, the primary external device generates an instruction command to change focus to near objects (e.g., myopic accommodation as described herein with respect to the Elenza IOL) at block 5582. In the event of a second user input different than the first user input, the primary external device generates an instruction command to change focus to intermediate and/or distant objects (e.g., emmetropia or a dis-accommodated state as described herein) at block 5584. For clarity, the Elenza IOL uses pupillary constriction as a sign that the eye is trying to accommodate (focus) and the lens changes focus based on the natural pupillary constriction. That is, the Elenza IOL does not cause the pupil to constrict and does not contain a prosthetic iris device. In some implementations, instruction commands described herein could, for example, cause the Elenza IOL to change focus regardless of constriction of the natural pupil.

In some implementations, for example using an IOL other than an Elenza IOL or by way of a technology device of a prosthetic capsular device, an instruction command could, for example, effect constriction or dilation of an artificial pupil.

Focus adjustment of an Elenza IOL and constriction/dilation of an artificial pupil and are provided as example parameter changes, and it will be appreciated that other parameter changes based on different inputs is also possible. The generation of the instruction commands may be automatic upon receipt and processing of the user input, or may include further interaction with the user (e.g., instruction command in combination with sensing of natural pupil dilation), the secondary external device, another device, etc. In some implementations, the secondary external device may determine the user input and the primary external device may receive an instruction command.

Upon generation of the instruction command at block 5582 or 5584, the primary external device transmits the instruction command to an electronic device (e.g., a technology device of a prosthetic capsular device, an IOL, etc.) implanted in the eye at block 5586. The instructions may include, for example, to focus the IOL. Upon transmission of the instruction command at block 5586, the primary external device may optionally receive confirmation and/or a current status input from the electronic device (e.g., a technology device of a prosthetic capsular device, an IOL, etc.) implanted in the eye at block 5588. The primary external device and/or the secondary external device may optionally display the confirmation and/or current status input at block 5590. The process ends at block 5592.

Figure 25:
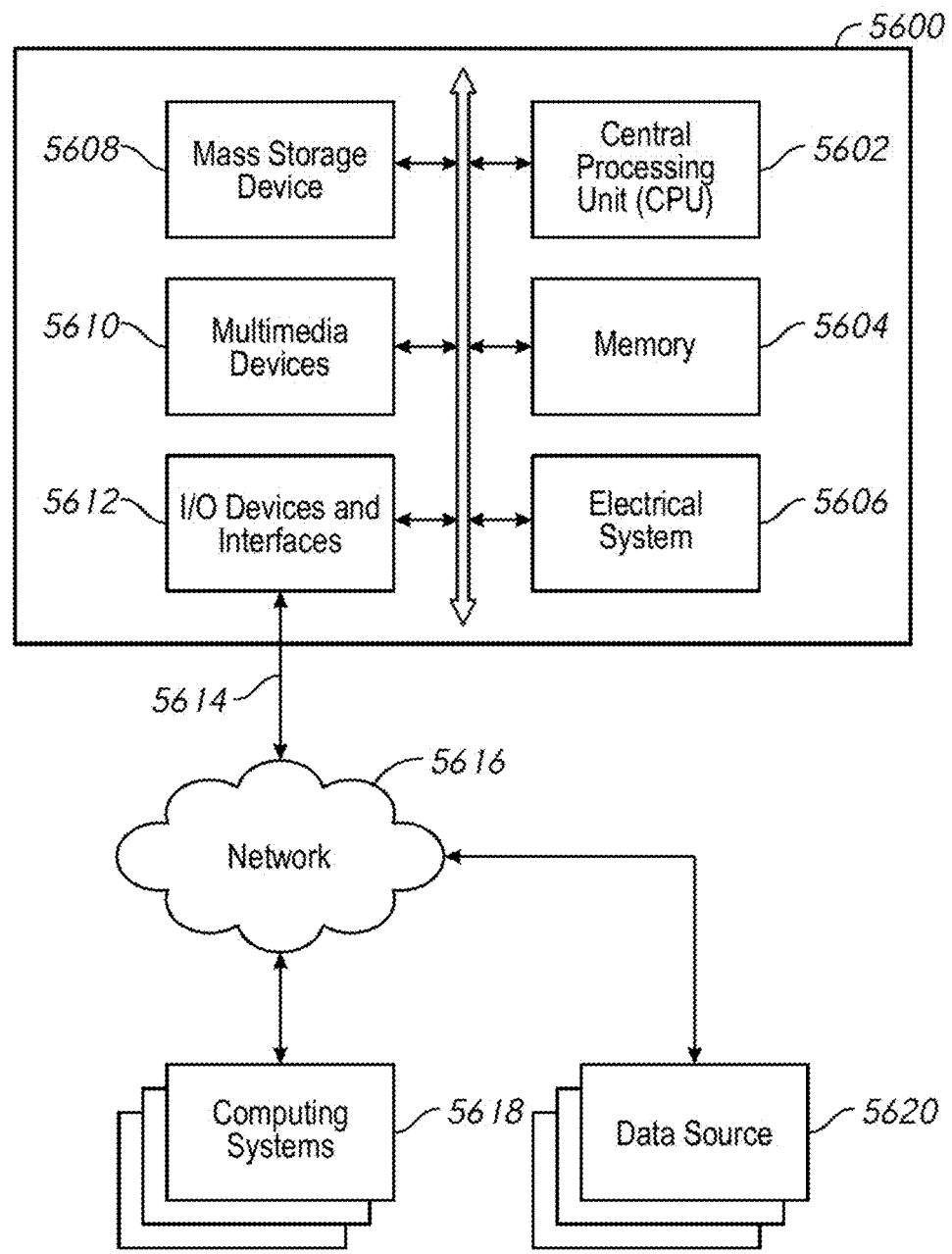
FIG. 25 is a block diagram depicting an example computer hardware system configured to execute software for implementing one or more embodiments of electronic device control disclosed herein.

FIG. 25 is a block diagram depicting an example computer hardware system configured to execute software for implementing one or more implementations of electronic device control disclosed herein In some implementations, the hardware systems and/or devices described above take the form of a computing system 5600, which is a block diagram of one implementation of a computing system that is in communication with one or more computing systems 5618 and/or one or more data sources 5620 via one or more networks 5616. The computing system 5600 may be used to implement one or more of the systems and methods described herein. In some implementations, the computing system 5600 is configured to manage access or administer a software application. While FIG. 25 illustrates an example computing system 5600, it is recognized that the functionality provided for in the components and modules of the computing system 5600 may be combined into fewer components and modules or further separated into additional components and modules.

Electrical System

In some implementations, the computing system 5600 comprises an electrical system 5606 configured to carry out one or more of the functions described herein with reference to control of an electronic device implanted in an eye, including any one of techniques described above. The electrical system 5606 and/or other modules may be executed on the computing system 5600 by a central processing unit 5602 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Computing System Components

The computing system 5600 can comprise a central processing unit (CPU) 5602, which may comprise a conventional microprocessor. The computing system 5600 further comprises a memory 5604, such as random access memory (RAM) for temporary storage of information and/or a read only memory (ROM) for permanent storage of information, and a mass storage device 5608, such as a hard drive, diskette, or optical media storage device. In some implementations, the modules of the computing system 5600 are connected to the computer using a standards based bus system. In some implementations, the standards-based bus system could include Peripheral Component Interconnect (PCI), Microchannel, SCSI, Industrial Standard Architecture (ISA) and Extended ISA (EISA) architectures, for example.

The computing system 5600 comprises one or more commonly available input/output (I/O) devices and interfaces 5612, such as a keyboard, mouse, touchpad, touchscreen, ring, printer, etc. In some implementations, the I/O devices and interfaces 5612 comprise one or more display devices, such as a monitor or touchscreen, that allows the visual presentation of data to a user. A display device can provide for the presentation of graphical user interfaces (GUI), application software data, and multimedia presentations, for example. In some implementations, the I/O devices and interfaces 5612 comprise a microphone, motion, and/or NFC sensor that allows a user to generate input to the computing system 5600 using sounds, voice, motion, gestures, or the like. In FIG. 25, the I/O devices and interfaces 5612 also provide a communications interface to various external devices via a link 5614 to the network 5616. The computing system 5600 may also comprise one or more multimedia devices 5610, such as speakers, video cards, graphics accelerators, and microphones, for example.

Computing System Device/Operating System

The computing system 5600 may run on a variety of computing devices, such as, for example, a specifically designed device, a server, a Windows server, a Structure Query Language server, a Unix server, a personal computer, a mainframe computer, a laptop computer, a tablet computer, a cell phone, a smartphone, a smartwatch, a personal digital assistant, a kiosk, an audio player, an e-reader device, and so forth. The computing system 5600 is generally controlled and coordinated by operating system software, such z/OS, Windows 95, Windows 98, Windows NT, Windows 2000, Windows XP, Windows Vista, Windows 7, Windows 8, Linux, BSD, SunOS, Solaris, Android, iOS, BlackBerry OS, or other compatible operating systems. In Macintosh systems, the operating system may be any available operating system, such as MAC OS X. In some implementations, the computing system 5600 is controlled by a proprietary operating system. The operating system may, for example, control and schedule computer processes for execution, perform memory management, provide file system, networking, and I/O services, and provide a user interface, such as a GUI, among other things.

Network

FIG. 25 illustrates the computing system 5600 is coupled to an optional network 5616, such as a LAN, WAN, or the Internet, for example, via a wired, wireless, or combination of wired and wireless, communication link 5614. The network 5616 communicates with various computing devices and/or other electronic devices via wired or wireless communication links. In FIG. 25, the network 5616 is communicating with one or more computing systems 5618 and/or one or more data sources 5620.

Access to the electrical system 5606 of the computer system 5600 by computing systems 5618 and/or by data sources 5620 may be through a web-enabled user access point such as the computing systems' 5618 or data source's 5620 personal computer, mobile device, cellular phone, smartphone, smartwatch, laptop, tablet computer, e-reader device, audio player, or other device capable of connecting or configured to connect to the network 5616. Such a device may have a browser module or specific application that is implemented as a module that uses text, graphics, audio, video, and other media to present data and to allow interaction with data via the network 5616.

The browser module or specific application may be implemented as a combination of an all points addressable display such as a cathode-ray tube (CRT), a liquid crystal display (LCD), a plasma display, or other types and/or combinations of displays. The browser module or specific application may be implemented to communicate with input devices 5612 and may comprise software with the appropriate interfaces to allow a user to access data through the use of stylized screen elements such as, for example, menus, windows, dialog boxes, toolbars, and controls (for example, radio buttons, check boxes, sliding scales, and so forth). The browser module may communicate with a set of input and output devices to receive wireless transmissions from the user.

The input device(s) may comprise a keyboard, roller ball, pen and stylus, mouse, ring, smartwatch, knob, trackball, voice recognition system, or pre-designated switches or buttons. The output device(s) may comprise a speaker, a display screen, a printer, or a voice synthesizer. A touch screen may act as a hybrid input/output device. In some implementations, a user may interact with the system through a system terminal without communications over the Internet, a WAN, or LAN, or similar network.

In some implementations, the system 5600 comprises a physical or logical connection between a remote microprocessor and a mainframe host computer for the purpose of uploading, downloading, or viewing interactive data and databases on-line in real time. The remote microprocessor may be operated by an entity operating the computer system 5600, including the client server systems or the main server system, and/or may be operated by one or more of the data sources 5620 and/or one or more of the computing systems 5618. In some implementations, terminal emulation software may be used on the microprocessor for participating in the micro-mainframe link.

In some implementations, computing systems 5618 that are internal to an entity operating the computer system 5600 may access the electrical system 5606 internally as an application or process run by the CPU 5602.

User Access Point

In some implementations, a user access point or user interface comprises a personal computer, a laptop computer, a tablet computer, an e-reader device, a mobile device, a cellular phone, a smartphone, a smartwatch, a GPS system, a Blackberry® device, a portable computing device, a server, a computer workstation, a local area network of individual computers, an interactive kiosk, a personal digital assistant, an interactive wireless communications device, a handheld computer, an embedded computing device, an audio player, or the like.

Other Systems

In addition to the systems illustrated and described above, the network 5616 may communicate with other data sources and/or other computing devices. The computing system 5600 may comprise one or more internal and/or external data sources. In some implementations, one or more of the data repositories and the data sources may be implemented using a relational database, such as DB2, Sybase, Oracle, CodeBase, Microsoft® SQL Server, as well as other types of databases such as, for example, a flat file database, an entity-relationship database, and object-oriented database, and/or a record-based database.

EXAMPLE EMBODIMENTS

The following example embodiments identify some possible permutations of combinations of features disclosed herein, although other permutations of combinations of features are also possible.

1. A prosthetic capsular device system configured to be inserted in an eye, the system comprising:
  prosthetic capsular device comprising:
   an anterior surface including an opening, and
   a posterior surface, at least a portion of the posterior surface comprising a refractive surface; and
  a technology device.

2. The system of embodiment 1, further comprising an intraocular lens positioned such that the technology device does not substantially interfere with sight lines through the intraocular lens.

3. The system of embodiment 2, wherein the technology device is configured to control a property of the intraocular lens.

4. The system of embodiment 3, wherein the controlled property of the intraocular lens includes at least one of: refractive capabilities, light transmission, UV transmission, and accommodative properties.

5. The system of any one of embodiments 2-4, wherein the technology device forms an integral part of the intraocular lens, and wherein the technology device surrounds all or part of an outer perimeter edge of the intraocular lens.

6. The system of any one of embodiments 1-5, wherein the technology device comprises at least one of a computer, a virtual reality device, a display device, an internet access device, a receiver, a game device, an image viewer, a projector, a global positioning system, an e-mail device, and a biometric sensor device.

7. The system of embodiment 6, wherein the receiver comprises a digital data receiver.

8. The system of any one of embodiments 1-7, wherein the technology device comprises a power source capable of being recharged from outside the eye.

9. The system of any one of embodiments 1-8, wherein the prosthetic capsular device comprises an exterior contour configured to mechanically maintain the prosthetic capsular device at a specific position within the eye.

10. The system of embodiment 9, wherein the exterior contour is configured to extend into a ciliary sulcus.

11. The system of any one of embodiments 9 and 10, wherein the exterior contour comprises a flange extending radially outwardly from the opening.

12. The system of any one of embodiments 1-11, wherein the refractive surface includes at least one of the following optical and design qualities: concave, convex, spherical, aspheric, wavefront, multifocal diffractive, multifocal refractive, multifocal zonal, accommodative, UV filtering, diffractive chromatic aberration reducing, and astigmatism correcting tonic form.

13. The system of any one of embodiments 1-12, wherein the technology device is configured to control at least one of the following properties of the prosthetic capsular device: light transmission, UV transmission, and heat insulation.

14. A method of operating on an eye, the method comprising:
  inserting a prosthetic capsular device in the eye, the prosthetic capsular device including:
   an anterior surface including an opening, and
   a posterior surface, at least a portion of the posterior surface comprising a refractive surface; and
  inserting a technology device in the prosthetic capsular device.

15. The method of embodiment 14, wherein the technology device comprises at least one of a computer, a virtual reality device, a display device, an internet access device, a receiver, a game device, an image viewer, a projector, a global positioning system, an e-mail device, and a biometric sensor device.

16. The method of any one of embodiments 14 and 15, further comprising inserting an intraocular lens in the prosthetic capsular device, wherein after inserting the intraocular lens the technology device does not substantially interface with sight lines through the intraocular lens.

17. The method of any one of embodiments 14-16, wherein the technology device is configured to control one or more properties of the intraocular lens.

18. The method of embodiment 17, wherein the controlled properties of the intraocular lens includes at least one of: refractive capabilities, light transmission, UV transmission, and accommodation properties.

19. The method of any one of embodiments 16-18, wherein the technology device forms an integral part of the intraocular lens, and wherein the technology device surrounds all or part of an outer perimeter edge of the intraocular lens.

20. The method of any one of embodiments 14-19, wherein the technology device comprises a power source capable of being recharged from outside the eye.

21. The method of any one of embodiments 14-20, wherein inserting the prosthetic capsular device comprises inserting the prosthetic capsular device in a natural capsular bag of the eye.

22. The method of embodiment 21, further comprising, before inserting the prosthetic capsular device, removing a natural lens from the natural capsular bag, the natural lens including a posterior surface at a location in the natural capsular bag before removing the natural lens, and wherein the prosthetic capsular device is dimensioned to be at a position that is at least one of substantially identical to, measurably different than, and predictably different than the location of the posterior surface of the natural lens.

23. The method of any one of embodiments 14-22, further comprising, before inserting the prosthetic capsular device, forming an anterior capsulorhexis in natural capsular bag of the eye, wherein inserting the prosthetic capsular device is through the anterior capsulorhexis.

24. The method of any one of embodiments 14-23, wherein the prosthetic capsular device includes an exterior contour configured to mechanically maintain the prosthetic capsular device at a specific position within the eye.

25. The method of any one of embodiments 14-24, wherein the technology device is configured to control at least one of the following properties of the prosthetic capsular device: light transmission, UV transmission, and heat insulation.

26. A prosthetic capsular device for insertion into an eye holding a technology device.

27. A prosthetic capsular bag or capsular enclosing device, for insertion into the eye, which holds a miniaturized wearable electronic technology device.

28. A prosthetic capsular device for insertion into an eye, the prosthetic capsular device comprising:
an anterior surface including an opening;
a posterior surface, at least a portion of the posterior surface comprising a refractive surface; and
an external surface comprising form-fitting elements.

29. The prosthetic capsular device of embodiment 28, wherein the form-fitting elements comprise a plurality of tabs.

30. The prosthetic capsular device of embodiment 29, wherein the plurality of tabs are substantially continuous along an outer rim of the external surface.

31. The prosthetic capsular device of any one of embodiments 29 and 30, wherein at least one of the tabs comprises an opening through which fibrosis can take place.

32. The prosthetic capsular device of any one of embodiments 29 and 30, wherein each of the tabs comprises an opening through which fibrosis can take place.

33. The prosthetic capsular device of any one of embodiments 28-32, wherein the form-fitting elements comprise at least one of silicone, silicone derivatives, acrylic, acrylic derivatives, PMMA, olefin, polyimide, and collamer.

34. The prosthetic capsular device of any one of embodiments 28-33, further comprising an internal lip or sulcus configured to secure haptics of an intraocular lens in the device.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. For example, actions such as "inserting an intraocular lens into a prosthetic capsular device" include "instructing the insertion of an intraocular lens into a prosthetic capsular device." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant."

What is claimed is:

1. A prosthetic capsular device configured to be inserted in a natural capsular bag of an eye after removal of a lens, the device comprising:
a housing structure having a discoid shape configured to contain one or more intraocular lenses or technology devices, the housing structure comprising:
a longitudinal axis;
a posterior side;
an anterior side opposite the posterior side, the anterior side comprising an anterior opening having rounded edges;
a continuous lateral side extending between the posterior side and the anterior side, the continuous lateral side comprising one or more protrusions projecting radially therefrom, wherein the one or more protrusions are continuous around a perimeter of the device;
a cavity at least partially defined by the posterior side, the anterior side, and the continuous lateral side, wherein the cavity is configured to contain the one or more intraocular lenses or technology devices, and wherein the anterior opening is configured to allow insertion of the one or more intraocular lenses or technology devices into the cavity of the housing structure through the anterior opening; and an exterior surface of the housing structure comprising a straight-walled portion extending parallel to the longitudinal axis from the posterior side towards the anterior side, wherein the exterior surface of the housing structure tapers radially inward from the straight-walled portion to the anterior opening.

2. The prosthetic capsular device of claim 1, wherein the continuous lateral side comprises one protrusion.

3. The prosthetic capsular device of claim 1, wherein the continuous lateral side comprises more than one protrusion.

4. The prosthetic capsular device of claim 1, wherein the prosthetic capsular device comprises a biologically-compatible material.

5. The prosthetic capsular device of claim 1, wherein the prosthetic capsular device is deformable.

6. The prosthetic capsular device of claim 1, wherein the prosthetic capsular device is foldable.

7. The prosthetic capsular device of claim 1, wherein the prosthetic capsular device possesses sufficient elasticity to resume its pre-folded shape.

8. The prosthetic capsular device of claim 1, wherein the prosthetic capsular device is self-expanding.

9. The prosthetic capsular device of claim 1, wherein the prosthetic capsular device comprises an optically clear material.

10. A prosthetic capsular device configured to be inserted in a natural capsular bag of an eye after removal of a lens, the device comprising:

a housing structure having a discoid shape configured to contain one or more intraocular lenses or technology devices, the housing structure comprising:

a longitudinal axis;

a posterior side;

an anterior side opposite the posterior side, the anterior side comprising an anterior opening having rounded edges;

a continuous lateral side extending between the posterior side and the anterior side, the continuous lateral side comprising a protrusion projecting therefrom;

a cavity at least partially defined by the posterior side, the anterior side, and the continuous lateral side, wherein the cavity is configured to contain the one or more intraocular lenses or technology devices, wherein the anterior opening is configured to allow insertion of the one or more intraocular lenses or technology devices into the cavity of the housing structure through the anterior opening, and wherein at least one of the one or more intraocular lenses or technology devices comprise a technology device;

an exterior surface of the housing structure comprising a straight-walled portion extending parallel to the longitudinal axis from the posterior side towards the anterior side, wherein the exterior surface of the housing structure tapers radially inward from the straight-walled portion to the anterior opening; and an insulation structure that thermally insulates the eye from heat produced by the at least one technology device contained in the cavity.

* * * * *

UNITED STATES PATENT AND TRADEMARK OFFICE
CERTIFICATE OF CORRECTION

Page 1 of 2

PATENT NO. : 10,842,615 B2
APPLICATION NO. : 15/980613
DATED : November 24, 2020
INVENTOR(S) : Gary N. Wortz It is certified that error appears in the above-identified patent and that said Letters Patent is hereby corrected as shown below:

On the Title Page

On Page 5, Column 1, Item (56), under Other Publications, Line 9, delete "Opinoin" and insert --Opinion--.

On Page 5, Column 2, Item (56), under Other Publications, Line 21, delete "Postive" and insert --Positive--.

On Page 5, Column 2, Item (56), under Other Publications, Line 29, delete "posiiton" and insert --position--.

In the Drawings

On Sheet 66 of 68, FIG. 24E, Line 1, Reference Number 5560, delete "Eelectronic" and insert --Electronic--.

In the Specification

In Column 1, Line 49, delete "toric" and insert --tonic--.

In Column 8, Line 23, delete "positon" and insert --position--.

In Column 10, Line 51, delete "(FA)" and insert --(I/A)--.

In Column 16, Line 13, delete "AB" and insert --A/B--.

In Column 18, Line 1, delete "diopteric" and insert --dioptric--.

In Column 23, Line 18, delete "Crysalens" and insert --Crystalens--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,842,615 B2

In Column 25, Line 13, delete "(e.g.," and insert --e.g.,--.

In Column 38, Line 4, delete "quarternary," and insert --quaternary,--.

In the Claims

In Column 44, Line 43, Claim 12, delete "tonic" and insert --toric--.